United States Patent
Mizoi et al.

(10) Patent No.: US 11,491,895 B2
(45) Date of Patent: Nov. 8, 2022

(54) ECU DEVICE, VEHICLE SEAT, SYSTEM FOR ESTIMATING LOWER LIMB LENGTH OF SEATED PERSON, AND ATTACHMENT STRUCTURE FOR SITTING HEIGHT DETECTION SENSOR

(71) Applicant: TS TECH CO., LTD., Asaka (JP)

(72) Inventors: Kensuke Mizoi, Shioya-gun (JP); Naoto Yamauchi, Shioya-gun (JP)

(73) Assignee: TS TECH CO., LTD., Asaka (JP)

( * ) Notice: Subject to any disclaimer, the term of this patent is extended or adjusted under 35 U.S.C. 154(b) by 95 days.

(21) Appl. No.: 17/050,590

(22) PCT Filed: Apr. 26, 2019

(86) PCT No.: PCT/JP2019/017908
§ 371 (c)(1),
(2) Date: Oct. 26, 2020

(87) PCT Pub. No.: WO2019/208764
PCT Pub. Date: Oct. 31, 2019

(65) Prior Publication Data
US 2021/0237620 A1     Aug. 5, 2021

(30) Foreign Application Priority Data

Apr. 27, 2018 (JP) .............................. JP2018-085929
Apr. 27, 2018 (JP) .............................. JP2018-085930
(Continued)

(51) Int. Cl.
*B60N 2/00* (2006.01)
*B60N 2/02* (2006.01)
(Continued)

(52) U.S. Cl.
CPC ........... *B60N 2/0244* (2013.01); *B60N 2/002* (2013.01); *G01B 5/02* (2013.01); *G01B 11/026* (2013.01);
(Continued)

(58) Field of Classification Search
CPC .......... B60N 2002/0268; B60N 2/0244; B60N 2/002
See application file for complete search history.

(56) References Cited

U.S. PATENT DOCUMENTS

| | | | |
|---|---|---|---|
| 2012/0053794 A1* | 3/2012 | Alcazar ................ | B60N 2/0244 701/49 |
| 2013/0009761 A1* | 1/2013 | Horseman ............ | A61B 5/6893 340/576 |

(Continued)

FOREIGN PATENT DOCUMENTS

| EP | 2927048 A1 * | 10/2015 | ............. B60N 2/002 |
|---|---|---|---|
| JP | H07-81468 A | 3/1995 | |

(Continued)

OTHER PUBLICATIONS

Jul. 16, 2019 Search Report issued in International Patent Application No. PCT/JP2019/017908.
(Continued)

*Primary Examiner* — Timothy J Brindley
(74) *Attorney, Agent, or Firm* — Oliff PLC

(57) ABSTRACT

An ECU device which estimates a length of a lower limb of a seated person who is seated in a vehicle seat is shown. The ECU device includes the following. A thigh angle information obtainer obtains information regarding a thigh angle of the seated person. A back knee angle information obtainer obtains information regarding a back knee angle of the seated person. An estimator estimates the length of the lower limb of the seated person based on the information regarding the thigh angle obtained by the thigh angle information obtainer and information regarding the back knee angle obtained by the back knee angle information obtainer.

13 Claims, 39 Drawing Sheets

(30) Foreign Application Priority Data

Oct. 26, 2018 (JP) .............................. JP2018-201849
Oct. 26, 2018 (JP) .............................. JP2018-201959

(51) Int. Cl.
*G01B 11/02* (2006.01)
*G01B 5/02* (2006.01)

(52) U.S. Cl.
CPC .... *B60N 2/0232* (2013.01); *B60N 2002/0268* (2013.01)

(56) References Cited

U.S. PATENT DOCUMENTS

| 2019/0111938 A1* | 4/2019 | Chen | H04L 41/0886 |
| 2020/0077803 A1* | 3/2020 | Hayashi | B60N 2/002 |
| 2021/0118170 A1* | 4/2021 | Fujii | G06T 7/75 |
| 2022/0063448 A1* | 3/2022 | Munoz Perez | B60R 11/04 |

FOREIGN PATENT DOCUMENTS

| JP | H08-098736 A | 4/1996 | | |
| JP | 2006-290099 A | 10/2006 | | |
| JP | 2008-162430 A | 7/2008 | | |
| JP | 2010-233647 A | 10/2010 | | |
| JP | 2016-144985 A | 8/2016 | | |
| JP | 2017-30611 A | 2/2017 | | |
| JP | 2017-81463 A | 5/2017 | | |
| JP | 2019177780 A | * | 10/2019 | ............. B60N 2/002 |
| KR | 20210149502 A | * | 6/2020 | |
| KR | 20220050286 A | * | 10/2020 | |
| WO | WO-2008071284 A1 | * | 6/2008 | ........... B60N 2/0244 |
| WO | WO-2021175516 A1 | * | 9/2021 | ............. B60N 2/002 |

OTHER PUBLICATIONS

Sep. 27, 2022 Office Action issued in Japanese Patent Application No. 2018-201959.

* cited by examiner

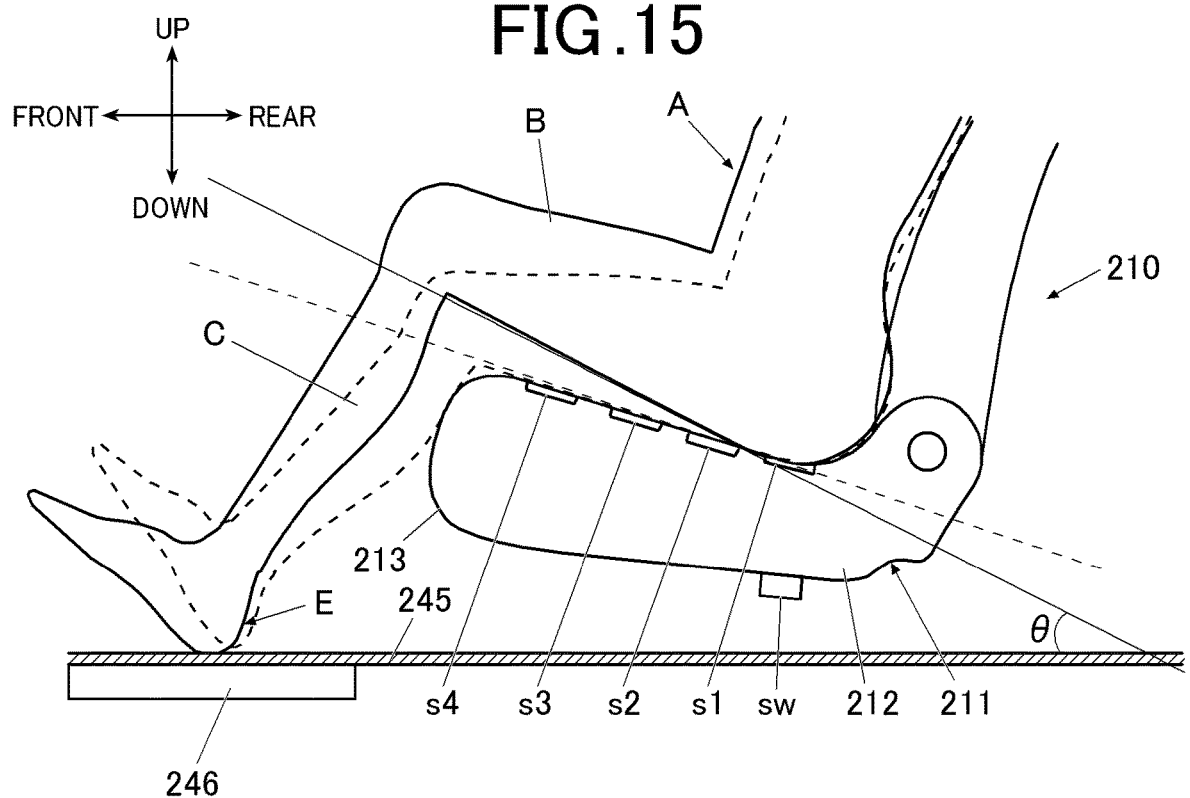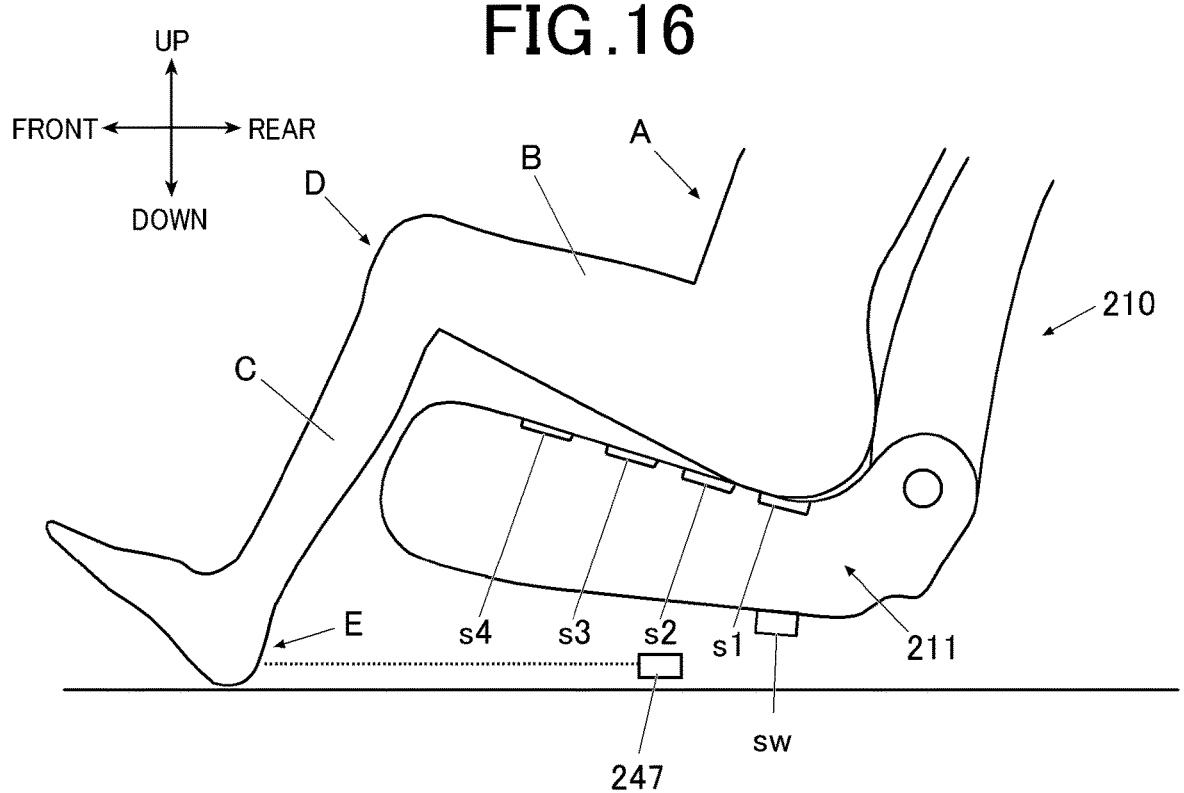

31  30  32

ECU DEVICE, VEHICLE SEAT, SYSTEM FOR ESTIMATING LOWER LIMB LENGTH OF SEATED PERSON, AND ATTACHMENT STRUCTURE FOR SITTING HEIGHT DETECTION SENSOR

TECHNICAL FIELD

The present invention relates to an ECU device, a vehicle seat, a system for estimating lower limb length of a seated person, and an attachment structure for a sitting height detection sensor.

BACKGROUND ART

A vehicle seat is being developed so that a position of a seat cushion of the vehicle seat in the front and rear direction, a tilt of the seat cushion, and a length of a sitting surface (hereinafter referred to as a state of the vehicle seat) can be automatically adjusted to be in a state optimal to a seated person seated in the vehicle seat.

In order to be able to form the optimal state, it is necessary to detect or estimate at least a length of a lower limb of the seated person as accurately as possible.

For example, patent document 1 describes when the position of the seat cushion in the front and rear direction is adjusted, the seat cushion is moved forward or backward so that positions of shoulders of the seated person does not move to the front or the rear and a floor surface where heels of the seated person is placed is slightly raised or lowered.

CITATION LIST

Patent Literature

Patent Document 1: JP 2006-290099 A

SUMMARY OF INVENTION

Technical Problem

According to the technique described in patent document 1, the average length of the lower limb of an adult male is considered to be 970 mm and the average length of the lower limb of an adult female is considered to be 900 mm, and a back knee angle, etc. of a seated person sitting in a vehicle seat is estimated based on the above.

However, a physique and skeleton of the seated person are different. Therefore, the state of the vehicle seat adjusted as described above may not be the optimal state to the seated person.

In order to automatically adjust the state of the vehicle seat to the optimal state for the seated person, information of the length of the lower limb of the seated person estimated as accurately as possible becomes necessary, and the automatic adjustment needs to be performed based on the above.

The present invention is conceived in view of the above situation, and the purpose of the present invention is to provide an ECU device which can accurately estimate a lower limb length of the seated person seated in a vehicle seat, a vehicle seat, a system for estimating a lower limb length of a seated person, and an attachment structure for a sitting height detection sensor.

Solution to Problem

In order to solve the above problems, according to aspect 1 of the present invention, an ECU device which estimates a length of a lower limb of a seated person who is seated in a vehicle seat, the ECU device including: a thigh angle information obtainer which obtains information regarding a thigh angle of the seated person; a back knee angle information obtainer which obtains information regarding a back knee angle of the seated person; an estimator which estimates the length of the lower limb of the seated person based on the information regarding the thigh angle obtained by the thigh angle information obtainer and information regarding the back knee angle obtained by the back knee angle information obtainer.

According to aspect 2 of the present invention, in the ECU device according to aspect 1, the thigh angle information obtainer obtains sitting pressure measured by a sitting pressure sensor positioned in a seat cushion of the vehicle seat as the information regarding the thigh angle.

According to aspect 3 of the present invention, in the ECU device according to aspect 2, the seat cushion includes a seat frame, a cushion pad, and an outer layer, and the sitting pressure sensor is positioned in a position avoiding a concave provided in the cushion pad of the seat cushion.

According to aspect 4 of the present invention, in the ECU device according to aspect 1, the back knee angle information obtainer obtains as the information regarding the back knee angle whether pressure is detected by a pressure sensor positioned in a front edge of a seat cushion of the vehicle seat in which the front edge can move in a front and rear direction of the vehicle seat and a moving distance of the front edge.

According to aspect 5 of the present invention, in the ECU device according to aspect 1, the back knee angle information obtainer obtains as the information regarding the back knee angle distances to a calf of the seated person measured by a plurality of infrared sensors positioned in a front edge of a seat cushion of the vehicle seat.

According to aspect 6 of the present invention, the ECU device according to aspect 1, the thigh angle information obtainer obtains as the information regarding the thigh angle a first distance to a knee or a shin measured by irradiating an infrared laser from a first infrared sensor to the knee or the shin of the seated person, and the back knee angle information obtainer obtains as the information regarding the back knee angle a second distance to a heel measured by irradiating the infrared laser to the heel of the seated person from a second infrared sensor.

According to aspect 7 of the present invention, a vehicle seat in which the ECU device according to aspect 1 is attached to the seat frame.

According to aspect 8 of the present invention, a system for estimating a lower limb length of a seated person to estimate a length of a lower limb of a seated person seated in the vehicle seat, the system including: a thigh angle information obtainer which obtains information regarding a thigh angle of the seated person; a back knee angle information obtainer which obtains information regarding a back knee angle of the seated person; and an estimator which estimates the length of the lower limb of the seated person based on the information regarding the thigh angle obtained by the thigh angle information obtainer and the information regarding the back knee angle obtained by the back knee angle information obtainer.

According to aspect 9 of the present invention, in an attachment structure for a sitting height detection sensor, in a vehicle seat provided with an ECU device according to aspect 1, a headrest which supports a head of a seated person is supported with a seat back by a headrest pillar, the headrest is able to move up and down with relation to the seat back along the headrest pillar, and a sitting height detection sensor which detects a sitting height of the seated person seated in the seat is supported by the headrest pillar.

According to aspect 10 of the present invention, in the attachment structure for the sitting height detection sensor according to aspect 9, the headrest pillar includes a pair of columns separated between left and right and a horizontal axis placed across upper edges of the pair of columns, and the sitting height detection sensor is positioned in the center of the horizontal axis.

According to aspect 11 of the present invention, in the attachment structure for the sitting height detection sensor according to aspect 9, the sitting height detection sensor includes a sensor main body and a bracket in which the sensor main body is fixed to a front surface, and the bracket is positioned on a front side of the headrest pillar.

According to aspect 12 of the present invention, in the attachment structure for the sitting height detection sensor according to aspect 9, the sitting height detection sensor includes a sensor main body and a bracket in which the sensor main body is fixed to a front surface, and the bracket is positioned on a rear side of the headrest pillar.

According to aspect 13 of the present invention, in the attachment structure for the sitting height detection sensor according to aspect 9, the sitting height detection sensor includes a sub-sensor which detects a tilt of a head of the seated person.

Advantageous Effects of Invention

According to the invention described in aspects 1, 7, and 8, the thigh angle information obtainer obtains information regarding the thigh angle of the seated person, the back knee angle information obtainer obtains information regarding the back knee angle of the seated person, and the estimator estimates the length of the lower limb of the seated person based on the above information. With this, it is possible to accurately estimate the length of the lower limb of the seated person seated in the vehicle seat.

According to the invention described in aspect 2, the sitting pressure measured by the sitting pressure sensor positioned in the upper surface side of the seat cushion of the vehicle seat is used as information regarding the thigh angle. With this, the estimating process of the lower limb length of the seated person can be performed simply and accurately.

According to the invention described in aspect 3, by positioning the sitting pressure sensor avoiding the pulled portion of the seat cushion, the thigh of the seated person accurately comes into contact with the sitting pressure sensor and the sitting pressure can be accurately measured by the sitting pressure sensor.

According to the invention described in aspect 4, as the information regarding the back knee angle, whether the pressure is detected by the pressure sensor positioned at the front edge of the seat cushion of the vehicle seat and the moving distance of the front edge of the seat cushion are used to be able to perform the estimation process of the length of the lower limb of the seated person simply and accurately.

According to the invention described in aspect 5, as the information regarding the back knee angle, the distances to the calf of the seated person measured by a plurality of infrared sensors positioned at the front edge of the seat cushion of the vehicle seat is used to perform the estimation process of the length of the lower limb of the seated person simply and accurately.

According to the invention described in aspect 6, the first distance to the knee or the shin of the seated person measured by the first infrared sensor is used as the information regarding the thigh angle, and the second distance to the heel of the seated person measured by the second infrared sensor is used as the information regarding the back knee angle. With this, the estimation process of the length of the lower limb of the seated person can be performed simply and accurately.

According to the invention described in aspect 9, the sitting height detection sensor which detects the sitting height of the person seated in the seat is supported by the headrest pillar of the headrest which supports the head of the person, and the headrest to which the sitting height detection sensor is attached is moved up and down with relation to the seat back. With this, the sitting height of the person seated in the seat can be detected. That is, a specific attachment structure which enables the detection of the sitting height by the sitting height detection sensor can be provided. Further, the sitting height detection sensor is supported by the headrest pillar and the supporting rigidity of the sitting height detection sensor can be enhanced.

According to the invention described in aspect 10, the sitting height detection sensor is in a position which is high in the headrest, and is positioned in the center. Therefore, it is possible to easily detect the sitting height of the person seated in the seat.

According to the invention described in aspect 11, the bracket is positioned on the front side of the headrest pillar. Therefore, the sensor main body fixed to the front surface of the bracket is positioned close to the head of the person. Therefore, the decrease of accuracy of detecting the sitting height by the sitting height detection sensor is suppressed.

According to the invention described in aspect 12, the bracket is positioned on the rear side of the headrest pillar. Therefore, the sensor main body fixed to the front surface of the bracket is positioned separated from the head of the person. Therefore, the person seated in the seat hardly feels uncomfortable at the head.

According to the invention described in aspect 13, the sitting height detection sensor includes a sub-sensor which detects a tilt of the head of the person. Therefore, the sitting height can be detected even if the head of the person is tilted, and the detection accuracy of the sitting height by the sitting height detection sensor is enhanced.

BRIEF DESCRIPTION OF DRAWINGS

FIG. 15 is a diagram showing a configuration when the length of the lower limb is calculated based on a position of a heel.

FIG. 16 is a diagram showing a configuration when the length of the lower limb is calculated based on a position of a heel.

DESCRIPTION OF EMBODIMENTS

The present embodiment is described below with reference to the drawings. The embodiments below include various limitations technically preferable to implement the embodiment, however, the technical scope of the present invention is not limited by the embodiments described below and the illustrated examples.

Figure 1:
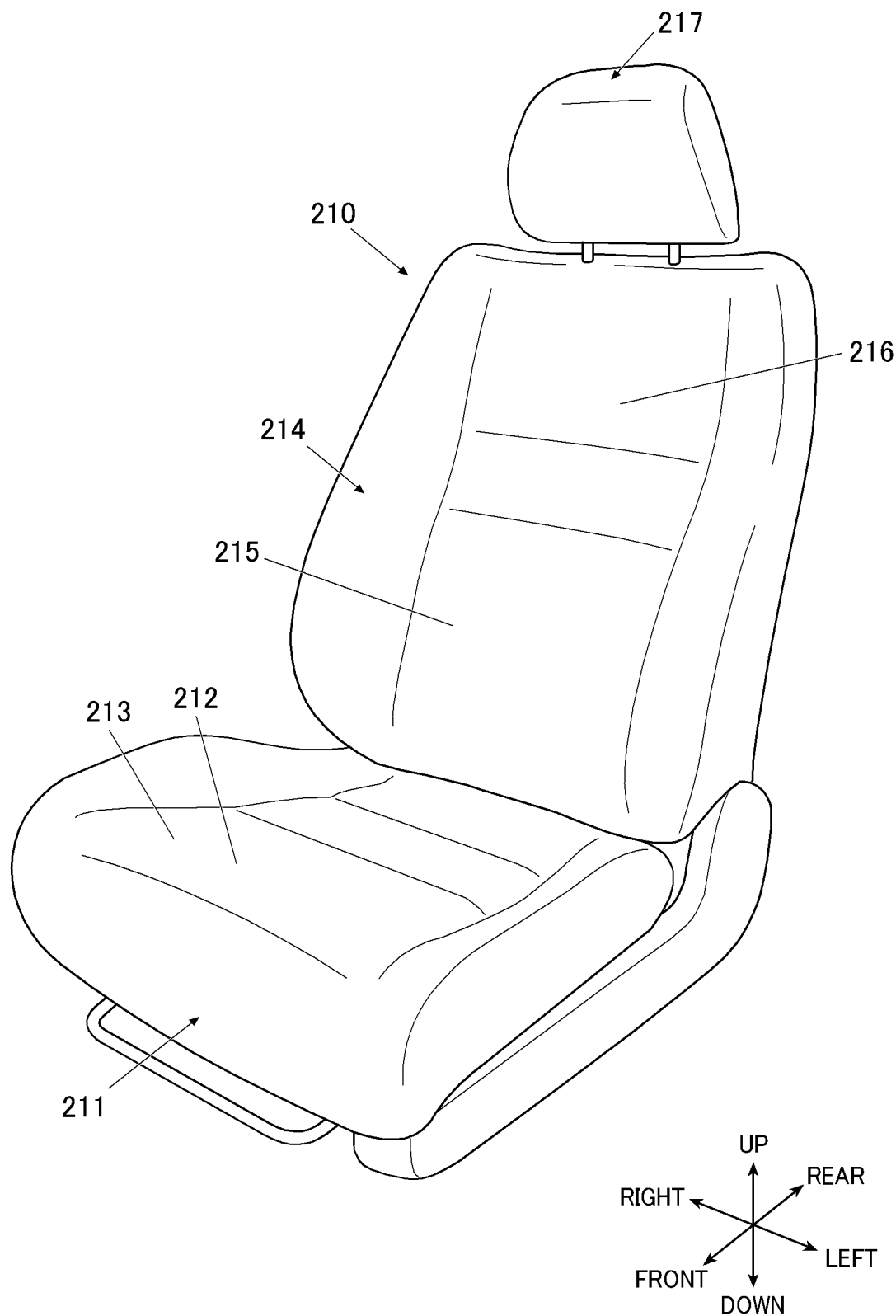
FIG. 1 is a perspective view showing a vehicle seat.

The vehicle seat 210 shown in FIG. 1 is a seat for a vehicle provided in a vehicle such as an automobile. In the description below, the vehicle seat 210 is mainly described as a seat for a driver's seat, but the vehicle seat 210 is not limited to the above. The vehicle seat 210 can be a seat for an occupant's seat, a rear seat for two-row seats, or a second row seat or a third row seat for three-row seats.

As shown in FIG. 1, the vehicle seat 210 includes a seat cushion 211 which supports the buttock and thigh of the seated person, a seat back 214 in which a lower edge is supported by the seat cushion 211 and which is to be a back rest, and a headrest 217 which is provided in the seat back 214 and which supports a head of the seated person. Other than the above, an auxiliary supporter such as a neck rest, an arm rest, a foot rest, an ottoman, and the like can be provided.

The seat cushion 211 mainly includes a seat frame 218 which is to be a skeleton (see later-described FIG. 2), a cushion pad 212 provided on the seat frame 218, and an outer layer 213 which covers the seat frame 218 and the cushion pad 212 and which is included in the surface of the seat.

Similarly, the seat back 214 mainly includes a seat frame 218 which is to be a skeleton (see later-described FIG. 2), a cushion pad 215 provided in the seat frame 218, and an outer layer 216 which covers the seat frame 218 and the cushion pad 215 and which is included in the surface of the seat.

In the vehicle seat 210, a motor which is not shown is driven to be able to move the entire vehicle seat 210 in the front and rear direction, to adjust a height and a tilt (angle of the sitting surface of the seat cushion 211) of the seat cushion 211, to perform the reclining and the middle fold of the seat back 214, and to perform the raising and lowering operation of the headrest 217.

Other than the above, the vehicle seat 210 includes a lumbar support function in which the shape of the seat back 214 placed against the back of the seated person is changed, and a bank portion of the seat cushion 211 and the seat back 214 moves in the up and down direction and the front and rear direction.

Figure 2:
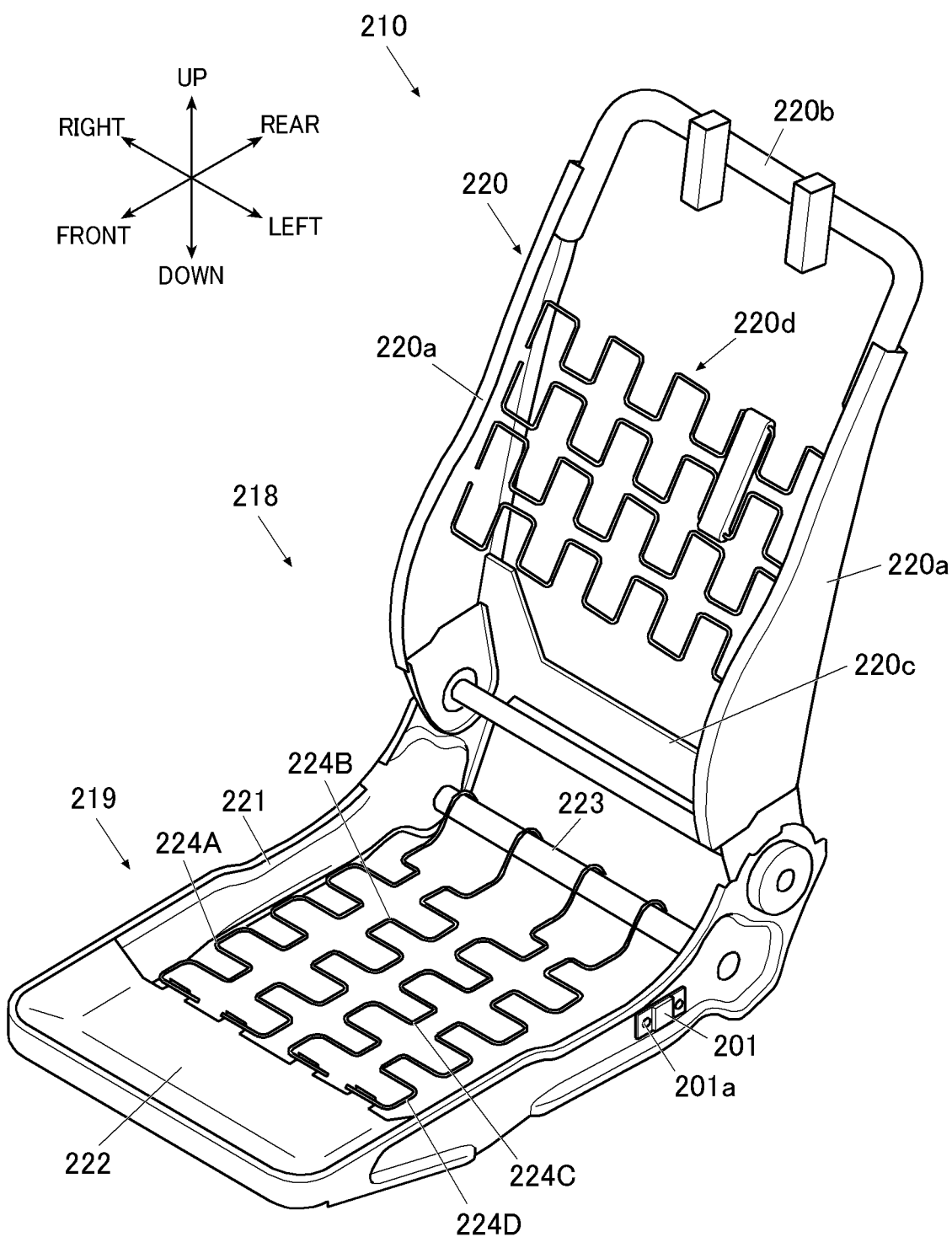
FIG. 2 is a perspective view showing a configuration of a seat frame.

On the lower side of the cushion pad 212 in the seat cushion 211, as shown in FIG. 2, the seat frame 18 (cushion frame, etc.) is provided.

The seat frame 218 includes the seat cushion frame 219 included in the seat cushion 211, and a seat back frame 220 included in the seat back 214.

The seat cushion frame 219 is formed in a frame shape from a plane view and includes a pair of side frames 221 extending to be long in the front and rear direction and separated to the left and the right, a pan frame 222 including sheet metal connecting the front edges of the pair of side frames 221, and a linking pipe 223 including a metal pipe connecting the rear edges of the pair of side frames 221.

A seat spring 224 is provided between the pan frame 222 and the linking pipe 223.

The seat spring 224 includes four spring members 224A to 224D extending to be long in a front and rear direction and aligned in a left and right direction.

In each spring member 224A to 224D, metallic lines are bent to be zigzag in the left and right direction, the rear edge is hooked to the linking pipe 223, and the front edge is linked to the pan frame 222.

The seat back frame 220 includes a pair of side frames 220a which extend to be long in an up and down direction and which are separated in a left and right direction, and an upper frame 220b provided across the upper edges of the pair of side frames 220a, and a plate shaped lower member 220c provided across the lower edges of the pair of side frames 220a.

A seat spring 220d including a plurality of spring members is provided across the pair of side frames 220a between the upper frame 220b and the lower member 220c. The plurality of spring members included in the seat spring 220d extend in the left and right direction and are bent to be zigzag in the up and down direction.

An ECU (Electronic Control Unit) device 201 according to the present invention is attached to the seat frame 218 by screwing with a bolt 1a, for example, in a position not interfering with the operation of members included in the vehicle seat 210.

FIG. 2 shows an example when the ECU device 201 is attached to the outside of the seat frame 218, but the ECU device 201 can be attached to the inside of the seat frame 218. Instead of attaching the ECU device 201 to the seat cushion frame 219, the ECU device 201 can be attached to the seat back frame 220.

FIRST EMBODIMENT

Figure 3:
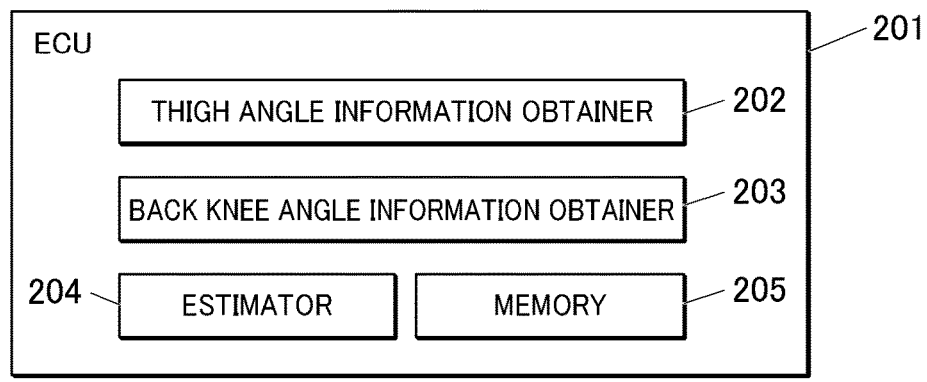
FIG. 3 is a block diagram showing a configuration of an ECU device.

The ECU device 201 is a device to estimate a lower limb length z (length from hip point (hip joint) to heel) of a seated person A seated in the vehicle seat 210. According to the present embodiment, as shown in FIG. 3, the ECU device 201 is provided with a thigh angle information obtainer 202, a back knee angle information obtainer 203, and an estimator 204. Various parameters are stored in the memory 205 of the ECU device 201.

The description regarding the ECU device 201 described below is also the description for the system for estimating the lower limb length of the seated person according to the present invention. Such system includes the thigh angle information obtainer 202, the back knee angle information obtainer 203, and the estimator 204, and the system estimates the length of the lower limb of the seated person seated in the vehicle seat 210.

The thigh angle information obtainer 202 of the ECU device 201 obtains information regarding a thigh angle $\theta$ (angle of a thigh B of the seated person A with relation to a horizontal surface) of the seated person A.

According to the present embodiment, the thigh angle information obtainer 202 obtains sitting pressure measured by a sitting pressure sensor positioned in the seat cushion 211 of the vehicle seat 210 as the information regarding the thigh angle $\theta$.

Figure 4:
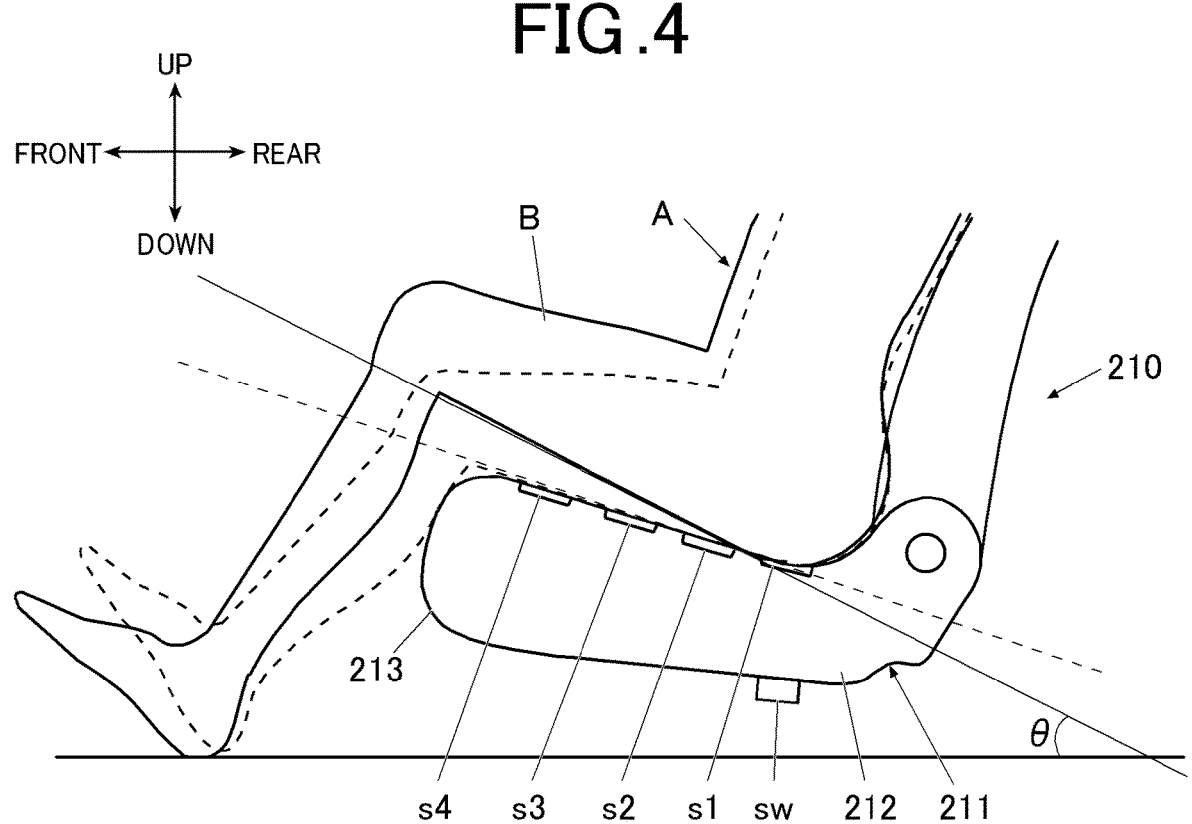
FIG. 4 is a diagram showing positions of sitting pressure sensors on a seat cushion according to the first embodiment.

Described specifically, according to the present embodiment, as shown in FIG. 4, a plurality of sitting pressure sensors s1 to s4 are positioned aligned in the front and rear direction on the upper surface side of the seat cushion 211, that is, between the cushion pad 212 and the outer layer 213 in the seat cushion 211.

The sitting pressure sensors can be positioned between the cushion pad 212 and the outer layer 213 in the seat cushion 211 as shown in FIG. 4. Alternatively, for example, the sitting pressure sensors can be positioned on the lower side of the cushion pad 212 of the seat cushion 211 (for example, upper side of the seat spring 224 and the pan frame 222 (see FIG. 2), etc. that is, between the above and the cushion pad 212) (See for example, JP 2016-144985). For example, the sitting pressure sensors can be embedded in the cushion pad 212 of the seat cushion 211.

Each of the sitting pressure sensors s1 to s4 is electrically connected with the ECU device 201. When the sitting pressure x1 to x4 is measured, each of the measured sitting pressure x1 to x4 is transmitted to the thigh angle information obtainer 202 of the ECU device 201, and the above is received and obtained by the thigh angle information obtainer 202.

Actually, the sitting pressure sensors s1 to s4 are thin and the seated person A does not sense the sitting pressure sensors s1 to s4.

Figure 5:
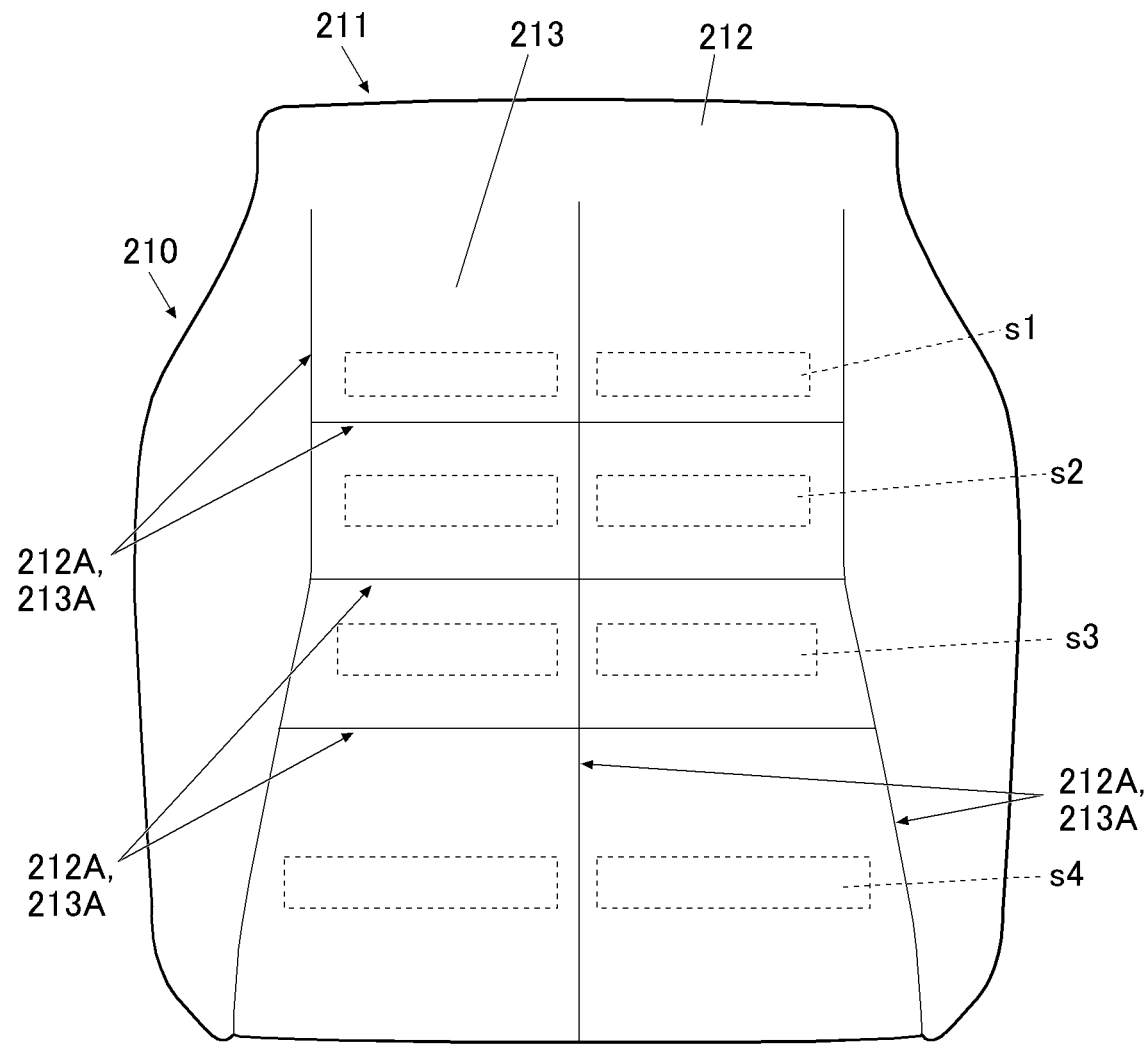
FIG. 5 is a plane view showing the sitting pressure sensors positioned in the positions avoiding grooves provided in a cushion pad in a seat cushion.

A concave 12A such as a groove may be provided in the cushion pad 212 of the seat cushion 211 in the position corresponding to the pulled portion 213A (see FIG. 5) in the outer layer 213. In such case, if the sitting pressure sensors s1 to s4 are provided in the portion of the concave 12A of the cushion pad 212, it becomes difficult for the sitting pressure sensors s1 to s4 to come into contact with the thigh B of the seated person A. Then, there is a possibility that the sitting pressure x cannot be measured accurately. Therefore, as shown in FIG. 5, preferably, the sitting pressure sensors s1 to s4 are positioned in the position avoiding the concave 12A of the cushion pad 212 in the seat cushion 211.

As shown in FIG. 4, according to the present embodiment, a weight detection sensor sw is positioned in the vehicle seat 210 to detect the weight of the seated person A.

The thigh angle information obtainer 202 obtains the weight WT of the seated person A detected by the weight detection sensor sw as a correction value to correct the information regarding the thigh angle θ of the seated person A. When the weight WT of the seated person A becomes heavy, the seated person A sinks deeply in the seat cushion 211, and correction becomes necessary.

The back knee angle information obtainer 203 (see FIG. 3) of the ECU device 201 obtains information regarding the back knee angle φ (angle formed between the thigh and the calf of the seated person A) of the seated person A.

According to the present embodiment, the back knee angle information obtainer 203 obtains as the information regarding the back knee angle φ whether pressure is detected by pressure sensors s11 to s13 positioned at the front edge of the seat cushion 211 in which the front edge is movable in the front and rear direction of the vehicle seat 210 and a distance y of how much the front edge moved.

Figure 6:
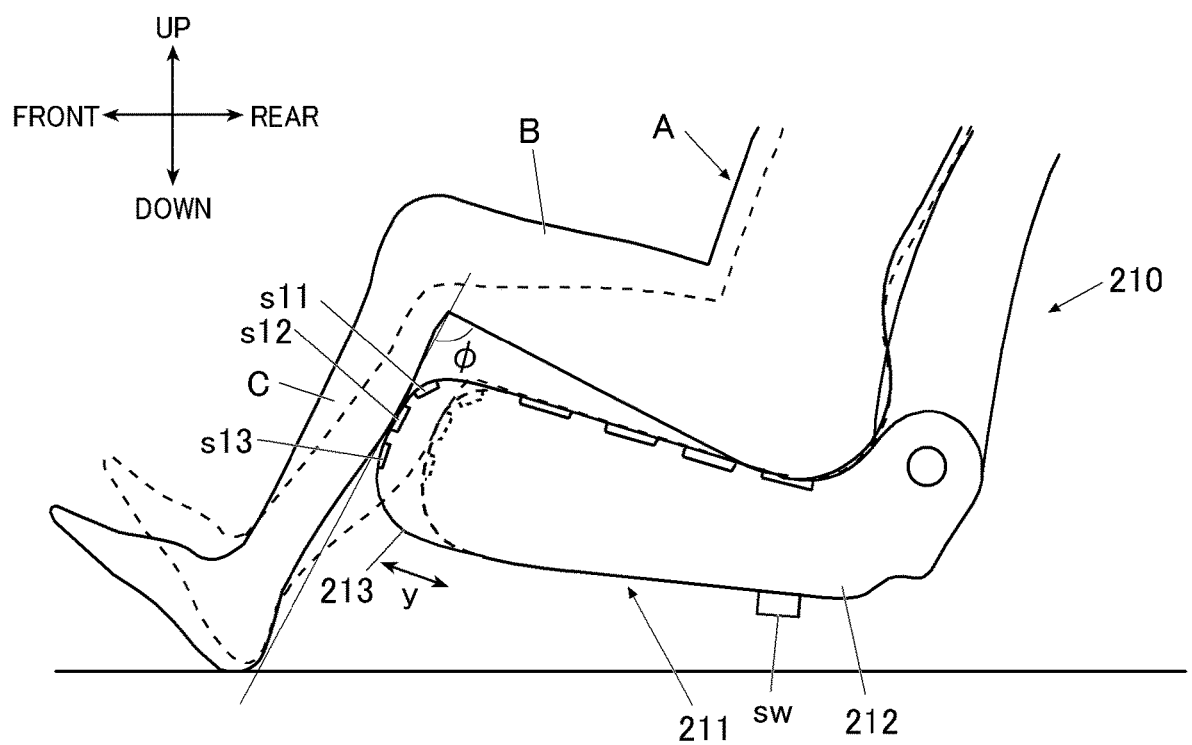
FIG. 6 is a diagram showing positions of the sitting pressure sensors on the seat cushion according to the first embodiment.

Described specifically, according to the present embodiment, as shown in FIG. 6, the plurality of pressure sensors s11 to s13 are positioned aligned in the up and down direction in the front edge of the seat cushion 211 (between the cushion pad 212 and the outer layer 213).

Each of the pressure sensors s11 to s13 are connected electrically to the ECU device 201, and when the pressure is detected, an on signal is output.

According to the present embodiment, the front edge of the seat cushion 211 moves in the front and rear direction of the vehicle seat 210. The information of the moving distance y showing the distance that the front edge of the seat cushion 211 moved forward until the front edge came into contact with the calf C of the seated person A is transmitted to the back knee angle information obtainer 203 of the ECU device 201.

With this, the back knee angle information obtainer 203 receives and obtains the on signal from the pressure sensors s11 to s13 (that, is whether the pressure is detected by the pressure sensors s1 to s13) and the moving distance y as the information regarding the back knee angle φ.

Here, an example of the configuration to move the front edge of the seat cushion 211 in the front and rear direction of the vehicle seat 210 is described. The above configuration is described in JP 2017-30611, and this is to be referred for details.

Figure 7A:
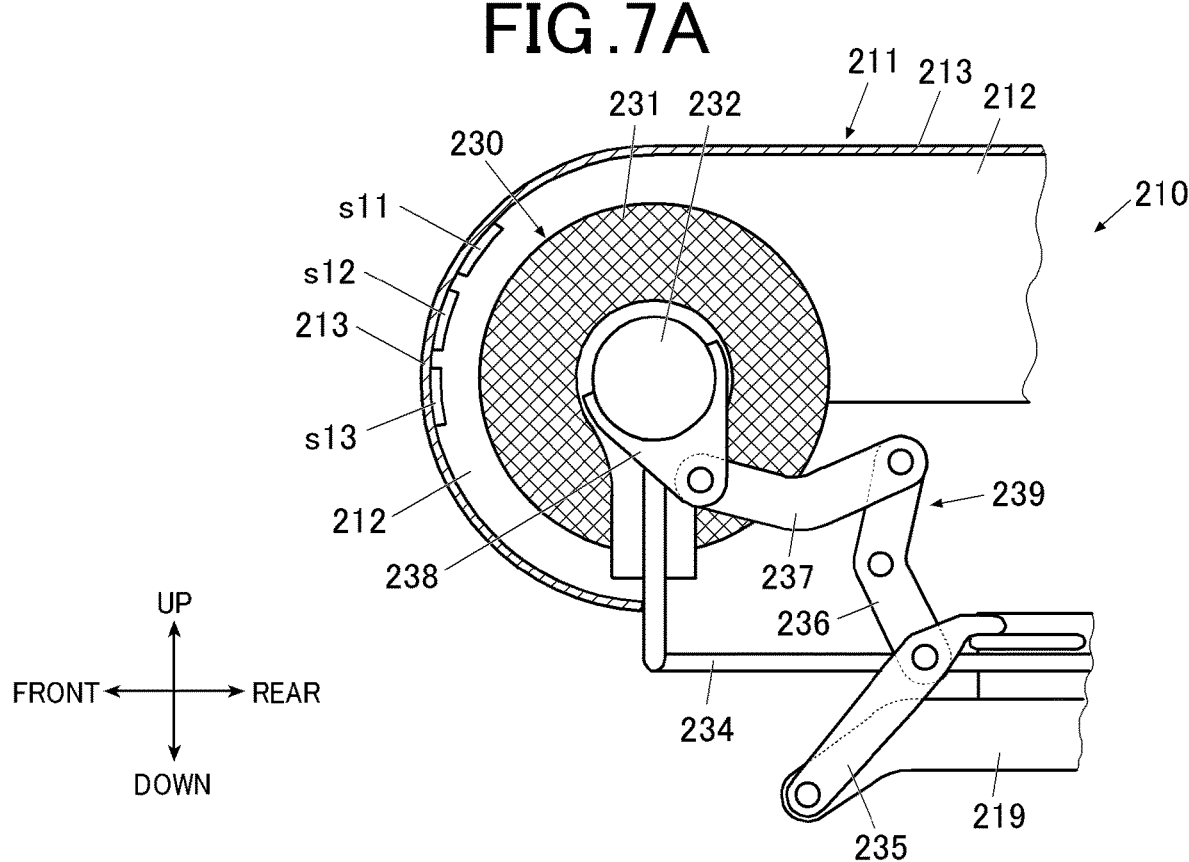
FIG. 7A is a diagram showing a configuration example to move a front edge of a seat cushion in a front and rear direction.
Figure 7B:
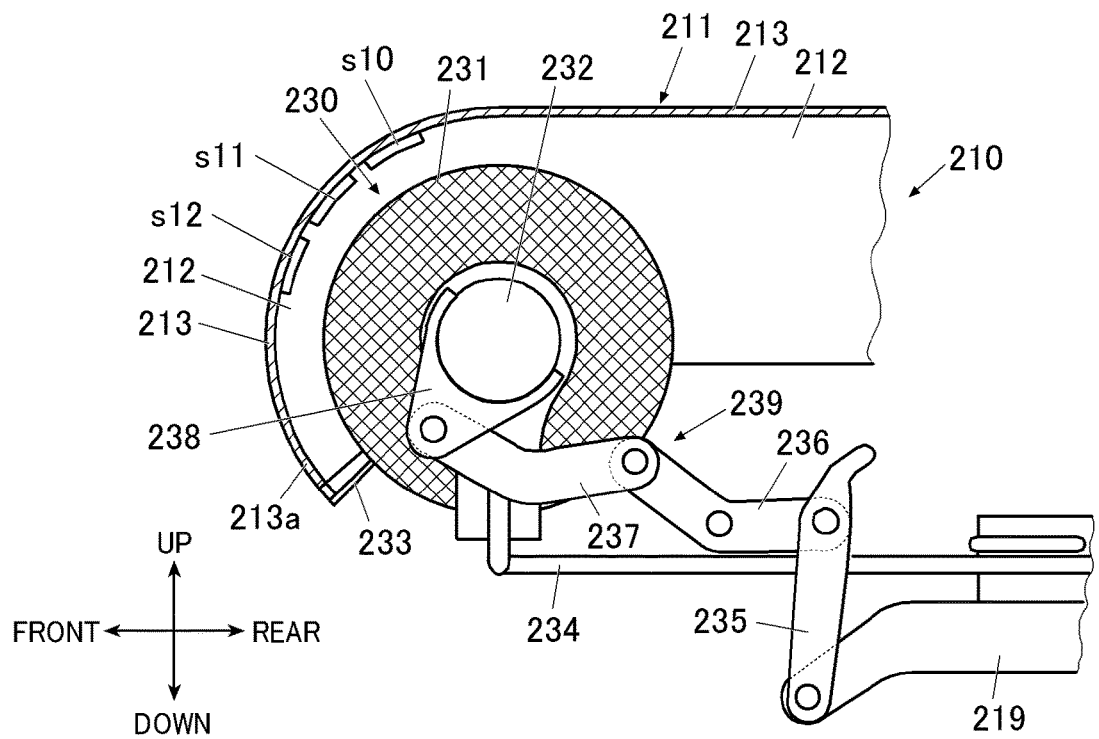
FIG. 7B is a diagram showing a state in which the front edge of the seat cushion is moved to the front.

According to this configuration, as shown in FIG. 7A and FIG. 7B, a roller 230 is positioned to the front side than the front edge of the above-described seat cushion frame 219 (see FIG. 2), and the roller 230 is moved in the front and rear direction to move the front edge of the seat cushion 211 in the front and rear direction.

Specifically, the cushion pad 212 and the outer layer 213 of the seat cushion 211 wrap around the outer circumference 231 of the roller 230, and an edge portion 213a of the outer layer 213 is fixed with a fixer 233 provided in a rotating axis 232. The rotating axis 232 of the roller 230 extends in the left and right direction, and is rotatably supported by a supporter 234. The supporter 234 is positioned to be able to move in the front and rear direction along the seat cushion frame 219 when a driving motor (not shown) is operated.

The front edge portion of the seat cushion frame 219 and the rotating axis 232 of the roller 230 are connected by a link mechanism 239 including a first link 35, a second link 36, a third link 37, and a fourth link 38.

According to such configuration, when the driving motor moves, the supporter 234 moves toward the front and interlocked with the above, the link mechanism 239 rotates the rotating axis 232 of the roller 230. Therefore, a portion of the cushion pad 212 and the outer layer 213 in the seat cushion 211 wrapped around the roller 230 is extended (that is, straight), and the front edge of the seat cushion 211 moves forward.

If the driving motor is operated in the opposite direction, then the supporter 234 moves toward the rear and interlocked with the above, the link mechanism 239 rotates the rotation of the rotating axis 232 of the roller 230 in the opposite rotation. Therefore, as described above, an extended portion of the cushion pad 212 and the outer layer 213 in the seat cushion 211 is wrapped around the roller 230 again, and the front edge of the seat cushion 211 moves to the rear.

As described above, the front edge of the seat cushion 211 is able to move in the front and rear direction. When the roller 230 and the supporter 234 are moved, the moving distance y is measured by the motor driver (not shown) of the driving motor, and the information is transmitted to the back knee angle information obtainer 203 of the ECU device 201.

The configuration to move the front edge of the seat cushion 211 in the front and rear direction of the vehicle seat 210 is not limited to the above configuration. Although illustration is omitted, for example, a portion of the cushion pad 212 of the seat cushion 211 can be moved parallel in the front and rear direction.

The estimator 204 (see FIG. 3) of the ECU device 201 estimates a length z of the lower limb of the seated person A based on the information regarding the thigh angle θ obtained by the above-described thigh angle information obtainer 202 (that is, the sitting pressure x1 to x4 measured by the sitting pressure sensors s1 to s4 and the weight WT of the seated person A detected by the weight detection sensor sw) and the information regarding the back knee angle φ obtained by the back knee angle information obtainer 203 (that is, whether there is detection of pressure by the pressure sensors s11 to s13 and the moving distance y measured by the motor driver).

Figure 8:
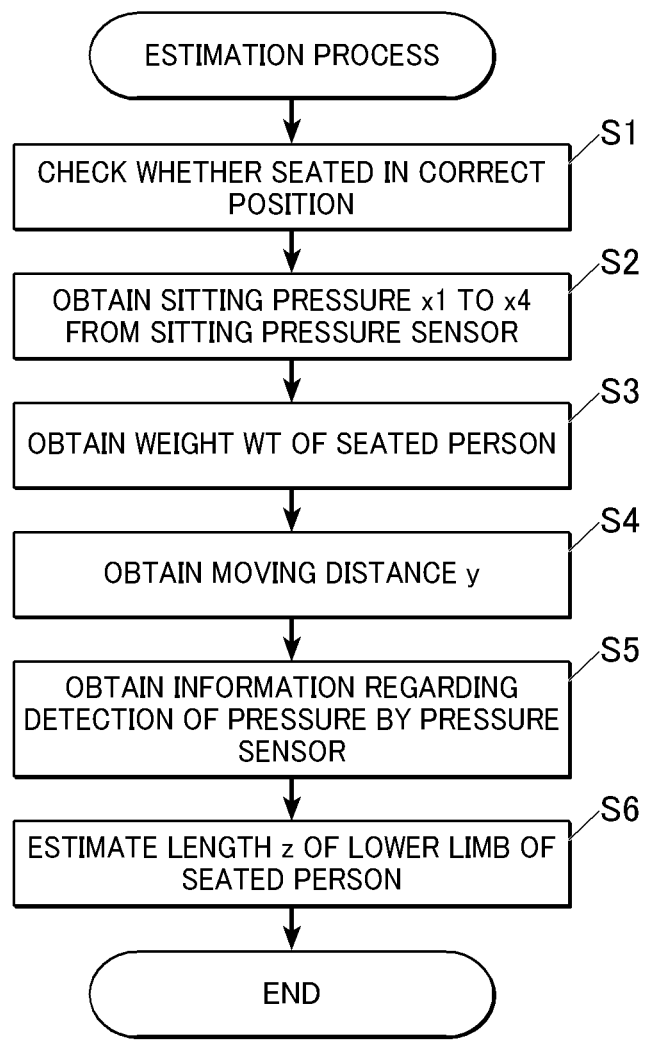
FIG. 8 is a flowchart showing a flow of a process according to a first embodiment.

Below, the estimating process by the estimator 204 to estimate the length z of the lower limb of the seated person A is described in detail along the flow of the actual process as shown in FIG. 8.

First, the ECU device 201 performs an initial operation such as setting each portion of the vehicle seat 210 to the initial state in a state in which the seated person A is not sitting in the vehicle seat 210.

That is, the motors provided in the vehicle seat 210 is driven to move the position of the entire vehicle seat 210 to the initial position in the front and rear direction and to set the height and the tilt of the seat cushion 211, and the reclining state of the seat back 214 in the initial state. The process to move the position of the front edge of the seat cushion 211 to the initial position is also performed.

Then, when the seated person A sits in the vehicle seat 210 in the above state, the ECU device 201 checks whether the lower back of the seated person A touches the sensor (not shown) positioned in the lower portion of the seat back 214 of the vehicle seat 210, for example (that is, whether the seated person A is seated deeply in the vehicle seat 210) and checks whether the seated person A is sitting in the vehicle seat 210 with the correct posture (step S1).

If the seated person A is not sitting in the vehicle seat 210 with the correct posture, the seated person A is urged to sit in the correct posture by a display on the display (not shown) or by output of sound.

When it is determined that the seated person A is sitting with the correct posture, next, the ECU device 201 starts the sitting pressure sensors s1 to s4 positioned on the upper surface side of the seat cushion 211.

The sitting pressure sensors s1 to s4 each measure the sitting pressure x1 to x4, and transmit the result to the thigh angle information obtainer 202 of the ECU device 201.

As described above, the thigh angle information obtainer 202 obtains the sitting pressure x1 to x4 from the sitting pressure sensors s1 to s4 as the information regarding the thigh angle θ (step S2).

As shown in FIG. 4, when the thigh angle θ is small in the state in which the seated person A is sitting in the vehicle seat 210, as shown with broken lines in FIG. 4, not only the side closer to the buttock but also the side closer to the knee in the thigh B of the seated person A comes into contact with the seat cushion 211.

Therefore, in this case, the sitting pressure sensors s1 to s4 measure a significant value different from 0 as sitting pressure x1 to x4.

Then, when the length z of the lower limb of the seated person A becomes long, the thigh angle θ becomes large. As the thigh angle θ becomes larger, the sitting pressure x4 measured by the sitting pressure sensor s4 becomes smaller, and when the thigh B of the seated person A does not come into contact with the sitting pressure sensor s4, the sitting pressure sensor s4 does not measure the sitting pressure x4.

When the thigh angle θ becomes larger, the sitting pressure x3 measured by the sitting pressure sensor s3 becomes smaller, and when the thigh B of the seated person A does not come into contact with the sitting pressure sensor s3, the sitting pressure sensor s3 does not measure the sitting pressure x3.

When the thigh angle θ becomes larger, the sitting pressure on the sitting pressure sensor s1 becomes larger, and the sitting pressure x1 measured by the sitting pressure sensor s1 becomes large.

As described above, it is known from the research by the inventors that there is a strong correlation between the size of the thigh angle θ and the sitting pressure x1 to x4 measured by the sitting pressure sensors s1 to s4.

Moreover, there is a strong correlation between the length z of the lower limb of the seated person A sitting in the vehicle seat 210 and the thigh angle θ. Therefore, by using the sitting pressure x1 to x4 measured by the sitting pressure sensors s1 to s4, it is possible to calculate and estimate the length z of the lower limb of the seated person A.

The weight detection sensor sw transmits the detected weight WT of the seated person A and transmits the weight WT to the thigh angle information obtainer 202.

As described above, the thigh angle information obtainer 202 of the ECU device 201 obtains the weight WT of the seated person A as the correction value of the information regarding the thigh angle θ of the seated person A (step S3).

At the same time as the start of the sitting pressure sensors s1 to s4, the ECU device 201 starts the pressure sensors s11 to s13 and the motor driver. The ECU device 201 drives the driving motor and moves the front edge of the seat cushion 211 forward. At the point when the calf C of the seated person A comes into contact with the front edge of the seat cushion 211 moved forward, the driving of the driving motor is stopped and the moving of the seat cushion 211 is stopped. Then, the moving distance y of the front edge of the seat cushion 211 is transmitted to the back knee angle information obtainer 203 of the ECU device 201.

According to the above, the back knee angle information obtainer 203 obtains the moving distance y of the front edge of the seat cushion 211 (step S4).

When the front edge of the seat cushion 211 comes into contact with the calf C of the seated person A, not all of the pressure sensors s11 to s13 detect the pressure, and only some of the pressure sensors detect the pressure.

At the point when one of the pressure sensors s11 to s13 outputs the on signal, the driving motor stops the driving of the driving motor and stops moving the front edge of the seat cushion 211 forward.

In this case, when the back knee angle φ of the seated person A is small (that is, knees are standing, see solid line shown in FIG. 6), the pressure sensor s13 positioned in the lowest position comes into contact with the calf C of the seated person A. Therefore, the on signal is output from the pressure sensor s13. When the back knee angle φ of the seated person A is large (that is, the knees are laid, see broken line shown in FIG. 6), the on signal is output from the pressure sensor s11 positioned in the highest position. When the back knee angle φ of the seated person A is an angle between the above, the on signal is output from the pressure sensor s12 positioned in the middle position.

When the back knee angle φ of the seated person A is large (that is, the knee is laid), even if the front edge of the seat cushion 211 is moved forward in the maximum amount, the front edge of the seat cushion 211 does not come into contact with the calf C of the seated person A, and none of the pressure sensors s11 to s13 may detect pressure.

According to the research by the inventors, including when none of the pressure sensors s11 to s13 detect pressure, it is known that there is a strong correlation between the size of the back knee angle φ of the seated person A and which of the pressure sensors s11 to s13 detects pressure (that is, whether the pressure sensors s11 to s13 detect pressure).

There is also a strong correlation between the length z of the lower limb of the seated person A sitting in the vehicle seat 210 and the back knee angle φ. Therefore, it is possible to calculate and estimate the length z of the lower limb of the seated person A based on which of the pressure sensors s11 to s13 detected pressure (or none of the pressure sensors s11 to s13 detected pressure).

According to the present embodiment, when the on signal is output from any of the pressure sensors s11 to s13, the back knee angle information obtainer 203 of the ECU device 201 obtains the information of the pressure sensor and when the on signal is not received from any of the pressure sensors s11 to s13 at the point when the moving distance y is obtained from the motor driver, the information that the pressure is not detected by the pressure sensors s11 to s13 is obtained.

In this way, the back knee angle information obtainer 203 obtains the information regarding whether the pressure is detected by the pressure sensors s11 to s13 (step S5).

According to the present embodiment, as the pressure sensors s11 to s13, an example using the sensor which outputs the on signal when the pressure is detected as described above is described. Alternatively, for example, the pressure can be measured with the pressure sensors s11 to s13 and the ECU device 201 can perform the process based on the pressure measured by the pressure sensors s11 to s13.

As described above, the estimator 204 (see FIG. 3) of the ECU device 201 estimates the length z of the lower limb of the seated person A seated in the vehicle seat 210 based on the sitting pressure x1 to x4 of the sitting pressure sensors s1 to s4 and the weight WT of the seated person A obtained by the thigh angle information obtainer 202 and the moving distance y of the front edge of the seat cushion 11 obtained by the back knee angle information obtainer 203 (step S6).

Then, the estimation is made by dividing into cases when the pressure is detected by any of the pressure sensors s11 to s13 or none of the pressure sensors s11 to s13 detected the pressure.

That is, the estimator 204 divides the cases into the following four cases, (a) when the pressure sensor s11 detects the pressure, (b) when the pressure sensor s12 detects the pressure, (c) when the pressure sensor s13 detects the pressure, (d) when none of the pressure sensors s11 to s13 detects the pressure. For each case, the estimator 204 calculates and estimates the length z of the lower limb of the seated person A for each case according to the formula (1) described below.

$$z=(p1\times x1+p2\times x2+p3\times x3+p4\times x4+p5\times WT)\times p6+p7\times y+p8\ldots \quad (1)$$

Here, p1 to p8 are parameters which are set for each case from (a) to (d). That is, for example, if the parameter p1 for cases (a) to (d) is p1$a$, p1$b$, p1$c$, p1$d$, different values are set for parameters p1$a$, p1$b$, p1$c$, p1$d$ (each may be the same value). The same can be said for the other parameters.

The above process is actually performed for a large number of seated persons with various types of physique and skeletons. The obtained data (sitting pressure x1 to x4, weight WT, moving distance y, lower limb length z) is classified divided into the above cases (a) to (d), and the value of each parameter p1 to p8 is set so that the lower limb length z is suitably calculated from the sitting pressure x1 to x4, weight WT, and moving distance y in each case.

Each parameter p1 to p8 set as described above is stored in the memory 205 of the ECU device 201, and is used in the estimating process of the length z of the lower limb of the seated person A.

According to the ECU device 201, the vehicle seat 210, and the system for estimating the length of the lower limb of the seated person according to the present embodiment, the thigh angle information obtainer 202 is configured to obtain the information regarding the thigh angle θ of the seated person A (sitting pressure x1 to x4 and weight WT according to the present embodiment), the back knee angle information obtainer 203 is configured to obtain the information regarding the back knee angle ϕ of the seated person A (whether there is an on signal from the pressure sensors s11 to s13 and the moving distance y of the front edge of the seat cushion 211 according to the present embodiment) and the estimator 204 estimates the length z of the lower limb of the seated person A based on the above information.

Therefore, the length z of the lower limb of the seated person A seated in the vehicle seat 210 can be accurately estimated.

Based on the length z of the lower limb of the seated person A estimated accurately, it is possible to suitably and automatically adjust the position of the entire vehicle seat 210 in the front and rear direction, the position, the height, the tilt of the seat cushion 211, and the length of the sitting surface (that is, the state of the vehicle seat). With this, it is possible to automatically adjust the vehicle seat 210 to an optimal state when the seated person A is seated in the vehicle seat 210.

According to the present embodiment, four rows of the sitting pressure sensors s1 to s4 are provided (see FIG. 4 and FIG. 5) and three rows of the pressure sensors s11 to s13 are provided (see FIG. 6, FIG. 7A, and FIG. 7B). The number of rows of the sitting pressure sensors and the number of rows of the pressure sensors can be increased or decreased. Moreover, the sitting pressure sensor is provided divided into a plurality of sensors (sitting pressure sensors s1 to s4 according to the above embodiment). For example, the sitting pressure can be measured as a surface by a plane shaped sitting pressure sensor.

SECOND EMBODIMENT

According to the first embodiment, the front edge of the seat cushion 211 is actually moved forward and the back knee angle information obtainer 203 of the ECU device 201 is configured to obtain the moving distance y as information regarding the back knee angle ϕ.

Figure 9:
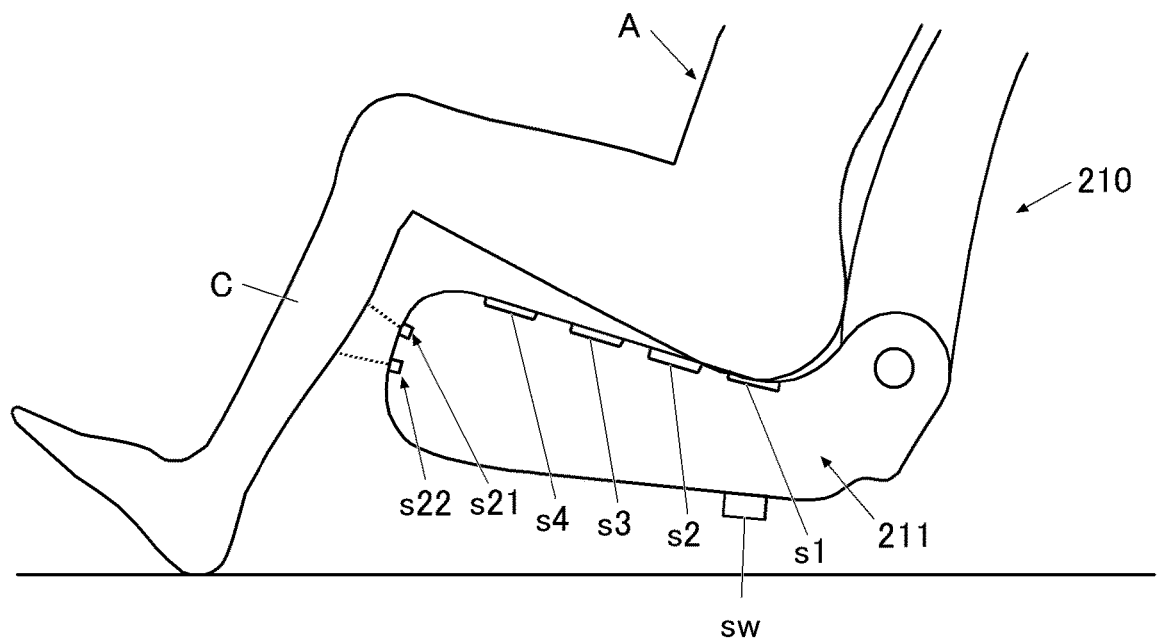
FIG. 9 is a diagram showing a configuration according to a second embodiment.

Instead of such configuration, the following configuration is possible, as shown in FIG. 9, the infrared sensor is positioned in the front edge of the seat cushion 211. An infrared laser is irradiated from the infrared sensor to measure the distance Y to the calf C of the seated person A. The back knee angle information obtainer 203 can be configured to obtain the distance Y as the information regarding the back knee angle ϕ.

In this case, the information regarding the back knee angle ϕ of the seated person A cannot be obtained (that is, the back knee angle ϕ becomes indefinite) by measuring only one point of the distance from the front edge of the seat cushion 211 to the calf C of the seated person A. Therefore, as shown in FIG. 9, a plurality of infrared sensors s21 and s22 are positioned in different positions of the front edge of the seat cushion 211 in the up and down direction, and the distances y21 and y22 to the calf C of the seated person A measured by the plurality of infrared sensors s21 and s22 are obtained.

The number of infrared sensors positioned in the front edge of the seat cushion 211 can be three or more.

Then, in this case, based on the obtained distances y21 and y22, the estimator 204 of the ECU device 201 is able to estimate the length z of the lower limb of the seated person A by dividing the cases similar to the first embodiment.

The estimator 204 may be configured to not divide the cases and may calculate and estimate the length z of the lower limb of the seated person A according to one formula shown as in the formula (2) described below.

$$z=(p1\times x1+p2\times x2+p3\times x3+p4\times x4+p5\times WT)\times p6+p7\times y21+p8\times y22+p9\ldots \quad (2)$$

In this case also, the process is actually performed in advance for a large number of seated persons with various physique and skeleton. The obtained data (sitting pressure x1 to x4, weight WT, distances y21 and y22, and limb length z) is substituted in the above formula (2) and the value of each parameter p1 to p9 is set to suitably calculate the length z of the lower limb from the sitting pressure x1 to x4, the weight WT, and the distances y21 and y22.

The parameters p1 to p9 set as described above are stored in the memory 205 of the ECU device 201, and are used in the process for estimating the length z of the lower limb of the seated person A.

As described above, according to the ECU device 201, the vehicle seat 210, and the system for estimating the length of the lower limb of the seated person according to the present embodiment, the thigh angle information obtainer 202 is configured to obtain the information regarding the thigh angle θ (sitting pressure x1 to x4 and weight WT according to the present embodiment) of the seated person A, the back knee angle information obtainer 203 is configured to obtain the information regarding the back knee angle ϕ of the seated person A (distances y21 and y22), and the estimator 204 estimates the length z of the lower limb of the seated person A based on the above information.

Therefore, the length z of the lower limb of the seated person A seated in the vehicle seat 210 can be accurately estimated.

Based on the length z of the lower limb of the seated person A which is accurately estimated, the position of the entire vehicle seat 210 in the front and rear direction, the position, height, and tilt of the seat cushion 211, and the length of the sitting surface (that is, the state of the vehicle seat) can be suitably and automatically adjusted. With this, it is possible to automatically adjust the vehicle seat 210 to the optimal state when the seated person A is seated.

Third Embodiment

According to the above-described embodiments, it is described that the length z of the lower limb of the seated person A is estimated by obtaining the sitting pressure x1 to x4 measured by the sitting pressure sensors s1 to s4 as the information regarding the thigh angle θ of the seated person A, and obtaining the moving distance y of the front edge of the seat cushion 211 and the distances y21 and y22 measured by the infrared sensors s21 and s22 as the information regarding the back knee angle φ.

Figure 10:
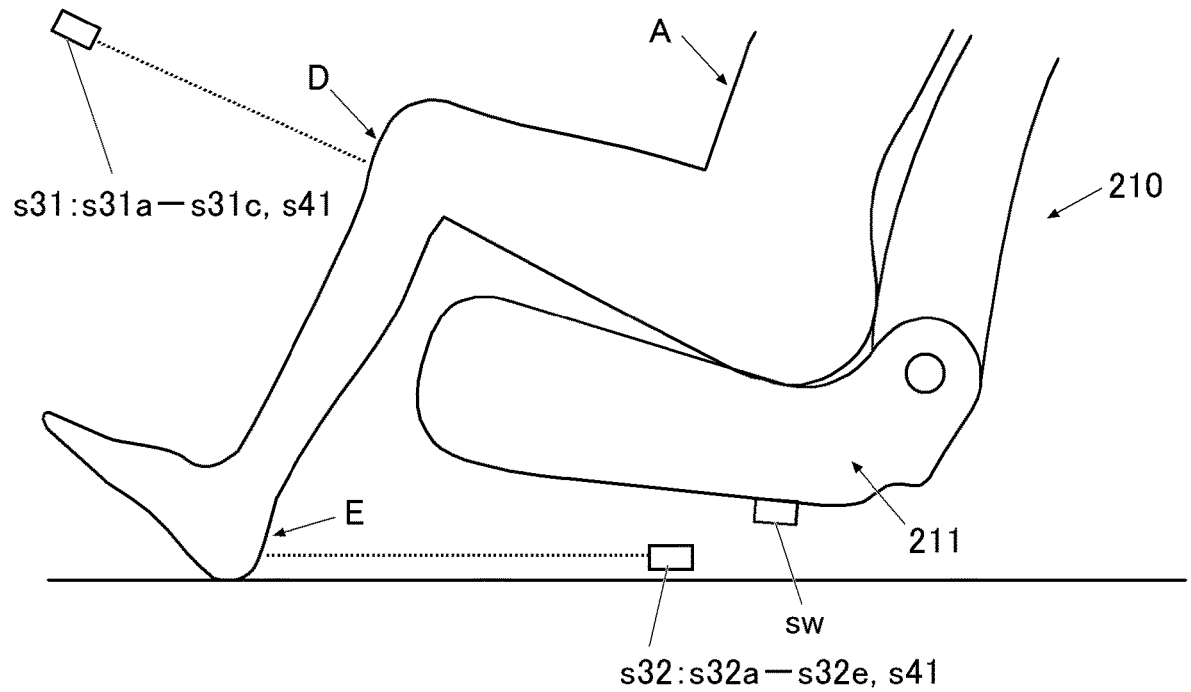
FIG. 10 is a diagram showing a configuration according to a third embodiment.

Instead of such configuration, as shown in FIG. 10, the length z of the lower limb of the seated person A can be estimated based on a first distance Y1 to the knee or the shin D obtained by irradiating an infrared laser toward the knee or the shin D of the seated person A seated in the vehicle seat 210 from the first infrared sensor s31 and a second distance Y2 to the heel E obtained by irradiating the infrared laser toward the heel E of the seated person A from the second infrared sensor s32.

That is, in this case, the thigh angle information obtainer 202 of the ECU device 201 is configured to obtain the first distance Y1 to the knee or the shin D measured by irradiating the infrared laser toward the knee or the shin D of the seated person A from the first infrared sensor s31 as the information regarding the thigh angle θ.

The back knee angle information obtainer 203 of the ECU device 201 is configured to obtain the second distance Y2 to the heel E measured by irradiating the infrared laser toward the heel E of the seated person A from the second infrared sensor s32 as the information regarding the back knee angle φ.

Here, the first infrared sensor s31 is positioned in any position in the vehicle such as the lower side of the steering wheel and the instrument panel (not shown) in the vehicle, for example. The second infrared sensor s32 is positioned in any position in the vehicle such as the lower side of the vehicle seat 210, for example.

Similar to the infrared sensors s21 and s22 according to the second embodiment described above, when the seated person A is seated, the legs may be open or the legs may be closed. Therefore, if one of each of the first infrared sensor s31 and the second infrared sensor s32 is positioned, the irradiated infrared laser may not hit the knee or the shin D or the heel E of the seated person A. Therefore, it may not be possible to measure the first distance Y1 to the knee or the shin D of the seated person A or the second distance Y2 to the heel E.

Therefore, for example, a plurality of first infrared sensors s31 may be positioned aligned in the left and right direction (for example, three first infrared sensors s31a to s31c (see FIG. 10)), and preferably, the infrared lasers are irradiated from the plurality of first infrared sensors s31 parallel to each other with a predetermined space in between.

Similarly for the second infrared sensor s32, for example, a plurality of second infrared sensors s32 may be positioned aligned in the left and right direction (for example, five second infrared sensors s32a to s32e (see FIG. 10)), and preferably, the infrared lasers are irradiated parallel to each other with a predetermined space in between from the plurality of second infrared sensors s32.

According to such configuration, regardless of whether the seated person A is seated with the legs open or the legs closed, the infrared laser irradiated from at least one of the first infrared sensors s31 hits the knee or the shin D of the seated person A, and the first distance Y1 to the knee or the shin D of the seated person A can be reliably measured.

Moreover, the infrared laser irradiated from at least one of the second infrared sensors s32 hits the heel E of the seated person A, and the second distance Y2 to the heel E of the seated person A can be reliably measured.

Figure 11:
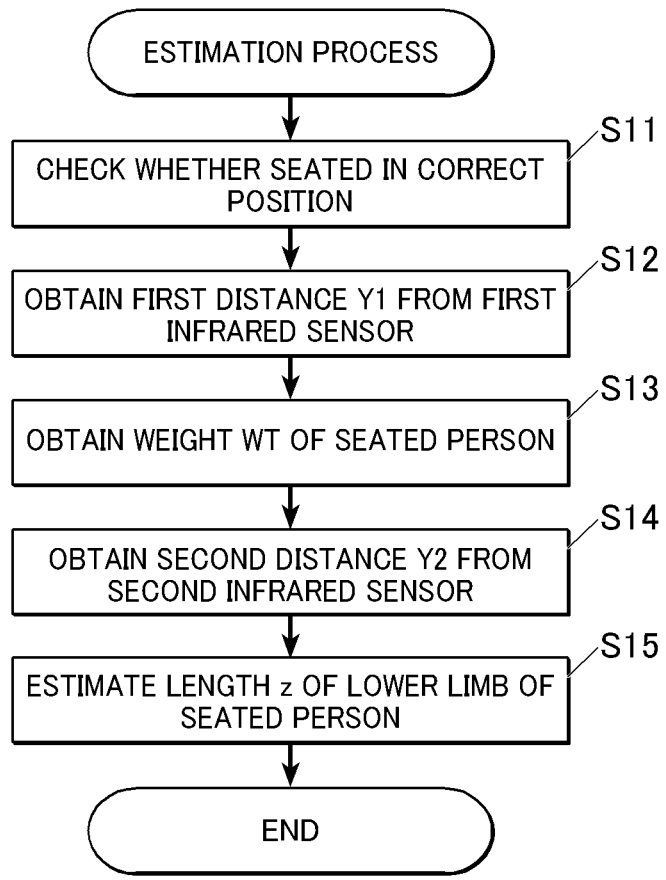
FIG. 11 is a flowchart showing a flow of a process according to the third embodiment.

According to the present embodiment, the estimator 204 of the ECU device 201 is configured to perform the process for estimating the length z of the lower limb of the seated person A according to the flow of the process shown in FIG. 11.

According to the present embodiment, the ECU device 201 performs an initial operation to move the position of the entire vehicle seat 210 to the initial position in the front and rear direction, and to set the height and the tilt of the seat cushion 211 and the reclining of the seat back 214 to the initial state in a state in which the seated person A is not seated in the vehicle seat 210.

Then, when the seated person A sits in the vehicle seat 210 in the above state, the ECU device 201 checks whether the lower back of the seated person A touches the sensor (not shown) positioned in the lower portion of the seat back 214 of the vehicle seat 210, for example (that is, whether the seated person A is seated deeply in the vehicle seat 210) and checks whether the seated person A is sitting in the vehicle seat 210 with the correct posture (step S11).

If the seated person A is not sitting in the vehicle seat 210 with the correct posture, the seated person A is urged to sit with the correct posture by displaying on the display (not shown) or by outputting sound.

When it is determined that the seated person A is sitting with the correct posture, next, the ECU device 201 starts the first infrared sensors s31a to s31c and the second infrared sensors s32a to s32e.

When the first infrared sensors s31a to s31c are started, each of the above irradiates the infrared lasers toward the knee or the shin D of the seated person A, and each of the above transmits the measured first distance Y1 to the thigh angle information obtainer 202 of the ECU device 201 (hereinafter, each of the first distance Y1 measured by the first infrared sensors s31a to s31c is to be referred to as Y1a to Y1c, respectively).

According to the above, the thigh angle information obtainer 202 obtains the first distance Y1 (Y1a to Y1c) as the information regarding the thigh angle θ (step S12).

The weight detection sensor sw transmits the detected weight WT of the seated person A to the thigh angle information obtainer 202.

As described above, the thigh angle information obtainer 202 of the ECU device 201 obtains the weight WT of the seated person A as the correction value of the information regarding the thigh angle θ of the seated person A (step S13).

When the second infrared sensors s32a to s32e are started, each of the above irradiates the infrared lasers toward the heel E of the seated person A, and each of the above transmits the measured second distance Y2 to the back knee angle information obtainer 203 of the ECU device 201 (hereinafter, each of the second distance Y2 measured by the second infrared sensors s32a to s32e is to be referred to as Y2a to Y2e, respectively).

As described above, the back knee angle information obtainer 203 obtains the second distance Y2 (Y2a to Y2e) as the information regarding the back knee angle θ (step S14).

When the infrared laser irradiated from the first infrared sensor s31 and the second infrared sensor s32 is not irradiated to the seated person A (that is, the knee and the shin D and the heel E of the seated person A is not within the irradiating range of the infrared laser), the first distance Y1 and the second distance Y2 is to be infinity (actually, maximum value of the value which the first distance Y1 and the second distance Y2 can be).

As described above, the estimator 204 of the ECU device 201 estimates the length z of the lower limb of the seated person A seated in the vehicle seat 210 based on the first distance Y1 and the weight WT of the seated person A obtained by the thigh angle information obtainer 202 and the second distance Y2 obtained by the back knee angle information obtainer 203 (step S15).

Specifically, the estimator 204 extracts the minimum value from the first distances Y1a to Y1c measured by the first infrared sensors s31a to s31c and sets this as the first distance Y1. Similarly, the minimum value is extracted from the second distances Y2a to Y2e measured by the second infrared sensors s32a to s32e and this is set as the second distance Y2.

The estimator 204 calculates and estimates the length z of the lower limb of the seated person A according to the following formula (3).

$$z = p11 \times Y1 + p12 \times Y2 + p13 \times WT + p14 \ldots \quad (3)$$

Here, p11 to p14 are parameters, and the values of the parameters p11 to p14 are set so that the length z of the lower limb is suitably calculated from the first distance Y1, the second distance Y2, and the weight WT by actually performing the above process in advance for a large number of seated persons with various types of physique and skeleton, and applying the obtained data (first distance Y1, second distance Y2, weight WT, and lower limb length z) to the formula (3).

The parameters p11 to p14 set as described above are stored in the memory 205 of the ECU device 201, and are used for the process for estimating the length z of the lower limb of the seated person A.

As described above, according to the ECU device 201 of the present embodiment, the vehicle seat 210, and the system for estimating the length of the lower limb of the seated person, the thigh angle information obtainer 202 is configured to obtain information regarding the thigh angle θ of the seated person A (first distance Y1 according to the present embodiment), the back knee angle information obtainer 203 is configured to obtain the information regarding the back knee angle θ of the seated person A (second distance Y2 according to the present embodiment), and the estimator 204 estimates the length z of the lower limb of the seated person A based on the above information.

Therefore, the length z of the lower limb of the seated person A seated in the vehicle seat 210 can be accurately estimated.

Based on the length z of the lower limb of the seated person A estimated accurately, the position of the entire vehicle seat 210 in the front and rear direction, the position, height and tilt of the seat cushion 211, and the length of the sitting surface (that is, the state of the vehicle seat) can be suitably and automatically adjusted, and the vehicle seat 210 can be automatically adjusted to be the optimal state when the seated person A is seated.

According to the present embodiment, other than the first distance Y1 or the second distance Y2 to the knee or the shin D or the heel E of the seated person A measured by the first infrared sensor s31 or the second infrared sensor s32, the distance to any portion of the body of the seated person A can be measured, and the distance can be used when the length z of the lower limb of the seated person A is estimated to enhance the accuracy of the estimate of the length z of the lower limb of the seated person A.

The present invention is not limited to the above embodiments, and various changes are possible without leaving the scope of the present invention.

[Modification]

The embodiments in which the present invention can be applied is not limited to the above-described embodiments, and various changes are possible without leaving the scope of the present invention. Modifications are described below. The modifications below can be combined if possible.

[Modification 1]

According to the present modification, as shown in FIG. 4 to FIG. 7A and FIG. 7B, the size of the thigh angle θ is estimated based on the balance of the sitting pressure x1 to x4 measured by the plurality of sitting pressure sensors s1 to s4 provided aligned in the front and rear direction on the upper surface side of the seat cushion 111.

Figure 12:
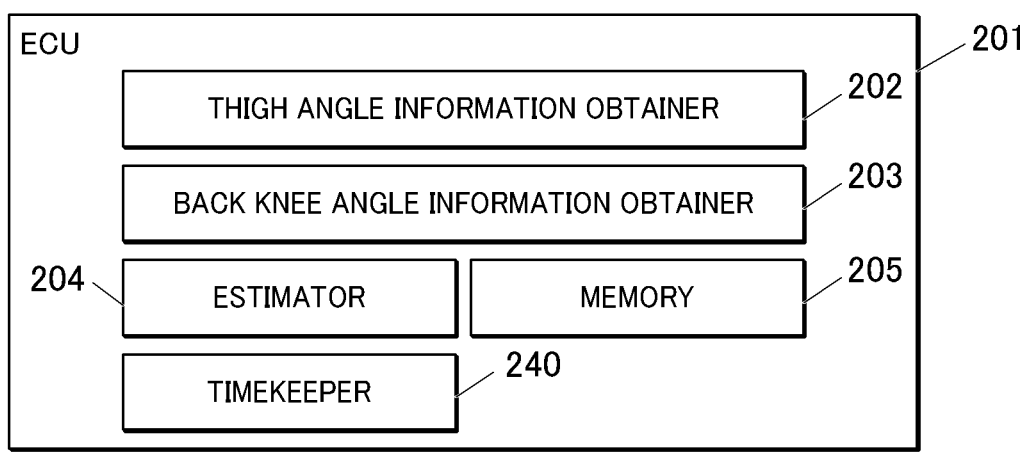
FIG. 12 is a block diagram showing a modification of a configuration of an ECU device.

In addition to the above, according to the present modification, as shown in FIG. 12, the ECU device 201 includes a timekeeper 240 which measures the time, and the position of the calf C is estimated based on the pressure detected by the pressure sensors s11 to s13 provided on the front edge of the seat cushion 211 which moves in the front and rear direction of the vehicle seat 210 and contact time in which the seated person A came into contact with the front edge of the seat cushion 211.

That is, since the plurality of seating pressure sensors s1 to s4 are aligned in the front and rear direction, there is a difference in the strength of the sitting pressure x1 to x4 measured by the sitting pressure sensors s1 to s4 depending on the size of the thigh angle θ. That is, as for a person with the length z of the lower limb being long, the sitting pressure becomes weaker toward the front edge of the seat cushion 11 (sitting pressure is not applied if there is no contact). The ECU device 201 estimates the size of the thigh angle θ of the seated person A based on strong/weak balance of the pressure. Therefore, as long as the seated person A is seated in the correct posture, the thigh angle information obtainer 202 is able to obtain the information regarding the thigh angle θ.

If the front edge of the seat cushion 211 is moved and comes into contact with the calf C, the contact with the calf C can be detected by any of the pressure sensors among the pressure sensors s11 to s13 provided in the front edge of the seat cushion 211. Here, depending on the size of the back knee angle φ, one or two of the pressure sensors among the three pressure sensors s11 to s13 do not come into contact with the calf C. That is, there are a plurality of patterns of detecting the position of the calf C with any of the three pressure sensors s11 to s13 depending on the size of the back knee angle φ. In other words, the ECU device 201 moves the front edge of the seat cushion so as to come into contact with the calf C, specifies the pressure sensor s11 to s13 which detects the calf C and estimates the back knee angle φ based on the result. Therefore, as long as the seated person A is seated with the correct posture, the back knee angle information obtainer 203 is able to obtain information regarding the back knee angle φ.

As described above, the estimator 204 of the ECU device 201 estimates the length z of the lower limb of the seated person A based on the information regarding the thigh angle θ obtained by the thigh angle information obtainer 202 (that is, the sitting pressure x1 to x4 measured by the sitting pressure sensors s1 to s4 and the weight WT of the seated person A detected by the weight detection sensor sw), the position of the calf C, and the information regarding the back knee angle φ obtained by the back knee angle information obtainer 203 (that is, whether the pressure is detected by the pressure sensors s11 to s13).

With this, the length z of the lower limb of the seated person A seated in the vehicle seat 210 can be estimated more accurately.

[Modification 2]

According to the modification, for example, an ultrasound sensor s41 is positioned in the position of the first infrared sensor s31 (s31a to s31c) and the second infrared sensor s32 (s32a to s32e) referred in FIG. 10. The ultrasound sensor s41 emits ultrasound to the target with a wave transmitter, and the reflected wave is received by the wave receiver. With this, whether the target exists and the distance to the target is detected. According to the modification, the shin D (including knee) and the heel E of the seated person A are the targets.

Only one ultrasound sensor s41 may be provided or a plurality of the above may be provided.

The angle of the ultrasound sensor s41 can be suitably adjusted according to the control by the ECU device 201.

According to the ultrasound sensor s41 set as described above, the distance from the knee to the heel E of the seated person A can be measured, and the ECU device 201 calculates the length z of the lower limb of the seated person based on the measured result.

The position where the ultrasound sensor s41 is provided can be a position which can emit ultrasound from the side of the seated person A (left and right direction of the vehicle). With this, the length z of the lower limb can be directly obtained.

According to the present modification, if the seated person A is seated in the correct posture, by using the ultrasound sensor s41, the length z of the lower limb of the seated person A can be calculated easily.

[Modification 3]

Figure 13:
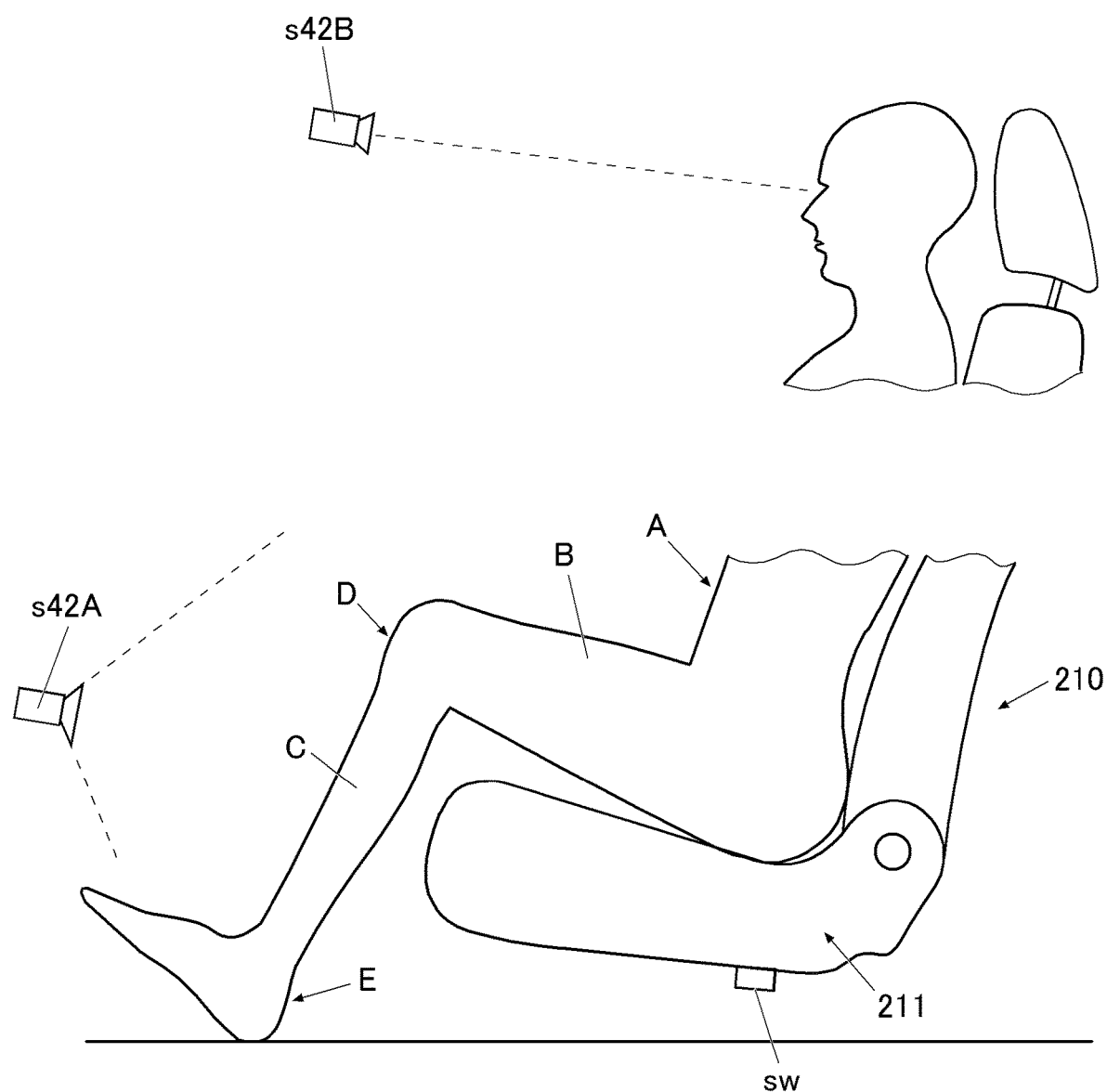
FIG. 13 is a diagram showing an example when a sensor different from the present embodiment is used.

According to the present modification, as shown in FIG. 13, a first camera s42A is positioned below the steering wheel of the vehicle setting the lower limb (leg including thigh B, shin D, and heel E) of the seated person A as an imaging target (subject), and a second camera s42B is positioned in a position above the steering wheel setting a face of the seated person A (eye or top of head) as the imaging target.

The position of the first camera s42A is preferably a position which is able to include the entire lower limb of the seated person A in the imaging range.

Further, the number of the first camera s42A and the second camera s42B may be only one or a plurality may be provided.

The angle of the first camera s42A and the second camera s42B may be adjusted suitably according to control by the ECU device 201.

The information obtained by the first camera 42A can measure the position of the leg (at least including from the thigh B to the heel E), the state of the leg (thigh angle θ and back knee angle φ), and length from hip point to heel E, that is, the length z of the lower limb.

Further, according to the second camera s42B, the height of the eye of the seated person A (eye point) and the height of the top of the head can be understood, and the sitting height of the seated person A can be estimated based on the above.

As long as the seated person A is seated in the correct posture, the length z of the lower limb of the seated person A (length from the hip point (thigh joint) to the heel) can be easily estimated by imaging the lower leg with the first camera s42A, and the sitting height of the seated person A can be estimated by imaging the face with the second camera s42B. With this, when the positions of the units of the vehicle seat 210 can be adjusted automatically by the control of the ECU device 201, the units of the vehicle seat 210 can be automatically adjusted to the optimal positions for driving based on the imaging result by the first camera s42A and the second camera s42B.

The cameras s42A and s42B are fixed in the setting position with relation to the vehicle, and the variation of the distance to the lower limb as the subject is small as long as the seated person A is seated with the correct posture (fixed point measurement is possible). Therefore, the length z of the lower limb of the seated person A can be easily estimated even with the cameras s42A and s42B.

[Modification 4]

According to the present modification, the ECU device 201 estimates the length z of the lower limb of the seated person A based on the height information of the seated person A and the detection results of the sitting height.

Figure 14:
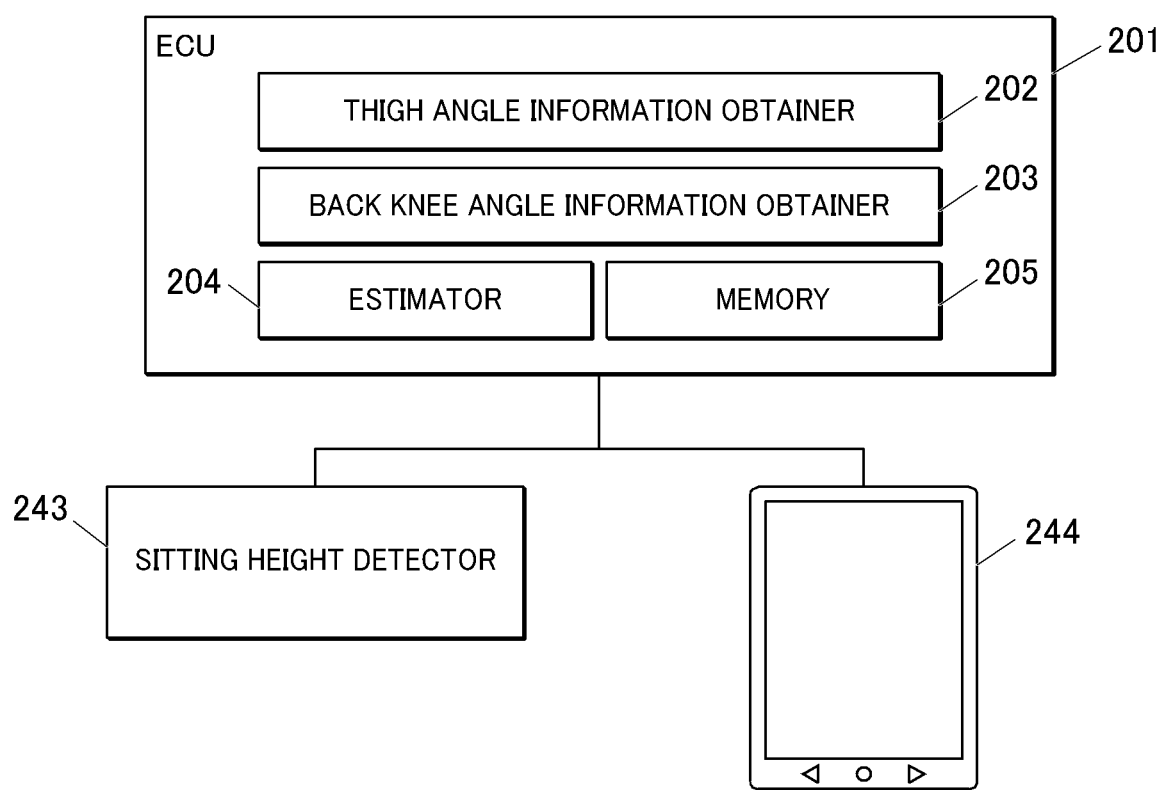
FIG. 14 is a block diagram showing a system configuration in which a length of a lower limb is calculated with a method different from the present embodiment.

As shown in FIG. 14, a sitting height detector 243 and an information terminal such as a tablet terminal and a smartphone are connected to the ECU device 201 to be able to communicate with each other. That is, the information can be transmitted and received between the ECU device 201 and the sitting height detector 243, and the information can be transmitted and received between the ECU device 201 and the information terminal 244 also.

The connection of the ECU device 201 with the sitting height detector 243 and the information terminal 244 can be wired or wireless. Short-range wireless communication such as Bluetooth (Registered Trademark) can be used or various computer networks can be used.

The sitting height detector 243 is not limited as long as the sitting height of the seated person A seated in the vehicle seat 210 can be detected. According to the present modification, the sitting height detector 243 includes a position sensor which detects a position of the target (for example, infrared sensor, ultrasound sensor, electromagnetic wave sensor, laser range finder, etc.) and a mechanism to adjust the position of the sensor according to necessity.

Described in detail, for example, the position sensor is provided in the headrest 217, and the mechanism to move the headrest 217 up and down is provided in the seat back 214. The headrest 217 is moved up and down according to control by the ECU device 201 to detect the position of the head of the seated person A and the sitting height of the seated person A can be detected. The method is not limited to the above and the method can be suitably changed.

The height information is input from the information terminal 244.

The ECU device 201 calculates the length z of the lower limb of the seated person A based on the height information input on the information terminal 244 and the detection result of the sitting height by the sitting height detector 243.

Here, the size around the hip can be input on the information terminal 244 as the information of the correction value to consider the roundness of the buttock. The weight WT detected by the weight detection sensor sw can be the correction value.

According to the modification, based on the height information of the seated person A and the detection result of the sitting height, the length z of the lower limb of the seated person A can be easily estimated.

[Modification 5]

According to the present modification, the heel E is to be positioned in the specified position, and the ECU device 201 estimates the length z of the lower limb of the seated person A based on the balance of the sitting pressure x1 to x4 measured by the plurality of sitting pressure sensors s1 to s4.

The specified position is shown so that the seated person A can easily understand the position, for example, by providing a marking on an upper surface of a floor mat 245 (see FIG. 15) to notify the position to place the heel E.

By specifying the position of the heel E even if the seated person A changes to a different person, the position of the heel E can be set under the same conditions. The information regarding the thigh angle θ can be estimated from the balance of the sitting pressure x1 to x4 measured by the plurality of sitting pressure sensors s1 to s4, and the length z of the lower limb of the seated person A can be calculated.

As shown in FIG. 15, a floor pressure sensor 246 can be provided on the rear side of the floor mat 245 and the position of the heel E of the seated person A can be detected. If the position of the heel E can be detected, for example, the length z of the lower limb can be calculated for the person who cannot place the heel E in the position of the marking as described above. That is, the length z of the lower limb of the person with various physique can be calculated.

According to the example shown in FIG. 16, a laser range finder 247 is used as a unit to detect the position of the heel E. Such laser range finder 247 irradiates a laser beam toward the heel E and captures the reflected beam from the heel E side to calculate the distance.

When the position where the laser range finder 247 is positioned is registered in advance in the ECU device 201, the position of the heel E can be easily detected by the laser range finder 247 when the length z of the lower limb is calculated by the ECU device 201.

For example, virtual coordinates are established on the vehicle floor, and if the operation of the laser range finder 247 which can be rotated is controlled by the ECU device 201, the position of the heel E can be easily detected.

Fourth Embodiment

Conventionally, there is a technique to determine the physique and the skeleton of the person who is seated in the seat and to adjust various positions in the seat to change the posture of the seated person for the purpose of enhancing comfortability and reducing exhaustion when seated in the seat and supporting driving (JP H7-81468, JP2017-81463).

JP 2017-81463 discloses a technique to obtain information regarding the sitting height of the person seated in the seat with the sitting height detection sensor which detects the sitting height as the information to change the seat back.

However, although JP 2017-81463 discloses providing the sitting height detection sensor in the headrest, the document does not disclose the specific position of the sitting height detection sensor. Therefore, there is a needs for a specific attachment structure to enable the detection of the sitting height with the sitting height detection sensor. Further, in the attachment structure, there is a needs to enhance supporting rigidity of the sitting height detection sensor.

Figure 17:
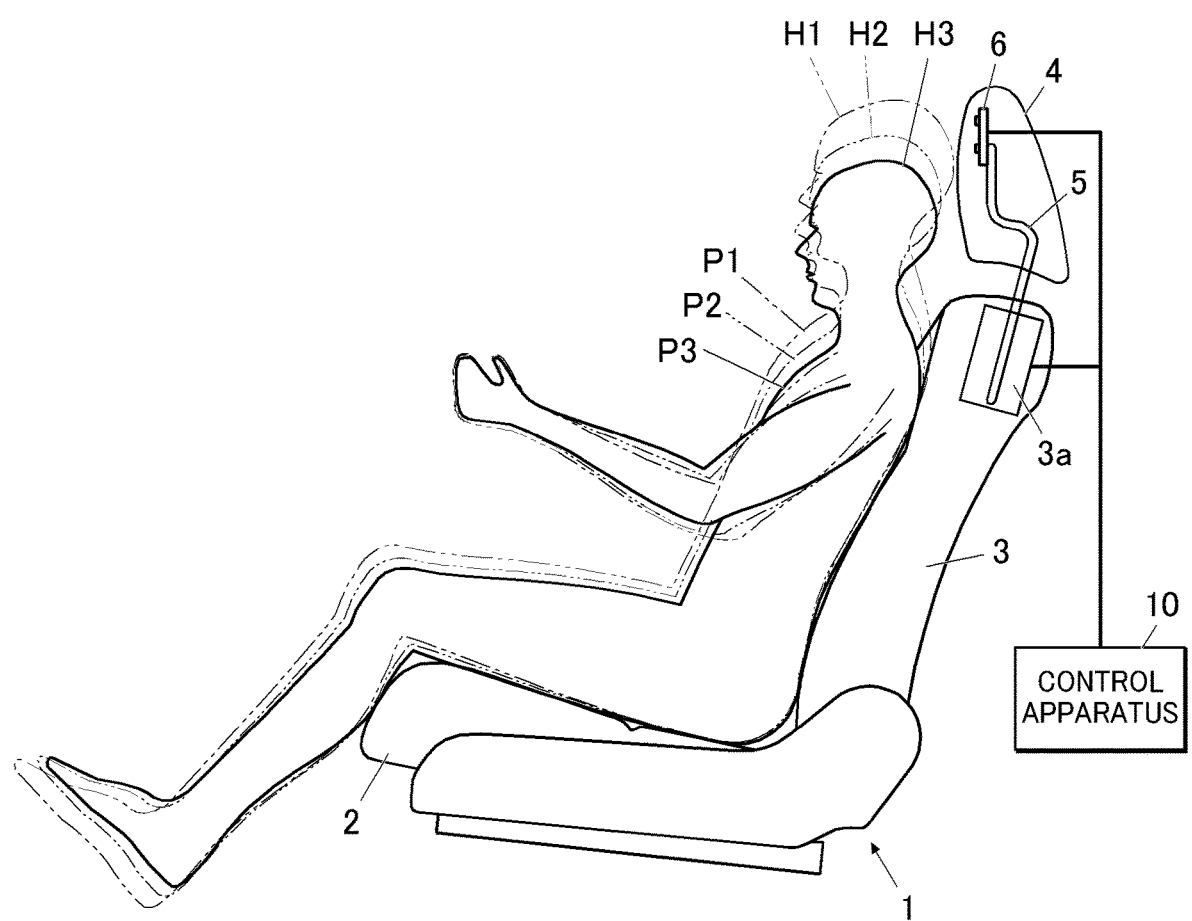
FIG. 17 is a diagram describing a relation of positions between a plurality of people with different sitting heights seated in the seat and the sitting height detection sensor.

Reference numeral 1 shown in FIG. 17 shows a seat in which persons P1 to P3 are seated. The seat 1 is a seat for a vehicle, and according to the present embodiment, the seat 1 is a driver's seat for a passenger car. The seat is not limited to the above, and can be a seat for the passenger car other than the driver's seat, a seat for other automobiles such as a bus or a truck, or can be a seat for vehicles other than automobiles such as trains, ships, and airplanes.

Such seat 1 includes a seat cushion 2 which supports the buttock and the thigh of the persons P1 to P3, a seat back 3 in which the bottom edge is supported by the seat cushion 2 and which is to be the backrest, and a headrest 4 which is provided in the seat back 3 and which supports heads H1 to H3 of the persons P1 to P3.

The sitting height detection sensor 6 which detects the sitting height of the persons P1 to P3 seated in the seat is provided in the headrest 4, and the headrest 4 is moved up and down so as to be able to detect (measure) the sitting height of the persons P1 to P3 with the sitting height detection sensor 6.

The seat cushion 2 mainly includes a seat cushion frame which is to be a skeleton, a cushion pad provided on the seat cushion frame, and an outer layer which covers the seat cushion frame and the cushion pad. A bank portion which expands out is formed in the edges on the left and right side of the seat cushion 2 to enhance the hold of the seated persons P1 to P3.

There is elasticity in the cushion pad in the seat cushion 2. Therefore, this bends when the persons P1 to P3 are seated, and in this amount, the seated persons P1 to P3 sink in the seat cushion 2.

The seat cushion 2 includes a sitting sensor 2a which detects whether the persons P1 to P3 are seated in the seat 1. The sitting sensor 2a is a pressure sensor, and when a certain amount of pressure is applied, the signal is output to the later-described control apparatus 10. Described in more detail, the sitting sensor 2a checks whether the persons P1 to P3 are seated at the hip point.

The hip point is a rotation center point connecting a trunk and a thigh of a three-dimensional mannequin according to American SAE standard J-826 (SAE-3MD type by Ito Precision Machine, Co., Ltd.).

The seat cushion 2 includes a weight measuring sensor 2b which measures the weight of the persons P1 to P3 seated in the seat 1.

The configuration is not limited to the above. The weight of the persons P1 to P3 seated in the seat 1 can be estimated based on the pressure applied to the sitting sensor 2a or the seated persons P1 to P3 can input their own weight on the control apparatus 10. According to the present embodiment, the seat cushion 2 is provided with the weight measuring sensor 2b but the weight measuring sensor 2b can be provided on a floor surface of the vehicle where the seat 1 is provided or a sliding rail on which the seat 1 slides in the front and rear direction.

The seat back 3 mainly includes a seat back frame which is the skeleton, the cushion pad provided on the seat back frame, and the outer layer covering the seat back frame and the cushion pad. A bank portion which expands out to enhance the hold of the seated persons P1 to P3 is formed in the edges on the left and right side of the seat back 3.

A pillar driver 3a is provided in the upper edge of the seat back frame to move the headrest pillar 5 of the headrest 4 (described later) up and down.

Figure 18:
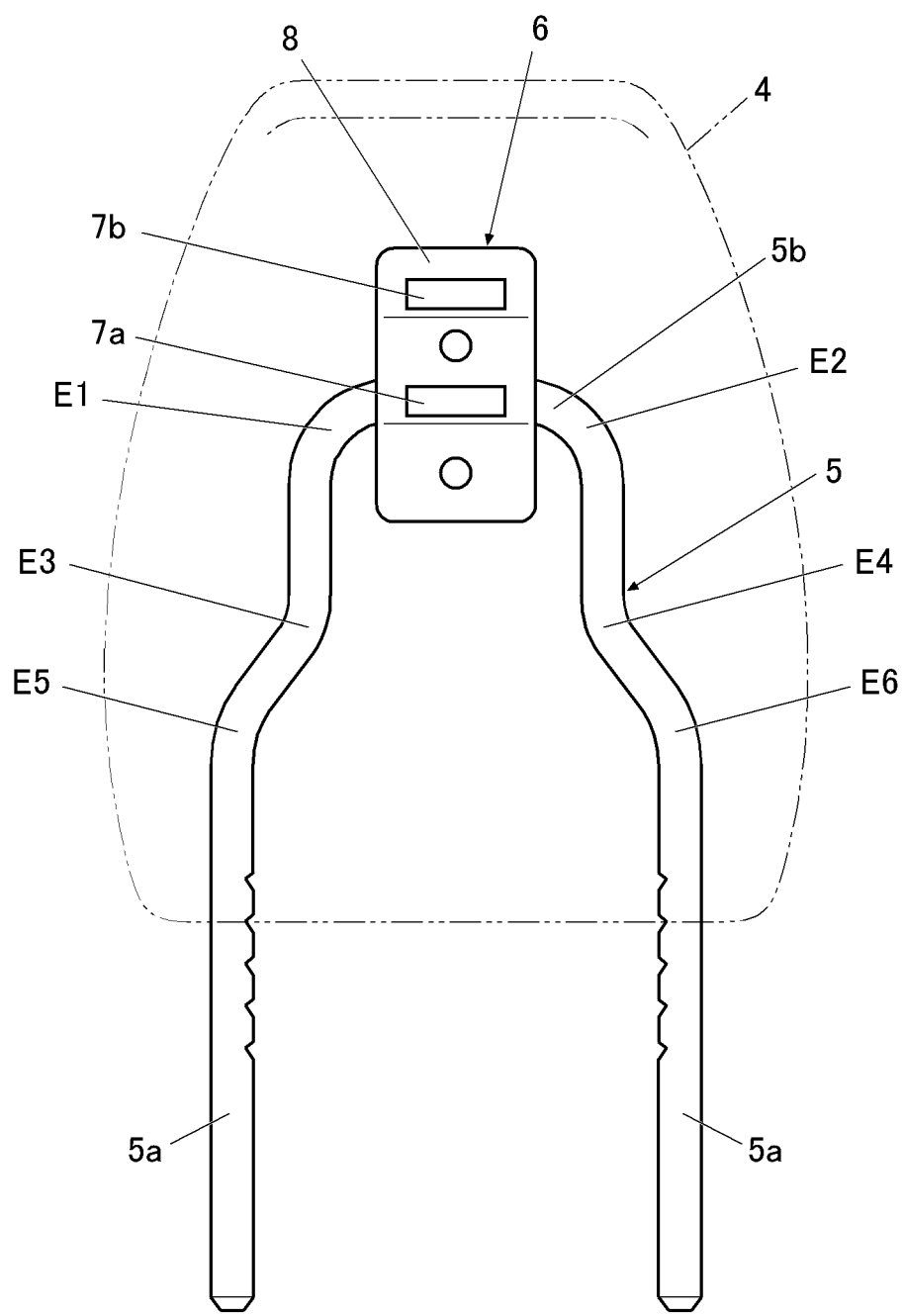
FIG. 18 is a front view showing a headrest in which a sitting height detection sensor is provided.
Figure 19:
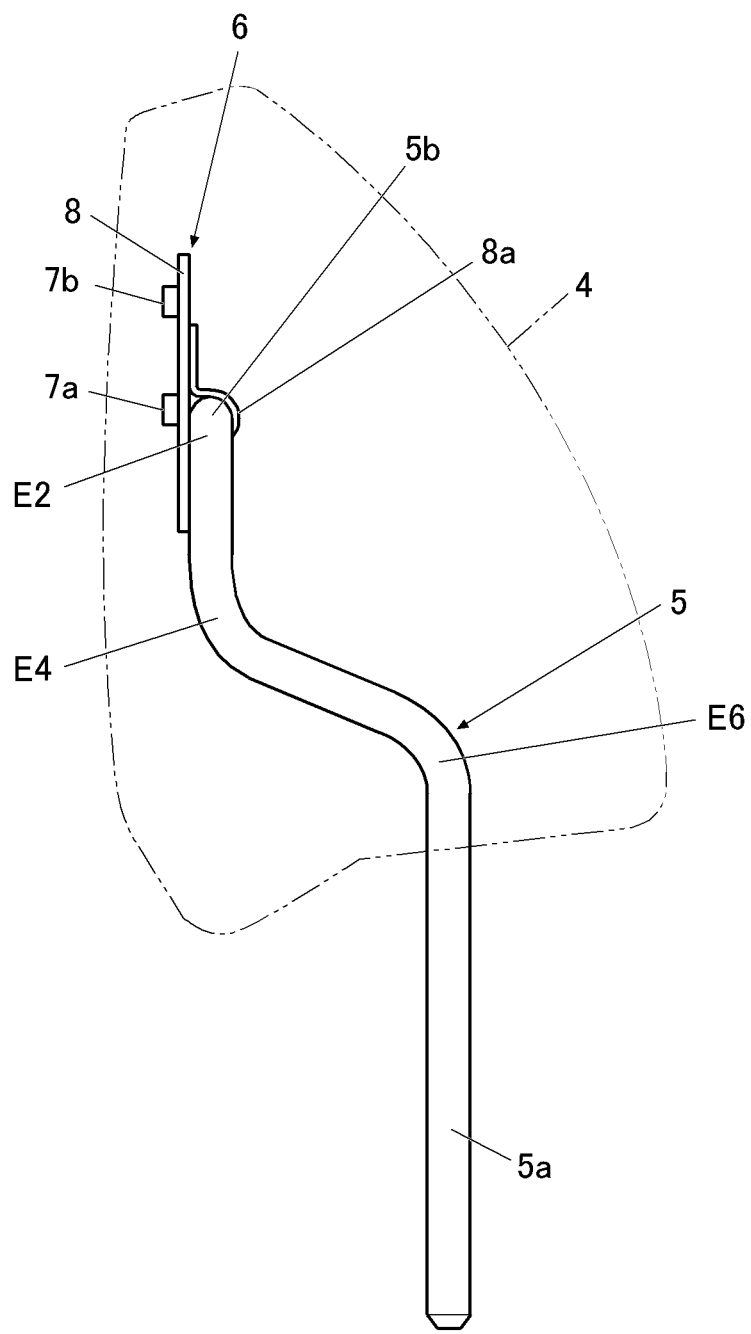
FIG. 19 is a side view showing a headrest in which a sitting height detection sensor is provided.
Figure 30:
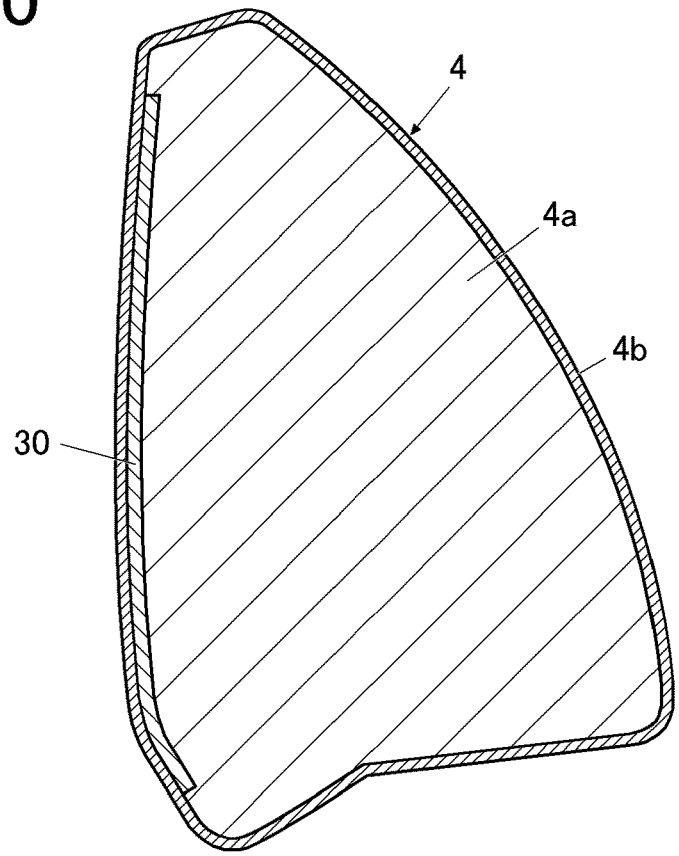
FIG. 30 is a cross-section view showing a modification when a capacitance sensor is included as a sensor main body.

As shown in FIG. 17 to FIG. 19, the headrest 4 includes a headrest pillar 5 in which the portion projecting downwards is provided in the seat back 3, a cushion pad 4a provided surrounding the upper portion of the headrest pillar 5, and the outer layer 4b covering the upper portion of the headrest pillar 5 and the cushion pad 4a (see FIG. 30 regarding the cushion pad 4a and the outer layer 4b).

This headrest 4 can move up and down with relation to the seat back 3 along the headrest pillar 5.

Although not shown, a bank portion projecting to the front side can be formed in the edge on the left and right side of the headrest 4 to enhance the hold of the heads H1 to H3 of the seated persons P1 to P3.

The headrest pillar 5 includes a pair of columns 5a separated to the left and right, and a horizontal axis 5b provided across the upper edges of the pair of columns 5a. The pair of columns 5a and the horizontal axis 5b are formed as one.

The upper portion of the pair of columns 5a is provided in the cushion pad 4a, and the lower portion projects downward from the lower edge surface of the headrest 4. The upper portion of the column 5a according to the present embodiment is formed to fold so as to extend upward projecting forward. The way the pair of columns 5a are formed is not limited to the above, and can be formed by simply extending straight.

The horizontal axis 5b is provided between one column 5a and the other column 5a, and is fixed with a later described bracket 7. Therefore, the horizontal axis 5b and the bracket 7 are provided in the cushion pad 4a.

To describe the headrest pillar 5 according to the present embodiment in more detail, the pair of columns 5a which are formed bent and the horizontal axis 5b are formed as one, and as shown in FIG. 18 and FIG. 19, the headrest pillar 5 includes a plurality of bent portions E1 to E6. Among the plurality of bent portions E1 to E6, bent portions E1 and E2 which connect the pair of columns 5a and the horizontal axis 5b as one are positioned between the pair of columns 5a and the horizontal axis 5b. Each of the pair of columns 5a include two bent portions which are E3 and E5, and E4 and E6 in a position below the bent portions E1 and E2, and the pair of columns 5a are bent in two stages. The headrest pillar 5 includes the plurality of bent portions E1 to E6, and the rigidity is enhanced compared to, for example, a straight column in the headrest pillar.

Further, the bent portions E1 and E2 between the pair of columns 5a and the horizontal axis 5b are positioned in the inner side in the width direction or in equal positions in the width direction with relation to the bent portions E3 to E6 in the pair of columns 5a. Therefore, the dimensions of the horizontal axis 5b can be made shorter, and this prevents the headrest pillar 5 and the headrest 4 from becoming larger.

As shown in FIG. 17 to FIG. 19, the sitting height detection sensor 6 includes sensor main bodies 7a and 7b and a bracket 8 in which the sensor main bodies 7a and 7b are fixed on the front face.

The bracket 8 is formed in a substantial rectangular plate shape, is positioned in the center of the horizontal axis 5b in the headrest pillar 5, and is fixed to the horizontal axis 5b with a fixing member 8a. The bracket 8 formed in a plate shape is positioned so that the surface with a large area faces the front and the rear. Further, the bracket 8 is positioned on the front side (side closer to the persons P1 to P3) of the horizontal axis 5b in the headrest pillar 5.

The fixing member 8a includes two plates aligned with a space in between vertically. The two plates are in contact with the rear surface of the bracket 8 and fixed by the bolt and nut. The fixing member 8a also includes an arc spaced holder provided between the two plates. The horizontal axis 5b in the headrest pillar 5 is held by the arc shaped holder.

The sensor main bodies 7a and 7b are fixed on the front surface of the bracket 8. That is, the sensor main bodies 7a and 7b in the sitting height detection sensor 6 are supported by the headrest pillar 5 with the bracket 8 in between.

Further, the sensor main bodies 7a and 7b in the sitting height detection sensor 6 are positioned at the center of the horizontal axis 5b in the headrest pillar 5 with the bracket 8 in between.

According to the present embodiment, as described above, the headrest pillar 5 includes a plurality of bent portions E1 to E6 and the rigidity is enhanced. Then, the bracket 8 is positioned between the bent portions E1 and E2 in the headrest pillar 5 in which the rigidity is enhanced. Therefore, the supporting rigidity of the bracket 8 and the sensor main bodies 7a and 7b can be enhanced.

The sensor main bodies 7a and 7b include a lower side sensor main body 7a positioned on the lower side and the upper side sensor main body 7b positioned on the upper side.

The lower side sensor main body 7a and the upper side sensor main body 7b are positioned with a space in between on the same vertical line from a front view. That is, the lower side sensor main body 7a and the upper side sensor main body 7b are positioned along the center line in the up and down direction on the front surface of the bracket 8.

The sensor main bodies 7a and 7b are sensors which detect whether heads H1 to H3 of the persons P1 to P3 as the target of sensing exist, and according to the present embodiment, a photoelectric sensor by infrared light (infrared sensor) is used.

Although not shown, the sensor main bodies 7a and 7b which are photoelectric sensors include light emitters which emit light and light receivers which receive light. When the emitted light is reflected by the heads H1 to H3, the amount which reaches the light receiver changes. The light receiver detects this change, converts this to an electric signal, and outputs the signal to the control apparatus 10.

The type of sensor main bodies 7a and 7b is not limited to the photoelectric sensor and can be a radio wave sensor which uses an electromagnetic wave such as a microwave or a sensor which uses ultrasound. That is, preferably, a sensor which can detect whether an object exists without contact is used. The sensor is not limited to the non-contact type sensor, and a contact type sensor can be used.

The configuration of the cushion pad 4a and the outer layer 4b of the headrest 4 is a configuration which does not interfere with the light emitted from the sensor main bodies 7a and 7b.

For example, a through hole is formed in the cushion pad 4a in front of the sensor main bodies 7a and 7b, and through holes are also formed in front of the sensor main bodies 7a and 7b in the outer layer 4b.

Preferably, a coarse mesh fabric is employed in the outer layer 4b so that the light emitted from the sensor main bodies 7a and 7b can easily pass without employing a configuration which stands out such as a through hole.

Further, in the positions of the headrest 4 where the sensor main bodies 7a and 7b are stored, a concave which opens to the front may be formed to store the sensor main bodies 7a and 7b in the concave portion, and a cap member including a transparent member (member which is translucent) can be provided in the front opening. With this, the light emitted from the sensor main bodies 7a and 7b is not blocked. Preferably, the cap member includes flexibility.

The control apparatus 10 is also called an ECU (Electronic Control Unit). As shown in FIG. 17, the control apparatus 10 controls the operation of the pillar driver 3a based on the electric signal output from the sensor main bodies 7a and 7b, and controls the vertical movement of the headrest pillar 5. By moving the headrest pillar 5 up and down, the headrest 4 can be moved up and down, and the sitting height of each person P1 to P3 seated in the seat can be measured.

Figure 20:
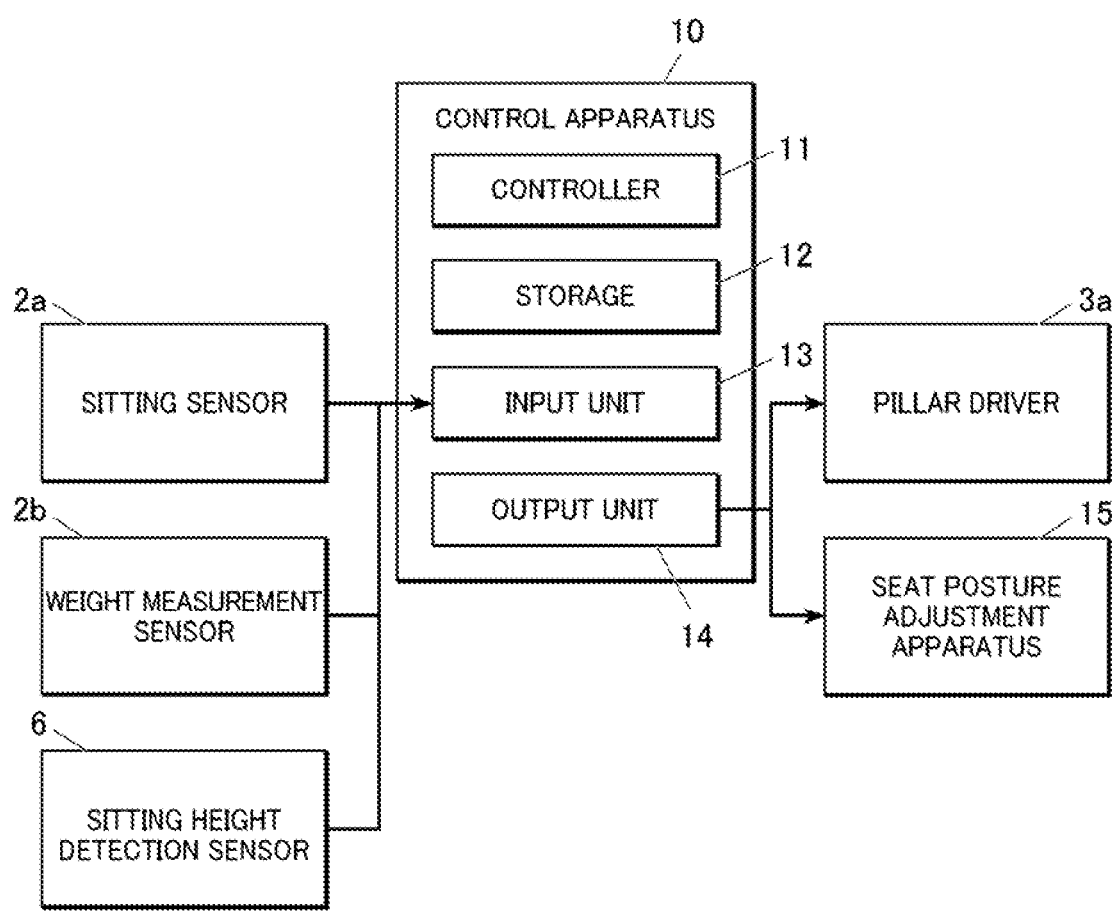
FIG. 20 is a diagram showing a configuration of a control apparatus in which the headrest is moved up and down based on the detection result by the sitting height detection sensor.
Figure 21:
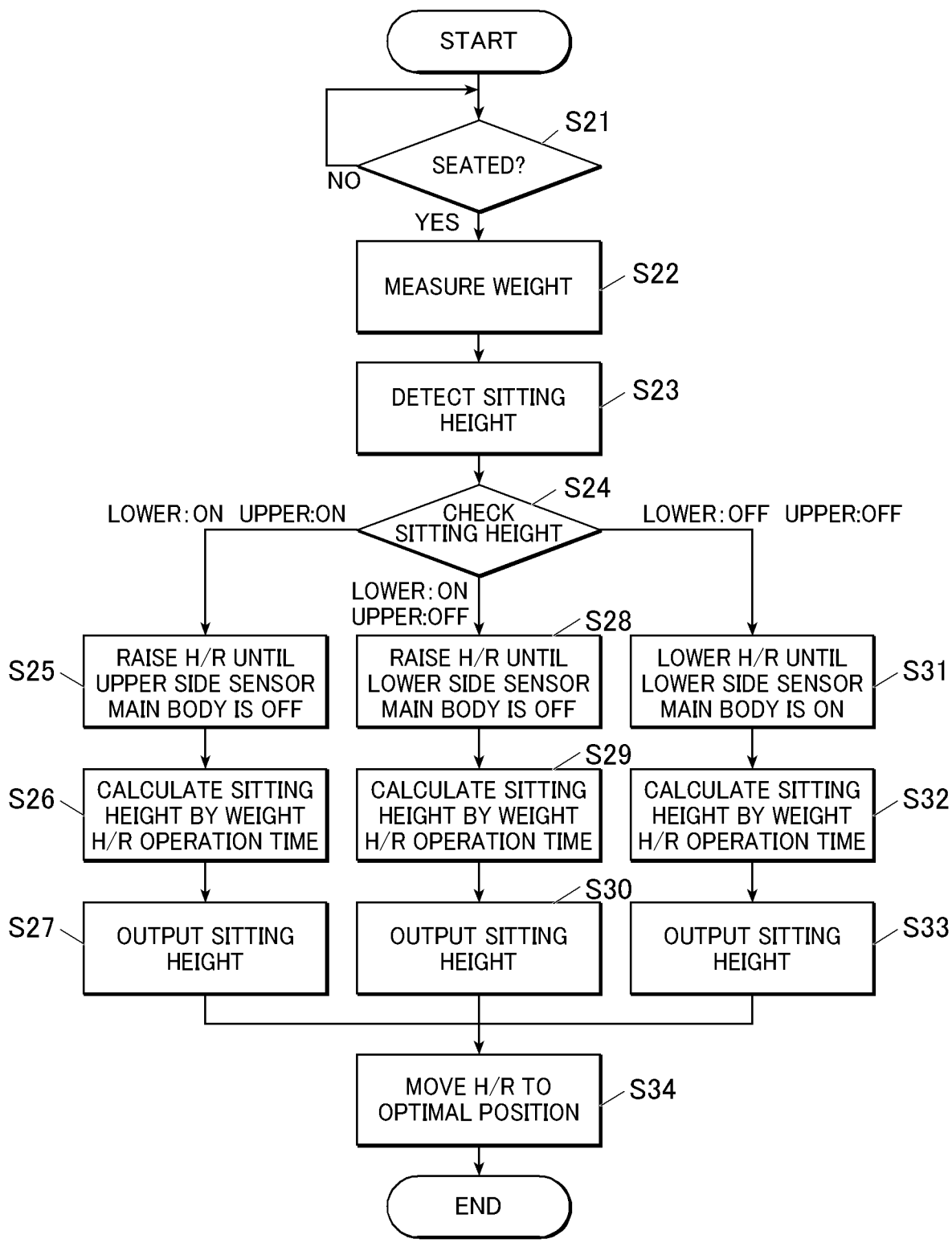
FIG. 21 is a flowchart showing from when a person sits in a seat to when the position adjustment of the headrest 4 is performed.

As shown in FIG. 20, the control apparatus 10 includes a controller 11, a storage 12, an input unit 13, and an output unit 14.

The controller 11 includes, a Central Processing Unit (CPU), a Random Access Memory (RAM), and a Read Only Memory (ROM), and various operations to detect the sitting height are performed. That is, based on the control by the controller 11, the pillar driver 3a is moved and the headrest pillar 5 is moved vertically.

The storage 12 includes, for example, a RAM, a ROM, a nonvolatile memory, or a hard disk drive, and stores various programs and various data necessary to detect the sitting height. Various data and signals input from outside the control apparatus 10 are stored.

Various programs stored in the storage 12 include a sitting height measurement program, a headrest adjustment program, and a variety of programs. The various programs show their functions by being executed by the controller 11.

The input unit 13 is for inputting to the control apparatus 10 an electric signal output from the sitting height detection sensor 6 and the sitting sensor 2, and the measurement value information output from the weight measuring sensor 2b.

The output unit 14 is for outputting the instruction signal to operate the pillar driver 3a.

Other than the sitting height detection sensor 6 and the pillar driver 3a, the control apparatus 10 is connected to various sensors (not shown) provided in various places of the seat 1 and a seat posture adjustment apparatus 15.

The seat posture adjustment apparatus 15 adjusts the positions of various locations of the seat 1 according to the physique and the skeleton of the persons P1 to P3 seated in the seat 1 detected by various sensors, and changes the posture of the seated persons P1 to P3. The seat posture adjustment apparatus 15 is provided in the seat 1. That is, the control apparatus 10 not only adjusts the position of the headrest 4, but also functions as the unit which adjusts the entire position of the seat 1.

According to such seat posture adjustment apparatus 15, for example, the seat cushion 2 can be tilted to the front and the rear and to the left and the right, the seat back 3 can be reclined, and the tilt of the projection in the bank portion of the seat cushion 2 and the seat back 3 can be adjusted.

Next, as shown in FIG. 21 to FIG. 24, the method to detect (measure) the sitting height of the persons P1 to P3 seated in the seat 1 by the sitting height detection sensor 6 is described.

The persons P1 to P3 seated in the seat 1 each have different physique and the sitting height is different. As shown in FIG. 17, the persons P1 to P3 seated in the seat 1 include the person P1 with a tall sitting height, the person P2 with a middle sitting height, and the person P3 with a short sitting height. The person P1 with the tall sitting height includes the head H1, the person P2 with the middle sitting height includes the head H2, and the person P3 with the short sitting height includes the head H3.

First, the sitting sensor 2a detects whether the persons P1 to P3 are seated in the seat 1 (step S21). Preferably, the sitting height detection sensor 6 does not operate until the sitting sensor 2a confirms the persons P1 to P3 are seated in order to reduce the consumed power.

Next, when the sitting sensor 2a detects that the persons P1 to P3 are seated in the seat 1, the weight measuring sensor 2b measures the weight of the persons P1 to P3 seated in the seat 1 (step S22).

Next, the sitting height detection sensor 6 operates to detect the heads H1 to H3 of the persons P1 to P3 seated in the seat 1. Described specifically, the lower side sensor main body 7a and the upper side sensor main body 7b in the sitting height detection sensor 6 detect whether the heads H1 to H3 of the persons P1 to P3 seated in the seat 1 exist (step S23).

Then, the detection result by the sitting height detection sensor 6 is output to the control apparatus 10, the sitting height measurement program is performed by the controller 11, and with this, the sitting height is checked (step S24). According to the present embodiment, the steps performed based on the sitting height measurement program are from the sitting height check to the output of the sitting height information.

Figure 22:
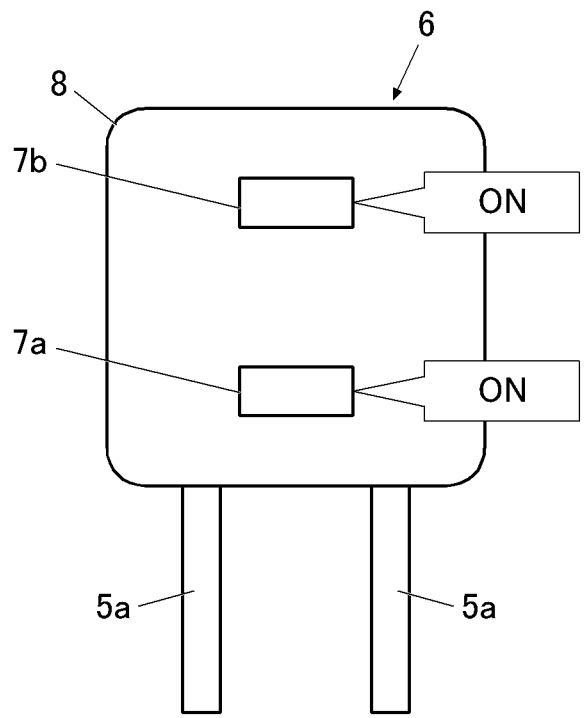
FIG. 22 is a diagram showing a state of the sitting height detection sensor when a person with a tall sitting height is detected.

When the person P1 with the tall sitting height is seated in the seat 1, as shown in FIG. 17 and FIG. 22, the head H1 is detected by both the lower side sensor main body 7a and the upper side sensor main body 7b (state in which lower side: ON and upper side: ON). That is, when both the lower side sensor main body 7a and the upper side sensor main body 7b detect the head H1, the person P1 seated in the seat 1 is considered to be the person P1 with the tall sitting height.

The ON state refers to a state in which the light emitted from the light emitter of the sensor hits the heads H1 to H3 and the light is reflected, and then the necessary amount of light is received by the light receiver.

On the other hand, the OFF state refers to a state in which the light emitted from the light emitter of the sensor does not hit the heads H1 to H3, and the necessary amount of light is not received by the light receiver. When the light emitted from the light emitter hits an object positioned farther than the heads H1 to H3 and is reflected, the amount of light does not reach the necessary amount. Therefore, it is determined that the heads H1 to H3 do not exist ahead of the light emitted from the sensor.

When the head H1 is detected by both the lower side sensor main body 7a and the upper side sensor main body 7b, the controlling apparatus 10 operates the pillar driver 3a, and raises the headrest 4 until the upper side sensor main body 7b becomes an OFF state (step S25).

Next, the operation time of the headrest 4 until the upper side sensor main body 7b becomes an OFF state by raising the headrest 4 and the weight of the person P1 measured by the weight measuring sensor 2b are calculated to calculate the sitting height of the person P1 (step S26).

By including the weight of the person P1 measured by the weight measuring sensor 2b in the calculation formula, the correction can be made considering the sinking in the seat cushion 2 when the person P1 is seated in the seat 1. Therefore, accuracy of detecting the sitting height can be enhanced.

Then, the sitting height information of the person P1 is output (step S27), and the control apparatus 10 executes the headrest adjustment program based on the above and moves the headrest 4 to the position optimal for the person P1 (step S34).

Figure 23:
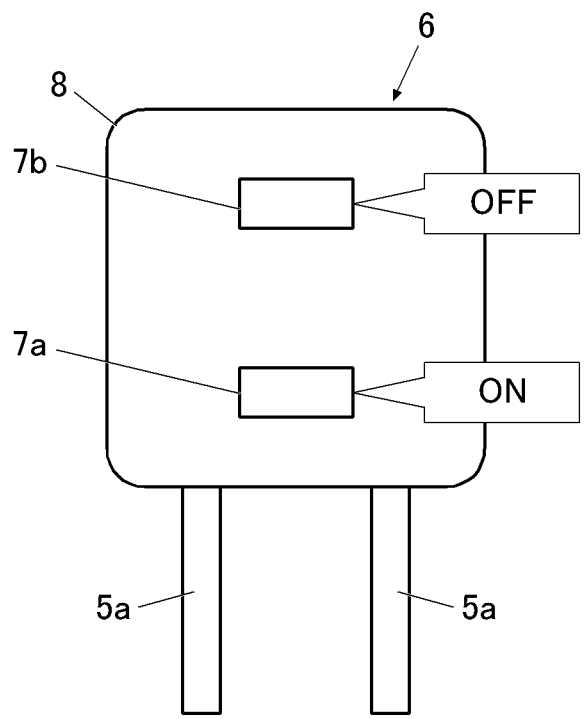
FIG. 23 is a diagram showing a state of a sitting height detection sensor when a person with a medium sitting height is detected.

When the person P2 with the middle sitting height is seated in the seat 1, as shown in FIG. 17 and FIG. 23, the head H2 is detected by only the lower side sensor main body 7a.

That is, if the head H2 is detected by only the lower side sensor main body 7a, the person P2 seated in the seat 1 is considered to be the person P2 with the middle sitting height.

When the head H2 is detected by only the lower side sensor main body 7a, the pillar driver 3a is operated by the control apparatus 10, and the headrest 4 is raised until the lower side sensor main body 7a becomes the OFF state (step S28).

The operation time of the headrest 4 until the lower side sensor main body 7a becomes an OFF state by raising the headrest 4 and the weight of the person P2 measured by the weight measuring sensor 2b are calculated to calculate the sitting height of the person P2 (step S29).

Then, the sitting height information of the person P2 is output (step S30), and the control apparatus 10 executes the headrest adjustment program based on the above and moves the headrest 4 to the position optimal for the person P2 (step S34).

Figure 24:
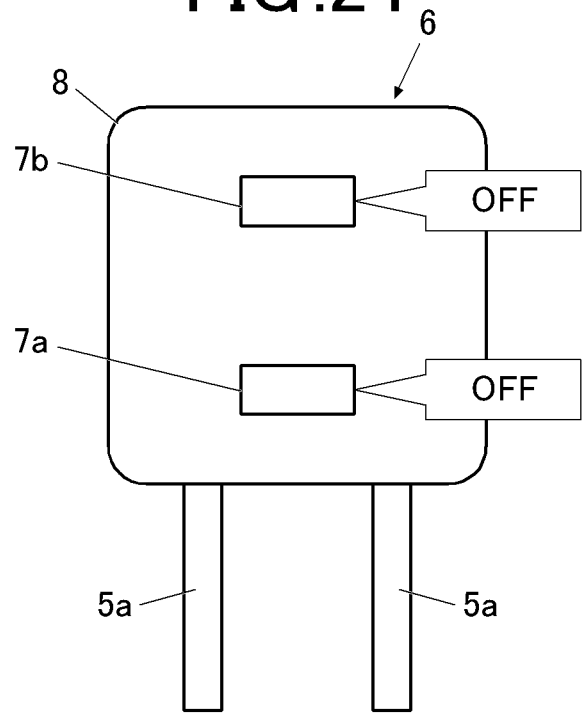
FIG. 24 is a diagram showing a state of a sitting height detection sensor when a person with a short sitting height is detected.

When the person P3 with the short sitting height is seated in the seat 1, as shown in FIG. 17 and FIG. 24, both the lower side sensor main body 7a and the upper side sensor main body 7b do not detect the head H3.

That is, if both the lower side sensor main body 7a and the upper side sensor main body 7b do not detect the head H3, the person P3 seated in the seat 1 is considered to be the person P3 with the short sitting height.

If both the lower side sensor main body 7a and the upper side sensor main body 7b do not detect the head H3, the control apparatus 10 operates the pillar driver 3a, and lowers the headrest 4 until the lower side sensor main body 7a is in the ON state (step S31).

The operation time of the headrest 4 until the lower side sensor main body 7a becomes an ON state by lowering the headrest 4 and the weight of the person P3 measured by the weight measuring sensor 2b are calculated to calculate the sitting height of the person P3 (step S32).

Then, the sitting height information of the person P3 is output (step S33), and the control apparatus 10 executes the headrest adjustment program based on the above and moves the headrest 4 to the position optimal for the person P3 (step S34).

As described above, the sitting height of the persons P1 to P3 seated in the seat 1 can be detected (measured). That is, after the persons P1 to P3 are seated in the seat 1, the process up to adjusting the position of the headrest 4 to be the optimal position for the seated persons P1 to P3 is automatically performed.

Figure 25:
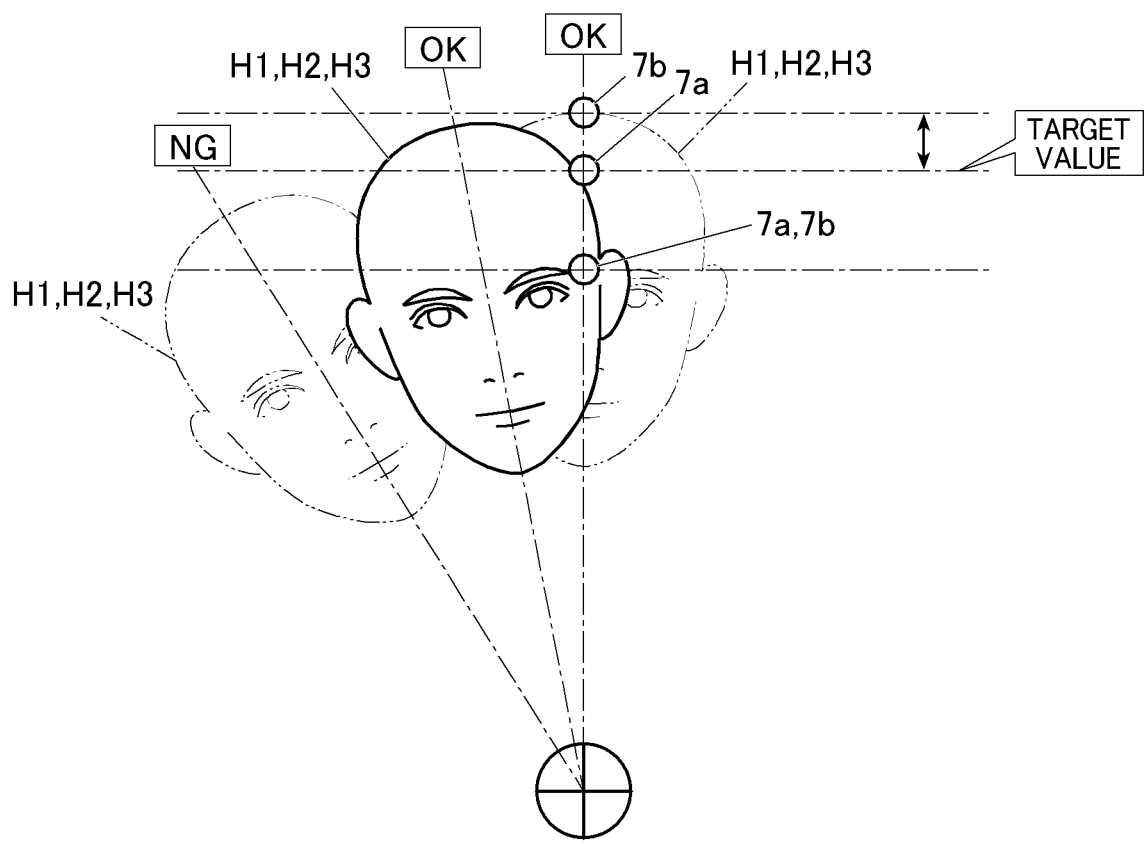
FIG. 25 is a diagram describing how sitting height detection is performed when a head of a person is tilted with relation to the sitting height detection sensor.

As shown in FIG. 25, when the persons P1 to P3 are seated in the seat 1, the persons P1 to P3 may not sit straight along the center line of the seat 1 (virtual line positioned at the center from the front view), and may sit with the body tilted with relation to the center line. That is, there may be a variation in the way a person sits in the seat 1 from time to time even for the same individual, and the individual may not always sit straight along the center line.

According to the present embodiment, the lower side sensor main body 7a and the upper side sensor main body 7b are aligned with an interval in the horizontal direction. Therefore, if the heads H1 to H3 can be detected within the above range, even when seated with the body tilted, the sitting height can be measured. According to the present embodiment, a predetermined target value is set for authenticated accuracy of the sitting height measured by sitting in the seat 1 of the present embodiment with relation to the actual sitting height. If it is within the range of the target value of the sitting height authenticated accuracy, the error of the measured sitting height is small and the sitting height can be measured even if the body is tilted.

For example, in the example shown in FIG. 25, even if the body is slightly tilted, the position of the heads H1 to H3 is detected within the range up to the target value by the lower side sensor main body 7a. Therefore, the sitting height can be measured (OK). On the other hand, if the body is greatly tilted, the heads H1 to H3 are positioned outside the range to the target value, and the lower side sensor main body 7a cannot detect the heads H1 to H3. Therefore, the sitting height cannot be detected (NG).

It may not be possible to detect the sitting height even if the headrest 4 is raised to the highest positon or lowered to the lowest position. That is, when the sitting height is detected by the seat 1 according to the present embodiment, there may be limits due to the physique of the person. However, for example, by making the length of the headrest pillar 5 longer or by employing a structure of the seat back 3 or the headrest 4 in which the headrest 4 can sink to the seat back 3 side, the range of detecting the sitting height becomes larger. Therefore, preferably, the above are suitably employed.

According to the present embodiment, the sitting height detection sensor 6 which detects the sitting height of the persons P1 to P3 seated in the seat 1 is supported with the headrest pillar 5 in the headrest 4 which supports the heads H1 to H3 of the persons P1 to P3. The headrest 4 with the sitting height detection sensor 6 attached can be moved up and down with relation to the seat back 3 and the sitting height of the persons P1 to P3 seated in the seat 1 can be detected. That is, a specific attachment structure which can detect the sitting height with the sitting height detection sensor 6 can be provided. Further, the sitting height detection sensor 6 is supported by the headrest pillar 5, and the supporting rigidity of the sitting height detection sensor 6 can be heightened.

The sitting height detection sensor 6 is positioned at the center of the horizontal axis 5b in the headrest pillar 5. Therefore, the sitting height detection sensor 6 is positioned in a high position and at the center of the headrest 4. Therefore, the sitting height of the persons P1 to P3 seated in the seat 1 can be easily detected.

The bracket 8 with the lower side sensor main body 7a and the upper side sensor main body 7b which are the sensor main bodies fixed to the front surface is positioned on the front side of the headrest pillar 5. Therefore, the lower side sensor main body 7a and the upper side sensor main body 7b fixed to the front surface of the bracket 8 are positioned to be close to the heads H1 to H3 of the persons P1 to P3. Therefore, it is difficult for the accuracy of detecting the sitting height by the sitting height detection sensor 6 to decrease.

[Modification 6]

Figure 26:
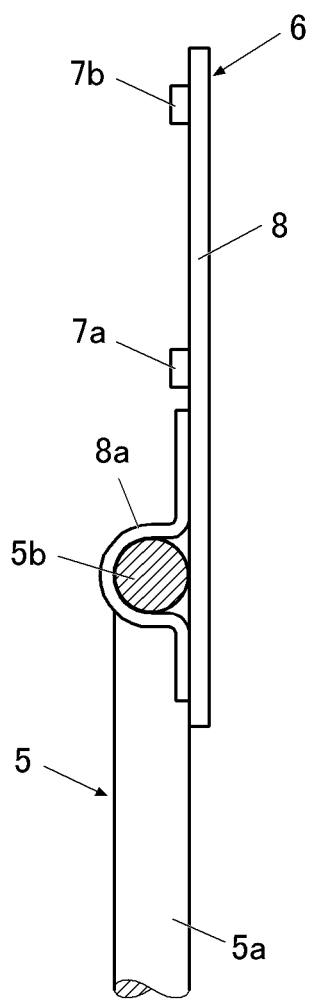
FIG. 26 is a diagram showing a modification of an attaching position of a bracket.

The above described bracket 8 according to the present embodiment is positioned on the front side of the headrest pillar 5, but as shown in FIG. 26, the bracket 8 in the modification is positioned on the rear side of the headrest pillar 5.

Described in detail, the bracket 8 according to the modification is formed in a substantial rectangular plate shape. The bracket 8 is positioned at the center of the horizontal axis 5b in the headrest pillar 5, and is fixed to the horizontal axis 5b with the fixing member 8a. The bracket formed in such plate shape is positioned so that the surface with the large area faces the front and the rear. Further, the bracket 8 is positioned on the rear side of the horizontal axis 5b in the headrest pillar 5 (side far from the persons P1 to P3).

The lower side sensor main body 7a and the upper side sensor main body 7b are positioned with an interval vertically on the front surface of the bracket 8.

According to the present modification, in addition to achieving the same effects as the above-described embodiment, since the bracket 8 is positioned on the rear side of the headrest pillar 5, the lower side sensor main body 7a and the upper side sensor main body 7b fixed to the front surface of the bracket 8 are positioned separated from the heads H1 to H3 of the persons P1 to P3. Therefore, the persons P1 to P3 seated in the seat 1 hardly feel discomfort at the heads H1 to H3.

[Modification 7]

Figure 27:
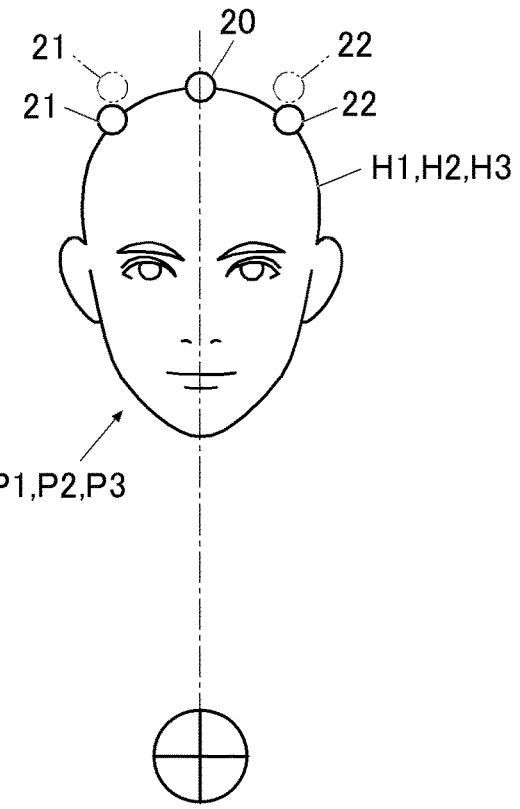
FIG. 27 is a diagram showing a modification when a sitting height detection sensor includes a sub-sensor.
Figure 28:
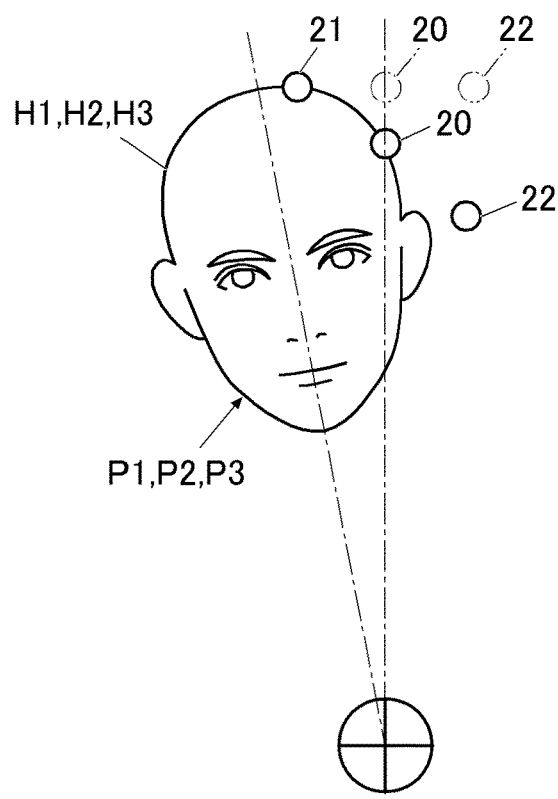
FIG. 28 is a diagram showing a modification when the sitting height detection sensor includes the sub-sensor.
Figure 29:
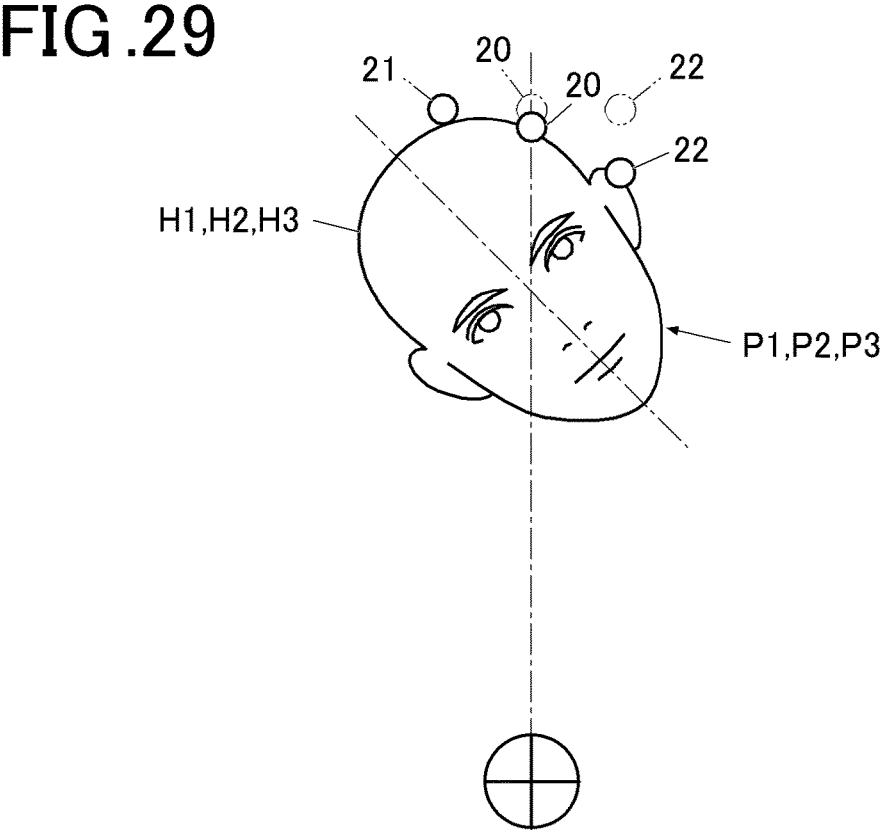
FIG. 29 is a diagram showing a modification when the sitting height detection sensor includes the sub-sensor.

As shown in FIG. 27 to FIG. 29, the sitting height detection sensor according to the modification includes a sensor main body 20, and sub-sensors 21 and 22 which detect the tilt of the heads H1 to H3 of the persons P1 to P3.

The sub-sensors 21 and 22 include a first sub-sensor 21 and a second sub-sensor 22 positioned to the left and the right of the sensor main body 20.

Such sensor main body 20 is positioned so that there is an interval from the first sub-sensor 21 and the second sub-sensor 22, and the sensor main body 20, the first sub-sensor 21, and the second sub-sensor 22 are positioned on the same straight line in a side direction from a front view. The interval is set to about 45 mm to 55 mm, for example, and according to the present embodiment, the interval is set to 50 mm.

The sensor main body 20, the first sub-sensor 21, and the second sub-sensor 22 are attached to the front surface of the bracket (not shown).

According to the modification, there is one sensor main body 20, but a plurality of sensor main bodies 20 can be provided vertically similar to the above-described embodiment.

The sensor main body 20, the first sub-sensor 21, and the second sub-sensor 22 are sensors which detect whether the heads H1 to H3 of the persons P1 to P3 as the target of sensing exist, and similar to the above-described embodiment, the photoelectric sensor by infrared light is used. However, the type of sensor is not limited to the above.

Similar to the above-described embodiment, the sensor main body 20, the first sub-sensor 21, and the second sub-sensor 22 can move vertically.

According to the example shown in FIG. 27, the persons P1 to P3 are shown in a state seated straight along the center line of the seat 1. The sensor main body 20, the first sub-sensor 21, and the second sub-sensor 22 are lowered while sensing the heads H1 to H3 of the persons P1 to P3 in the above state.

The sensor main body 20, the first sub-sensor 21 and the second sub-sensor 22 are positioned in the initial position (for example, the position where the headrest 4 is moved to the highest position).

In the initial position, the light emitted from the light emitter does not hit the heads H1 to H3, and the sensor main body 20, the first sub-sensor 21, and the second sub-sensor 22 are in the above-described OFF state.

Further, when the sensor main body 20, the first sub-sensor 21, and the second sub-sensor 22 are lowered, the sensor main body 20 detects the highest position of the heads H1 to H3 (top of head) and becomes the ON state.

The measurement value information when the sensor main body 20 is in the ON state, is output to the control apparatus 10 and is stored in the storage 12.

Next, when the sensor main body 20, the first sub-sensor 21 and the second sub-sensor 22 are lowered, the first sub-sensor 21 and the second sub-sensor 22 detect the highest position of the side of the head in the heads H1 to H3, and become the ON state.

The measurement value information when the first sub-sensor 21 and the second sub-sensor 22 are in the ON state is output to the control apparatus 10 and stored in the storage 12.

Then, the control apparatus 10 calculates the operation time of the headrest 4 until the sensor main body 20, the first sub-sensor 21, and the second sub-sensor 22 become the ON state by lowering the headrest 4 from the initial position and the weight of the persons P1 to P3 measured by the weight measuring sensor 2b are calculated to calculate the sitting height of the persons P1 to P3.

The control apparatus 10 moves the headrest 4 to the position optimal for the persons P1 to P3 seated in the seat 1 based on the measurement value information of the sensor main body 20, the first sub-sensor 21, and the second sub-sensor 22.

The example shown in FIG. 28 shows a state in which the body of the persons P1 to P3 are tilted and seated in the center line of the seat 1 (for example, near the ninth thoracic vertebrae as the rotating axis). The sensor main body 20, the first sub-sensor 21, and the second sub-sensor 22 are lowered to sense the heads H1 to H3 of the persons P1 to P3 in the above state.

When the sensor main body 20, the first sub-sensor 21, and the second sub-sensor 22 are lowered from the initial position, the sub-sensor toward where the body is tilted (here, first sub-sensor 21) detects the highest position in the heads H1 to H3 in the tilted state and becomes the ON state.

The measurement value information when the first sub-sensor 21 is in the ON state is output to the control apparatus 10 and stored in the storage 12.

Further, when the sensor main body 20, the first sub-sensor 21, and the second sub-sensor 22 are lowered, the sensor main body 20 detects the heads H1 to H3 (near the side of the head) and becomes the ON state.

The measurement value information when the sensor main body 20 is in the ON state is output to the control apparatus 10 and stored in the storage 12.

Next, when the sensor main body 20, the first sub-sensor 21, and the second sub-sensor 22 are lowered, the second sub-sensor 22 does not detect the heads H1 to H3 and maintains the OFF state.

When the sensor main body 20, the first sub-sensor 21, and the second sub-sensor 22 are lowered to the lowest position with the second sub-sensor 22 maintaining the OFF state, the control apparatus 10 determines that there is no measurement value information. In detail, the control apparatus 10 is able to understand that the body is tilted to a degree that the second sub-sensor 22 cannot detect the body based on the operation time and the measurement value information of the sensors 20, 21, and 22.

Then, the control apparatus 10 calculates the operation time of the headrest 4 until the sensor main body and the first sub-sensor 21 become the ON state by lowering the headrest 4 from the initial position and the weight of the persons P1 to P3 measured by the weight measuring sensor 2b are calculated to calculate the sitting height of the persons P1 to P3.

The control apparatus 10 moves the headrest 4 to the position optimal for the persons P1 to P3 seated in the seat 1 based on the measurement value information of the sensor main body 20 and the first sub-sensor 21.

For example, based on the measurement value information of the sensor main body 20 and the first sub-sensor 21, and the information that there is no measurement value information by the second sub-sensor 22, the control apparatus 10 can correct the posture of the persons P1 to P3 seated in the seat 1 to be straight with the seat posture adjustment apparatus 15.

Even if the body of the persons P1 to P3 seated in the seat 1 is tilted, the second sub-sensor 22 may detect the heads H1 to H3 of the persons P1 to P3 depending on the degree of the tilt. In this case, the measurement value information of the second sub-sensor 22 is considered and the headrest 4 is moved to the position optimal for the persons P1 to P3 seated in the seat 1.

According to the example shown in FIG. 29, the persons P1 to P3 are shown seated with the heads H1 to H3 of the persons P1 to P3 tilted with relation to the center line of the seat 1 (state with the neck tilted). The sensor main body 20, the first sub-sensor 21, and the second sub-sensor are lowered while sensing the heads H1 to H3 of the persons P1 to P3 in such state.

When the sensor main body 20, the first sub-sensor 21, and the second sub-sensor 22 are lowered from the initial position, the sub-sensor on the side that the neck is tilted (here, first sub-sensor 21) detects the highest position in the heads H1 to H3 in the tilted state and becomes the ON state.

The measurement value information when the sensor main body 21 is in the ON state is output to the control apparatus 10 and stored in the storage 12.

When the sensor main body 20, the first sub-sensor 21, and the second sub-sensor 22 are lowered, the sensor main body 20 detects the heads H1 to H3 (near the side of the head) and becomes the ON state.

The measurement value information when the sensor main body 20 is in the ON state is output to the control apparatus 10 and stored in the storage 12.

Next, when the sensor main body 20, the first sub-sensor 21, and the second sub-sensor 22 are lowered, the second sub-sensor 22 detects the heads H1 to H3 (side of head, near the ear) and becomes the ON state.

The measurement value information when the second sub-sensor 22 is in the ON state is output to the control apparatus 10 and stored in the storage 12.

Then, the control apparatus 10 calculates the operation time of the headrest 4 until the sensor main body 20, the first sub-sensor 21, and the second sub-sensor 22 become the ON state by lowering the headrest 4 from the initial position and the weight of the persons P1 to P3 measured by the weight measuring sensor 2b is calculated to calculate the sitting height of the persons P1 to P3.

The control apparatus 10 moves the headrest 4 to the position optimal for the persons P1 to P3 seated in the seat 1 based on the measurement value information of the sensor main body 20, the first sub-sensor 21, and the second sub-sensor 22.

For example, based on the measurement value information of the sensor main body 20, the first sub-sensor 21, and the second sub-sensor 22, the control apparatus 10 can correct the posture of the persons P1 to P3 seated in the seat 1 to be straight with the seat posture adjustment apparatus 15.

According to the present modification, in addition to achieving the effects similar to the above-described embodiment, the sitting height detection sensor includes the first sub-sensor 21 and the second sub-sensor 22 which are the sub-sensors to detect the tilt of the heads H1 to H3 of the persons P1 to P3, the sitting height can be detected even if the heads H1 to H3 of the persons P1 to P3 are tilted, and the detection accuracy of the sitting height by the sitting height detection sensor is enhanced.

As in the present modification, if the sitting height detection sensor includes the sensor main body 20, and the sub-sensors 21 and 22 which detect the tilt of the heads H1 to H3 of the persons P1 to P3, the sitting height authenticated accuracy is within the range from the predetermined target value, and the accuracy of detecting the sitting height by the sitting height detection sensor is greatly enhanced.

[Modification 8]

A capacitance sensor is employed as the sensor main body 30 which is the sitting height detection sensor according to the present modification.

As shown in FIG. 30, the sensor main body 30 is positioned in a position between the front side surface in the cushion pad 4a of the headrest 4 and the rear side (inner side) of the outer layer 4b.

The entire sensor main body 30 which is the capacitance sensor is shaped in a thin plate shape with flexibility, and is formed to be long in the up and down direction. The capacitance sensor is able to detect the relative position of the sensing target in a non-contact state.

Specifically described, when the distance from the heads H1 to H3 of the persons P1 to P3 as the sensing target changes, the capacitance of the electrode (not shown) changes by the electrostatic induction effect. The sensor main body 30 which is the capacitance sensor detects the position of the heads H1 to H3 based on the percentage of the change in the capacitance.

The sitting height detection sensor according to the present modification is positioned between the cushion pad 4a and the outer layer 4b. Since the cushion pad 4a itself and the outer layer 4b itself are supported by the headrest pillar 5, the sitting height detection sensor is also supported by the headrest pillar 5 indirectly through the cushion pad 4a and the outer layer 4b.

When the heads H1 to H3 of the persons P1 to P3 are detected by the sensor main body 30, similar to the above-described embodiment, the pillar driver 3a is operated to move the headrest 4 up and down. With this, the position of the heads H1 to H3 can be detected.

Figure 31:
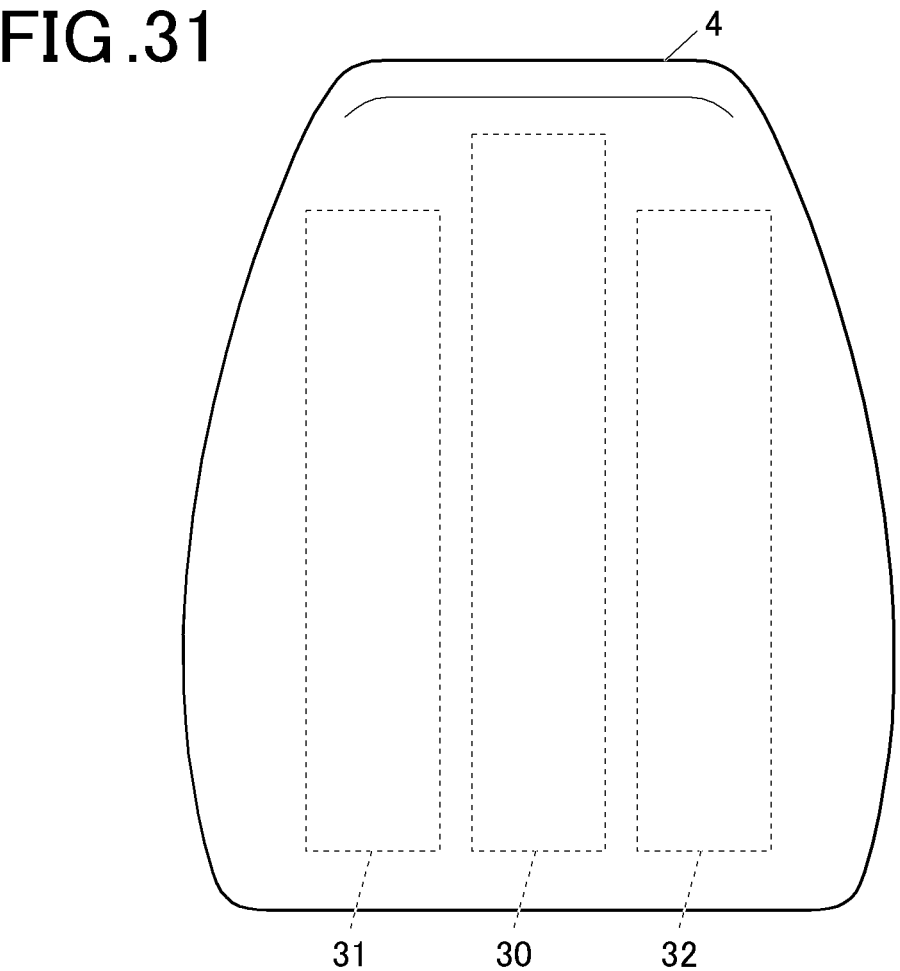
FIG. 31 is a front view showing a modification when the capacitance sensor is included as the sensor main body.

As shown in FIG. 31, the sitting height detection sensor according to the present modification can include the sub-sensors 31 and 32 which detect the tilt of the head of the person.

The sub-sensors 31 and 32 include the first sub-sensor 31 and the second sub-sensor 32 positioned on the left and the right of the sensor main body 20. When a bank portion is formed in the headrest 4, the first sub-sensor 31 and the second sub-sensor 32 can be positioned in the bank portion.

Both the first sub-sensor 31 and the second sub-sensor 32 are the capacitance sensor similar to the sensor main body 30, and the entire sensor is a thin plate shape with flexibility and is formed to be long in the up and down direction.

By using the sensor main body 30, the first sub-sensor 31, and the second sub-sensor 32 according to the present modification, the effects similar to the above-described embodiment and the modification 2 can be achieved. Moreover, the sensor main body 30, the first sub-sensor 31, and the second sub-sensor 32 can be used in the headrest 4 regardless of the shape of the headrest pillar 5. That is, although the sitting height detection sensor is supported indirectly by the headrest pillar 5, the sitting height detection sensor is separated from the headrest pillar 5. Therefore, there is not much trouble in using the sitting height detection sensor in the headrest 4 no matter how the headrest pillar 5 is shaped.

With this, the sitting height detection sensor can be suitably used when there are needs regardless of the shape of the headrest pillar 5, for example.

The region showing good detection sensitivity is relatively small in a capacitance sensor. Therefore, when the capacitance sensor is used as the sensor main body 30, the first sub-sensor 31, and the second sub-sensor 32, the position of the headrest 4 may be configured to be able to be adjusted to the front and the back, and the headrest 4 may be configured to be able to come close to the heads H1 to H3.

[Modification 9]

A pressure sensor is employed as the sensor main body 40 which is the height detection sensor according to the present modification.

Figure 32:
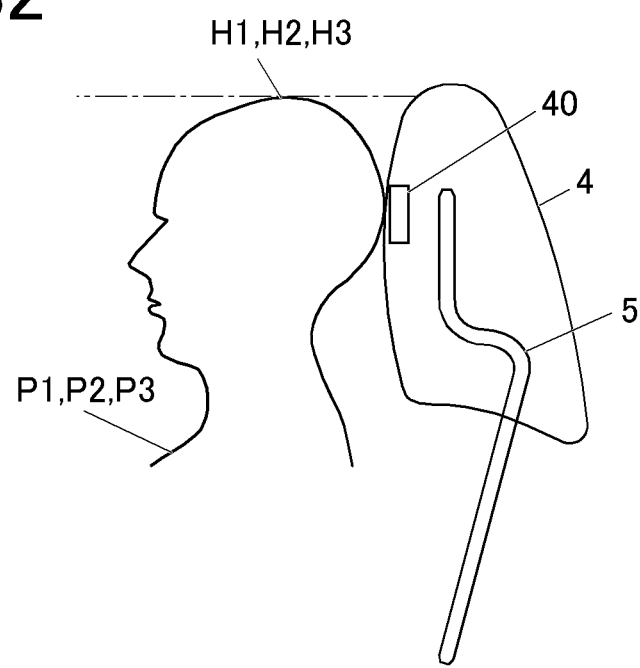
FIG. 32 is a diagram showing a modification when a pressure sensor is included as the sensor main body.

As shown in FIG. 32, the sensor main body 40 is positioned to be embedded in the cushion pad 4*a* of the headrest 4.

The sitting height detection sensor according to the present modification is positioned to be embedded in the cushion pad 4*a* and the cushion pad 4*a* is also supported by the headrest pillar 5. Therefore, the sitting height detection sensor is supported by the headrest pillar 5 indirectly through the cushion pad 4*a*.

The shape of the heads H1 to H3 is round. Therefore, there is a point in the back of the head which is most projected to the rear. The sensor main body 40 which is the pressure sensor is positioned to correspond to this point of the back of the head (for example, center of the headrest 4 in the width direction). When the sensor main body 40 which is the pressure sensor detects the pressure of the heads H1 to H3, the information is converted to an electric signal and output to the control apparatus 10.

Based on a head top position estimating program stored in the storage, the control apparatus 10 estimates the position of the height of the top of the head in the heads H1 to H3 of the persons P1 to P3 seated in the seat 1. With this, the sitting height of the persons P1 to P3 seated in the seat 1 can be detected (measured).

According to the present modification, the effects similar to the above-described embodiment can be achieved, and the detection of the sitting height is performed by the pressure actually pressed by the heads H1 to H3 of the persons P1 to P3. Therefore, the accuracy when the sitting height is detected hardly decreases compared to when the non-contact sensor is employed. That is, other members such as the cushion pad 4*a* and the outer layer 4*b* do not interfere.

[Modification 10]

Figure 33:
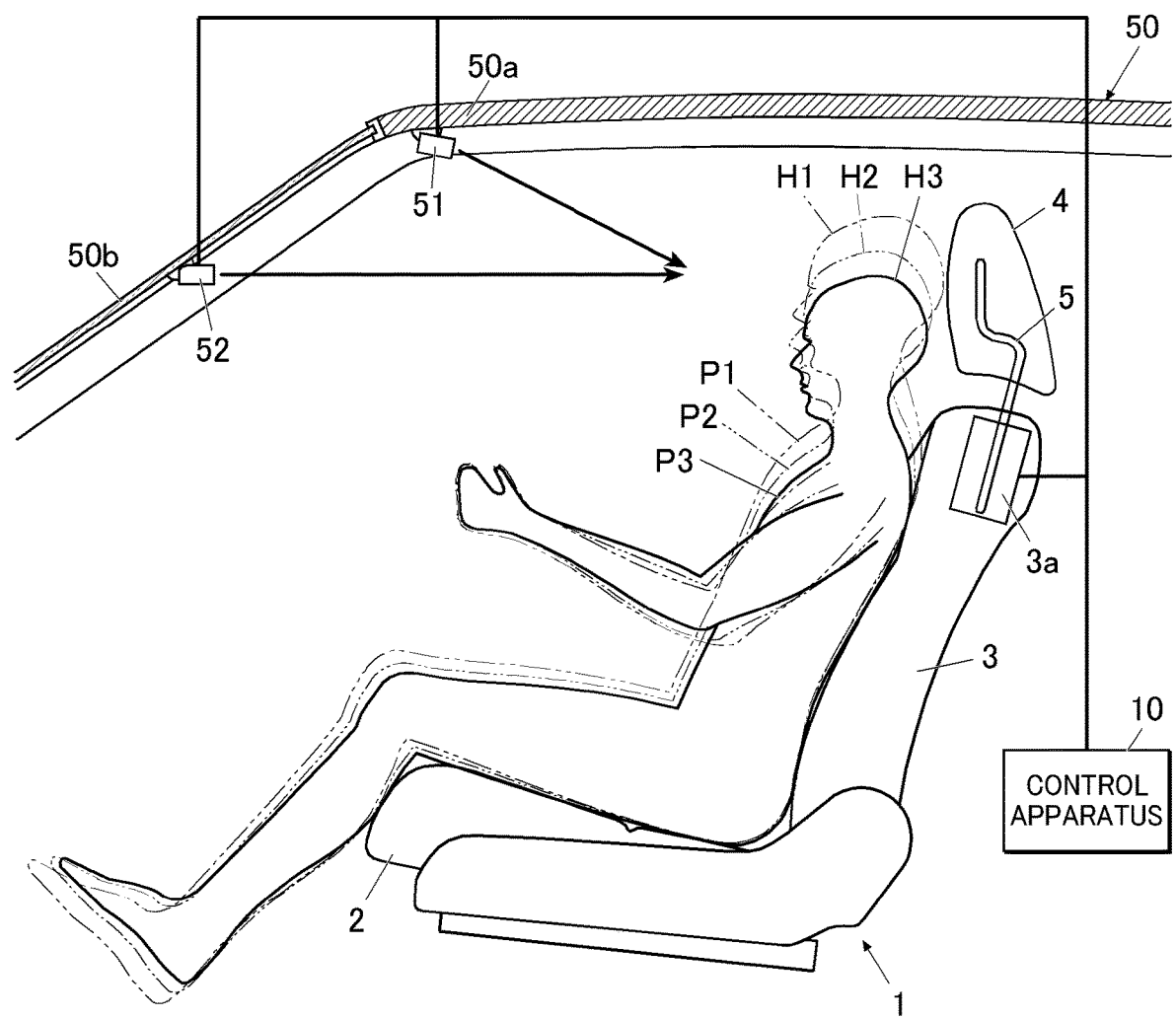
FIG. 33 is a diagram showing a modification regarding a sitting height detection sensor including a first detector and a second detector.

The sitting height detection sensor according to the present modification includes at least one of a first detector 51 and a second detector 52 provided on a vehicle body 50 as shown in FIG. 33. According to the present modification, both the first detector 51 and the second detector 52 are provided.

The vehicle body 50 includes a roof panel 50*a* positioned above the seat 1, and a window 50*b* positioned in front of the seat 1. The window 50*b* includes a window glass (windshield) fitted in a window frame.

The first detector 51 and the second detector 52 are connected to the control apparatus 10 to be able to communicate. The first detector 51 and the second detector 52 convert the detected information to an electric signal and output the signal to the control apparatus 10.

The first detector 51 is attached to the lower surface (that is, the ceiling surface) of the roof panel 50*a* in the vehicle body 50, and the second detector 52 is attached to the inner side surface of the window 50*b* in the vehicle body 50. Preferably, the positions of the first detector 51 and the second detector 52 in the left are right direction are close to directly front of the headrest 4 as much as possible in a range which does not interfere with the field of view.

A laser distance meter which measures the distance from the attached position to the measurement target is used as the first detector 51 and the second detector 52. Such laser distance meter irradiates a laser beam to the headrest 4, captures the beam reflected on the headrest 4 side, and calculates the distance.

The first detector 51 and the second detector 52 can change the angle in the up and down direction. The angle change of the first detector 51 and the second detector 52 is performed automatically according to control by the control apparatus 10.

The control apparatus 10 stores in advance the information regarding the distance from the first detector 51 and the second detector 52 to a plurality of points on the surface of the headrest 4.

When the sitting height is detected by the first detector 51 and the second detector 52 which are laser distance meters, the emitted laser beam measures the distance when the light is reflected at a position closer than the surface of the headrest 4, and the position in the up and down direction with the highest value in the measured position information is detected as the sitting height.

The control apparatus 10 operates the pillar driver 3*a* based on the electric signal output from the first detector 51 and the second direction 52 and controls the headrest pillar 5 to move up and down. The headrest pillar 5 can be moved up and down to adjust the headrest 4 to the optimal position.

The head of the person is round and if the distance to a plurality of points is measured along the head by the plural first detector 51 and the second detector 52, the highly accurate detection result can be obtained.

According to the present modification, both the first detector 51 and the second detector 52 are used, but at least one may be used, and in this case also, if the distance to a plurality of points is measured along the head, a highly accurate detection result can be obtained.

According to the present modification, the laser distance meter is used as the first detector 51 and the second detector 52, but the device is not limited to the above and a camera can be used.

Preferably, the camera to be used includes a face recognition function. The face recognition function recognizes the position of the eyes (eye point) and the forehead of the person. The position of the top of the head is calculated by the control apparatus 10 based on the position information, and with this, the sitting height can be detected.

According to the present modification, it is possible to provide a specific attachment structure which enables the sitting height detection sensor (first detector 51 and second detector 52) to detect the sitting height. The sitting height detection sensor (first detector 51 and second detector 52) is attached to the vehicle body 50, and the supporting rigidity of the sitting height detection sensor can be enhanced (first detector 51 and second detector 52).

[Modification 11]

A body pressure distribution sensor is used as the sitting height detection sensor according to the present modification. Although not shown, the body pressure distribution sensor is a thin sheet shape, and is provided on the rear side of the outer layer of the seat cushion 2 and the seat back 3 (between the cushion pad and the outer layer).

Specifically described, the seat shaped body pressure distribution sensor is provided entirely on the upper surface of the cushion pad in the seat cushion 2, and is provided entirely on the front surface of the cushion pad in the seat back 3.

Figure 34:
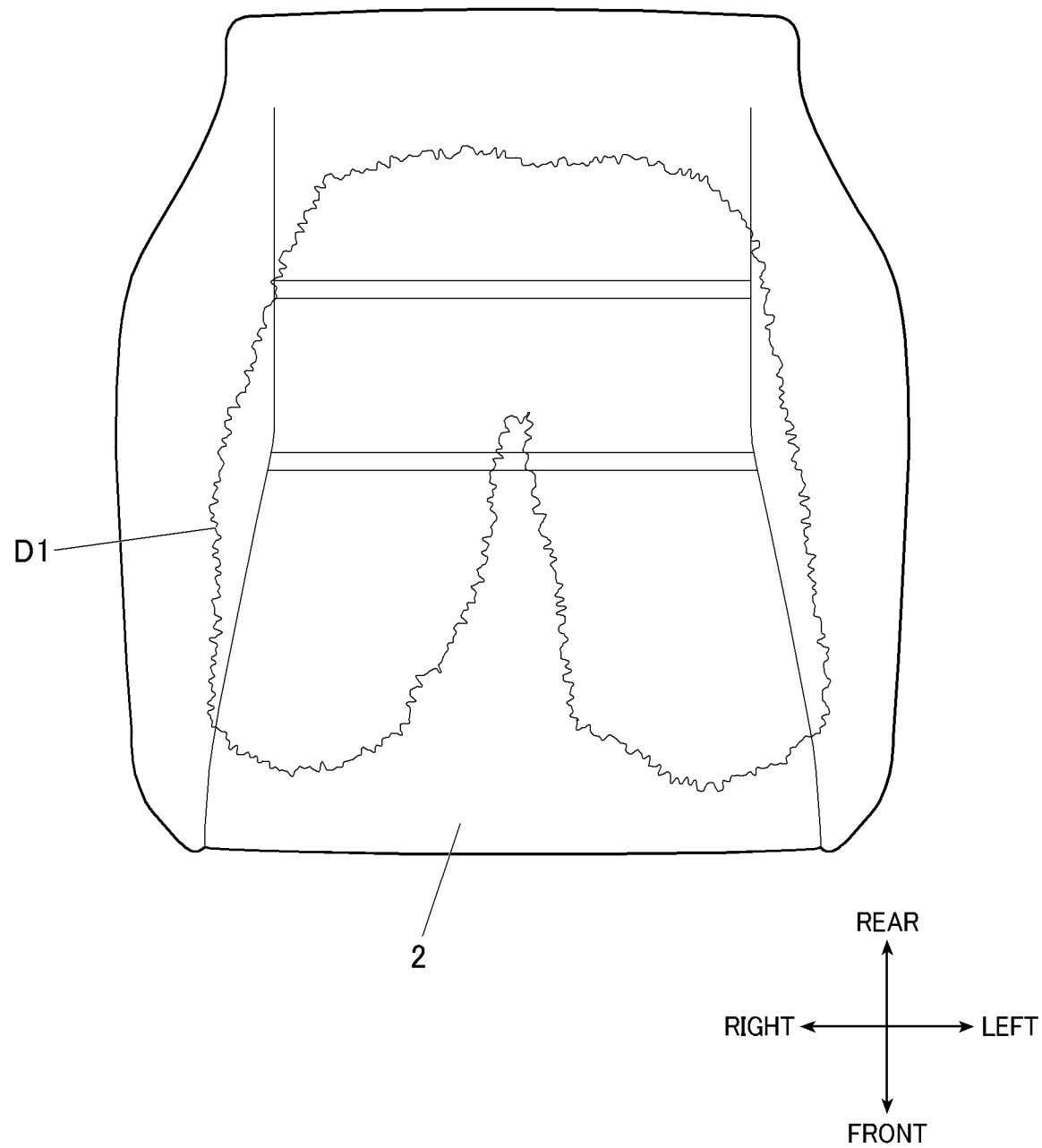
FIG. 34 is a diagram showing a modification when a sitting height is estimated from body pressure distribution information.
Figure 35:
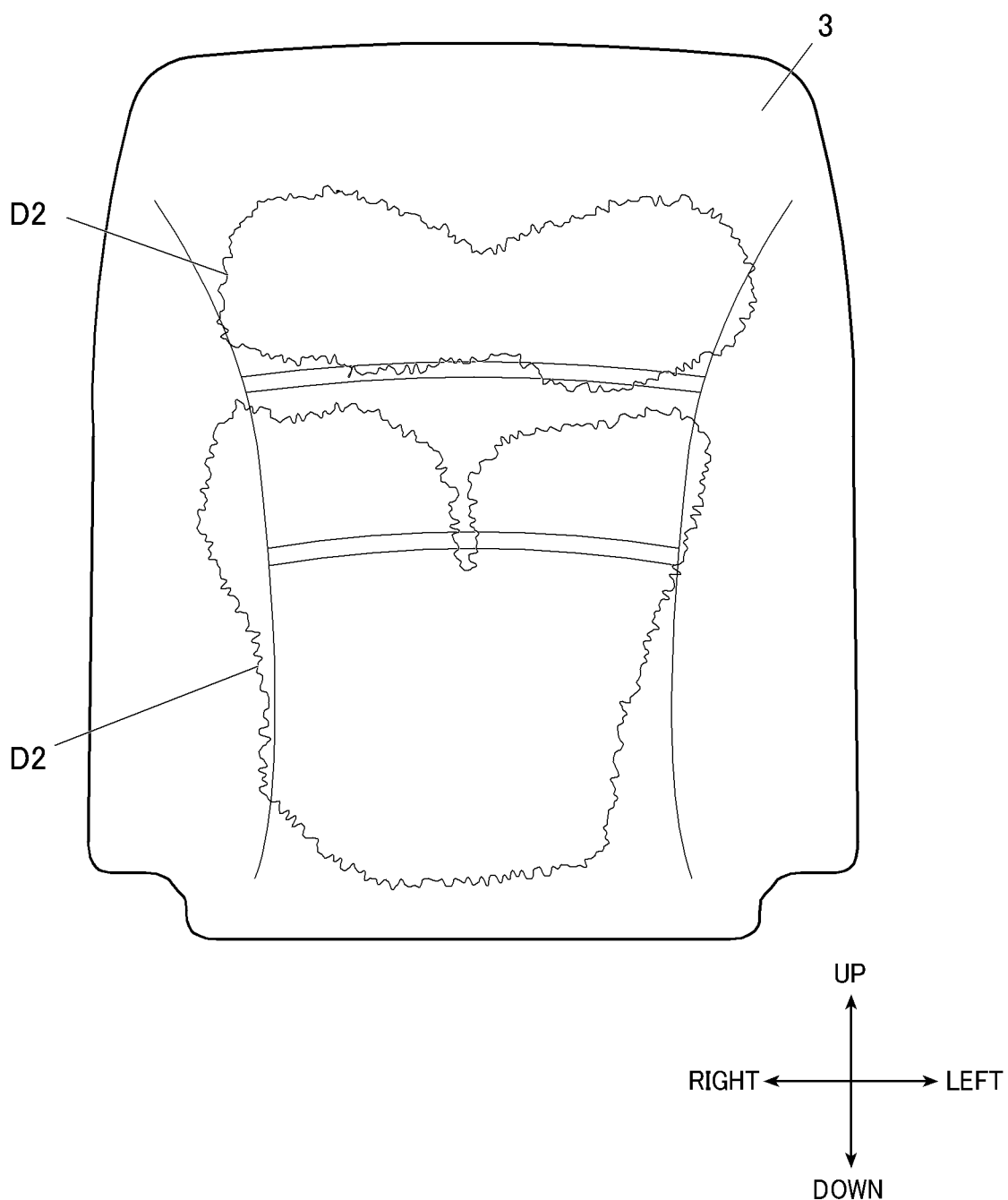
FIG. 35 is a diagram showing a modification when a sitting height is estimated from body pressure distribution information.
Figure 36:
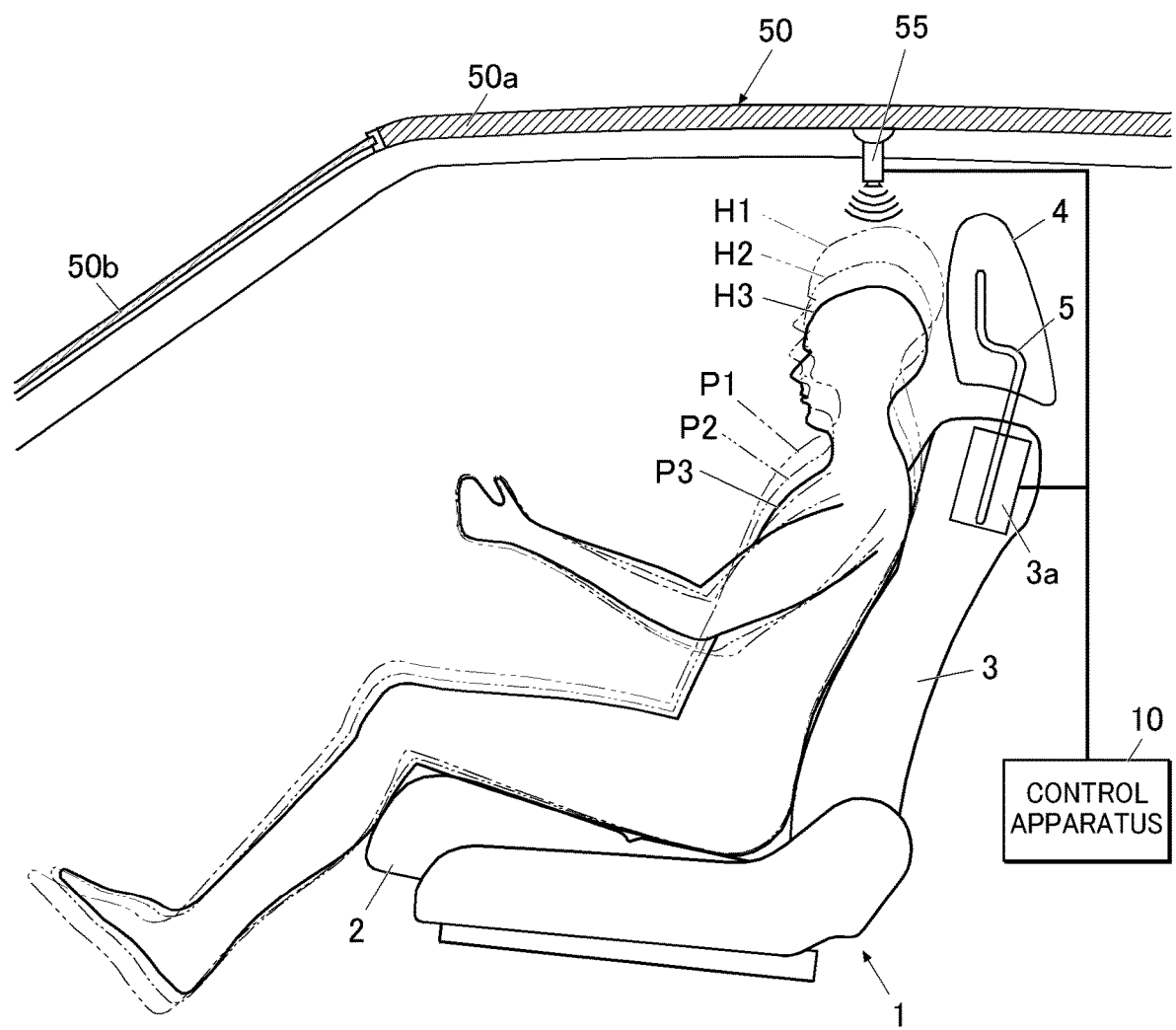
FIG. 36 is a diagram showing a modification when an ultrasound sensor is used as a sitting height detection sensor.

When the body pressure distribution of the person seated in the seat 1 is detected by the body pressure distribution sensor, in the seat cushion 2 portion, the body pressure distribution D1 for the buttock and the thigh of the person can be detected as shown in FIG. 34, and in the seat back 3, the body pressure distribution D2 of the back of the person can be detected as shown in FIG. 35.

The body pressure distribution sensor is connected to the control apparatus 10 to be able to communicate with each other. The body pressure distribution sensor converts the electric signal to the detected information and outputs the signal to the control apparatus 10. The control apparatus 10 suitably calculates the obtained body pressure distribution information and obtains the sitting height.

The posture of the person seated in the seat 1 can be obtained at a certain degree from the position of the buttock and the body pressure distribution information of the back of the person and the above can be suitably corrected when the sitting height is obtained.

According to the present modification, it is possible to provide a specific attachment structure which enables the sitting height detection sensor (body pressure distribution sensor) to detect the sitting height. The sitting height detection sensor (body pressure distribution sensor) is provided throughout the entire surface of the cushion pad on the occupant side on the rear side of the outer layer of the seat 1. Therefore, it is easy to obtain the body pressure distribution information and the sitting height detection accuracy can be enhanced.

[Modification 12]

An ultrasound sensor 55 is used as the sitting height detection sensor according to the present modification. The ultrasound sensor 55 emits the ultrasound with a wave transmitter to the target and the reflected wave is received by the wave receiver. With this, the ultrasound sensor 55 detects whether the target exists and detects the distance to the target. The head of the person is to be the target.

The ultrasound sensor 55 according to the present modification is attached to the lower surface (that is, the ceiling surface) of the roof panel in the vehicle body 50. The ultrasound sensor 55 is positioned toward the front than the headrest 4, and preferably, is positioned above the top of the head of the occupant.

The ultrasound sensor 55 is connected to the control apparatus 10 to be able to communicate with each other. The detected information is converted to the electric signal and output to the control apparatus 10.

The ultrasound sensor 55 is configured to be able to change the angle in the front and rear direction. The angle change of the ultrasound sensor 55 is automatically performed according to control by the control apparatus 10.

The control apparatus 10 stores in advance the information regarding the distance to the plurality of points on the upper surface of the seat cushion 2 from the ultrasound sensor 55.

When the sitting height is detected by the ultrasound sensor 55, the distance when the emitted ultrasound is reflected at a position closer than the upper surface of the seat cushion 2 is measured, and the position in the up and down direction with the highest value in the measured position information is detected as the sitting height.

The control apparatus 10 operates the pillar driver 3a based on the electric signal output from the ultrasound sensor 55 and controls the headrest pillar 5 to move up and down. The headrest pillar 5 is moved up and down and the headrest 4 can be adjusted to the optimal position.

According to the modification, the ultrasound sensor 55 is provided on the roof panel 50a but the position is not limited to the above. The ultrasound sensor 55 is provided on the window 50b and is able to detect the position of the height of the top of the head of the occupant by emitting the ultrasound toward the surface of the headrest 4.

According to the modification, it is possible to provide a specific attachment structure which enables the sitting height detection sensor (ultrasound sensor 55) to be able to detect the sitting height. The sitting height detection sensor (ultrasound sensor 55) is attached to the vehicle body 50, and the supporting rigidity of the sitting height detection sensor (ultrasound sensor 55) can be enhanced.

Configuration Example

Below, the configuration examples which can be combined with the above-described embodiment and modifications are described. The configuration example can be combined if possible.

Common reference numerals are applied to the elements of the configuration examples which are common with the above-described embodiments and modifications and the description is omitted or simplified.

<Configuration 1>

[Regarding Driving Position]

Here, the driving position refers to the posture in driving and the position in which a good field of view is always maintained during driving and the steering wheel and the pedal can be operated with a feeling as one with the vehicle.

The driving position can be suitably changed by the control apparatus 10 controlling the units in the seat 60A.

Figure 37:
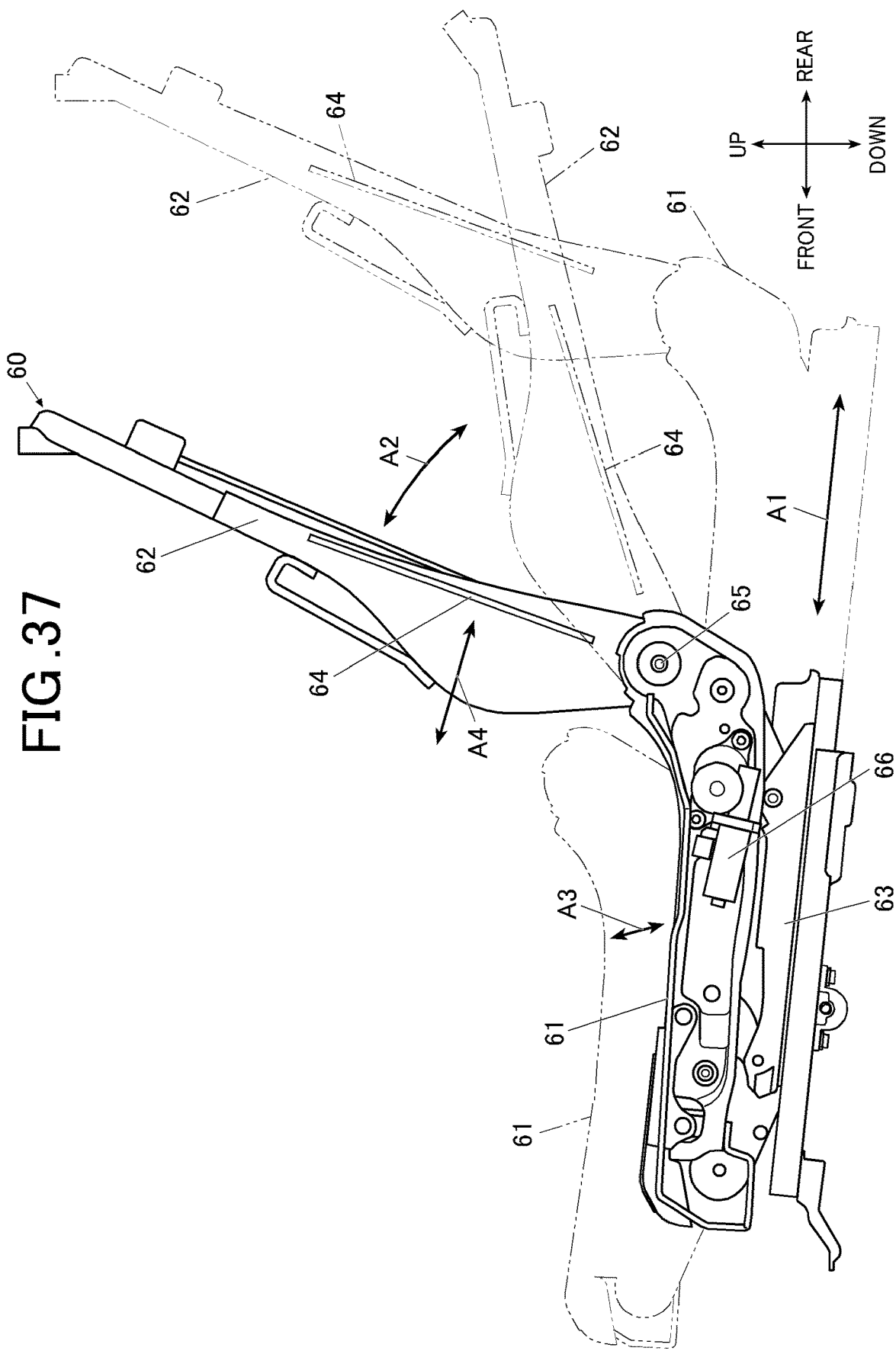
FIG. 37 is a diagram showing a configuration example regarding adjustment of a driving position.
Figure 38:
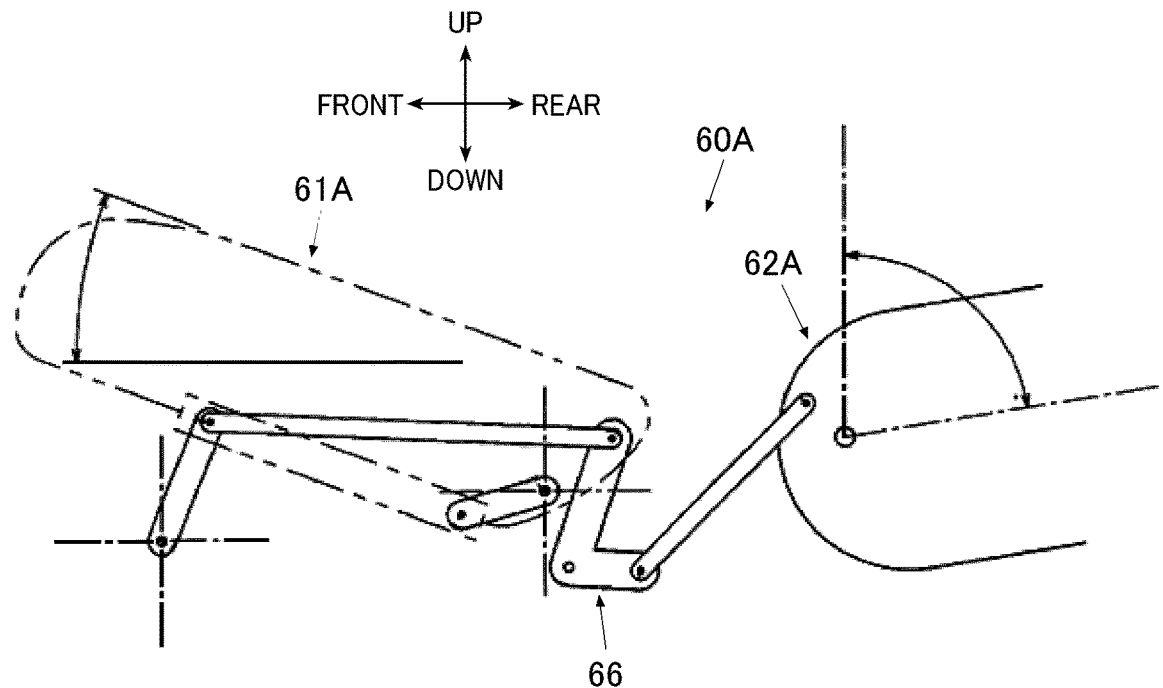
FIG. 38 is a diagram showing a configuration example regarding the adjustment of the driving position.

As shown in FIG. 37 and FIG. 38, the seat 60A according to the present configuration example includes a seat frame 60 which is the skeleton of the seat 60A. Various mechanisms (including seat posture adjustment apparatus 15) which are controlled by the control apparatus 10 and which deform the shape of the seat 60A are provided in the seat frame 60 so that the person seated in the seat 60A is in the suitable driving position.

Described in detail, the seat frame 60 includes a cushion frame 61 which is to be the skeleton of the seat cushion 61A and the back frame 62 which is to be the skeleton of the seat back 62A. Various mechanisms described above are provided surrounding the cushion frame 61 and the back frame 62.

As various mechanisms, the slide rail 63 is provided in the cushion frame 61. The slide rail supports the entire seat 60A on the floor and slides and moves the seat 60A in the front and rear direction (see arrow A1).

A lumbar support 64 is provided in the back frame 62. The lumbar support 64 takes the force caused by the occupant leaning on the seat back 62A and transmits the force to the back frame 62. Then, the shape of the portion in contact with the lower back of the occupant is changed to change the support state of the lower back according to the preference of the occupant. That is, the lumbar support 64 is configured to deform in the front and rear direction (see arrow A4).

Further, a reclining mechanism 65 is provided between the rear edge of the cushion frame 61 and the lower edge of the back frame 62 to change the angle of the back frame 62 with relation to the cushion frame 61 (see arrow A2).

A height mechanism 66 is provided in the cushion frame 61 to move the seat cushion 61A in the up and down direction (see arrow A3). The height mechanism 66 not only moves the seat cushion 61A up and down as shown in FIG. 37 but also adjusts the position of the front edge and the rear edge of the seat cushion 61A in the up and down direction as shown in FIG. 38. The height mechanism 66 shown in FIG. 38 includes the link mechanism to adjust the position of the front edge and the rear edge of the cushion frame 61 in the up and down direction.

The back frame 62 is in a state linked to the cushion frame 61 through the reclining mechanism 65. Therefore, the back frame 62 moves in the up and down direction with the cushion frame 61 by the height mechanism 66.

Further, the back frame 62 may include a middle fold mechanism which tilts the portion in the middle in the up and down direction to the front and rear direction in the back frame 62 in the raised up state. If such back frame 62 included in the middle fold mechanism is used in the seat 60A, the upper portion of the upper half of the body of the person seated in the seat can be raised while the person leans on the seat back 62A. Therefore, the field of view to the front is secured while in a relaxed reclined state.

When the driving position of the seat 60A is adjusted, some or all of the various mechanisms can be operated at the same time or the mechanisms can be operated sequentially one by one.

For example, preferably, the shape of the seat 60A is changed in the following order, the front and rear position of the seat 60A is adjusted by the slide rail 63, the angle of the seatback 62A is adjusted by the reclining mechanism 65, and the height adjustment of the seat 60A is performed by the height mechanism 66, and then the front and rear position of the lower back is adjusted by the lumbar support 64.

According to the configuration example, the control apparatus 10 can automatically change the driving position according to the vehicle class and the driving condition of the vehicle in which the seat 60A is provided.

That is, the vehicle class of the vehicle (for example, SUV/mini-van, sedan, and sports car type) in which the seat 60A is provided and the driving condition (for example, period of time of day, weather, state of roads, etc.) are selected according to the determination by the occupant. The control apparatus 10 calculates the optimal driving position based on the selection by the occupant and the physique of the person seated in the seat, and controls the change of the shape of the seat 60A.

Further, a mode change button (not shown) which starts the mode change can be provided in the vehicle so that the change of the shape of the seat 60A can be started according to the will of the person seated in the seat. Such mode change button can change to the position of the sports mode, the position of the relax mode, and the like.

The sports mode is a mode which changes the seat 60A of the vehicle to a shape preferable for driving a sports car. The shape preferable for driving the sports car is, for example, enhancing the hold and the stability in cornering by adjusting the angle of the side support (bank) in the seat cushion 61A and the seat back 62A or lowering the height to make the eye level closer to the road.

The relax mode is a mode which changes the seat 60A of the vehicle to the shape so as to be able to sit in a relaxed state. Described in detail, the relax mode is a mode in which the shape of the seat 60A is changed so that the seat back 62A is reclined (tilted rotated to the rear), by moving the front edge of the seat cushion 61A upward with relation to the rear edge as shown in FIG. 38.

The seat other than the driver's seat can be set to the relax mode at any time, but as for the seat 60A which is the driver's seat, the relax mode can be selected only during automated driving of the vehicle. The automated driving of the vehicle is automated driving at a high level or complete automated driving corresponding to "level 4" in the automated level determined by National Highway Traffic Safety Administration (NHTSA) "level 4" or "level 5" in the automated level determined by Society of Automotive Engineers (SAE) of the United States.

Configuration Example 2

[Body Width Adjustment]

The seat 70 according to the present configuration example includes a seat cushion 71 and a seat back 72. An air cell 74 is embedded in at least one of the seat cushion 71 and the seat back 72 to perform the adjustment of the body width to match the body width of the occupant.

Here, body width means the width of the body of the occupant, and the width near the lower back when the occupant is seated in the seat 70.

Figure 39:
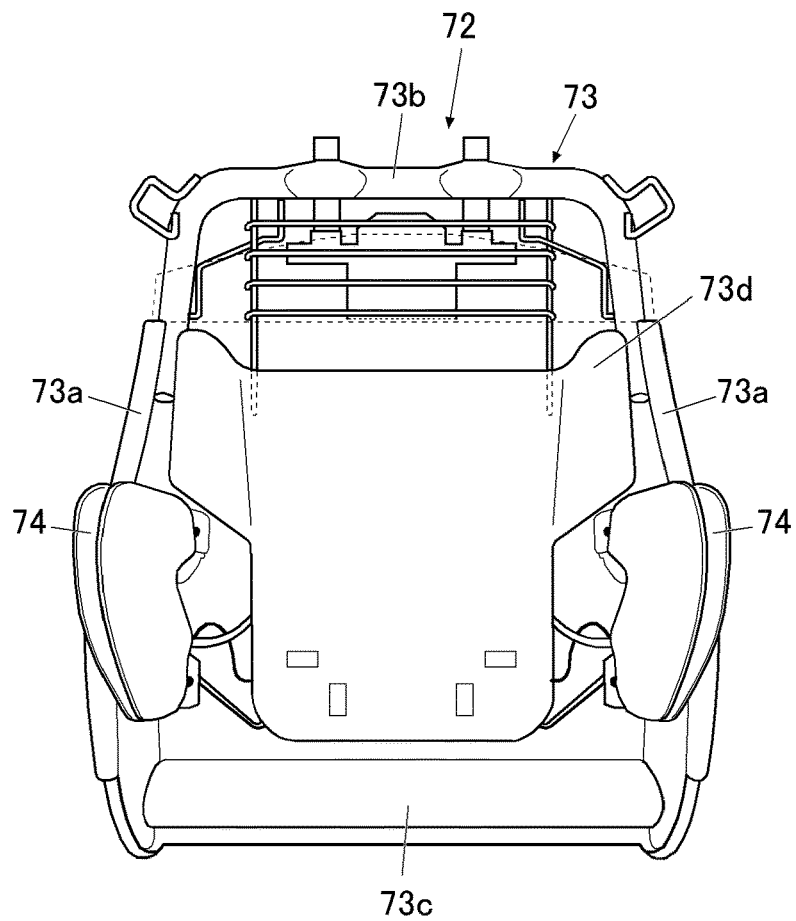
FIG. 39 is a diagram showing a configuration example regarding adjustment of a body width.

According to the present configuration, as shown in FIG. 39, the air cell 74 is embedded in at least the seat back 72.

The seat back 72 includes the back frame 73 including the skeleton of the seat back 72. The back frame 73 includes a pair of left and right back side frames 73a and 73a, an upper portion frame 73b linking the upper edges of the pair of left and right back side frames 73a and 73a, and a lower portion frame 73c linking the lower edges of the pair of left and right back side frames 73a and 73a. Further, between the pair of left and right back side frames 73a and 73a, a lumbar support 73d which supports the lower back of the occupant is provided.

Then, a fluid (here air, but can be liquid) is sealed inside on the inner side of each of the pair of left and right back side frames 73a and 73a, and an air cell 74 in an inflating bag shape is provided. The air cell 74 is connected to an air compressor (not shown) which is the supply source of air.

Although not shown, an internal pressure sensor which measures the internal pressure of the air cell 74 can be provided in the air cell 74. Instead of the internal pressure sensor, the pressure sensor which measures how much pressure is applied to the occupant can be provided.

The air cell 74 is provided on the rear side of the outer layer of the seat back 72, and the air cell 74 is provided to the left and right side supports 72a (bank) inflated to the front in the seat back 72.

When the adjustment of the body width is performed with such air cell 74, this is performed in a state with the person seated in the seat 70. When the air is inserted in the air cell 74 and gradually inflated with the arm of the person raised, the air cell 74 gradually comes into strong contact with a flank of the occupant through the outer layer. When the air cell 74 comes into contact with the occupant through the outer layer and the pressure measured by the pressure sensor becomes a suitable value, the sending of the air from the air compressor stops, and the inflated state is maintained.

With this, the interval between the left and right side supports 72a can be adjusted to the dimensions optimal for the body width of the occupant. The air cell 74 comes into contact with the flank of the occupant through the outer layer, and the state in which the predetermined pressure value is obtained by the pressure sensor can be the width of the body of the occupant seated in the seat. That is, the body width of the occupant can be estimated.

According to the above, the position where the air cell 74 is set is near the lower back of the person seated in the seat 70. However, the position is not limited to near the lower back, and the air cell 74 can be provided in various locations of the seat 70.

Figure 40:
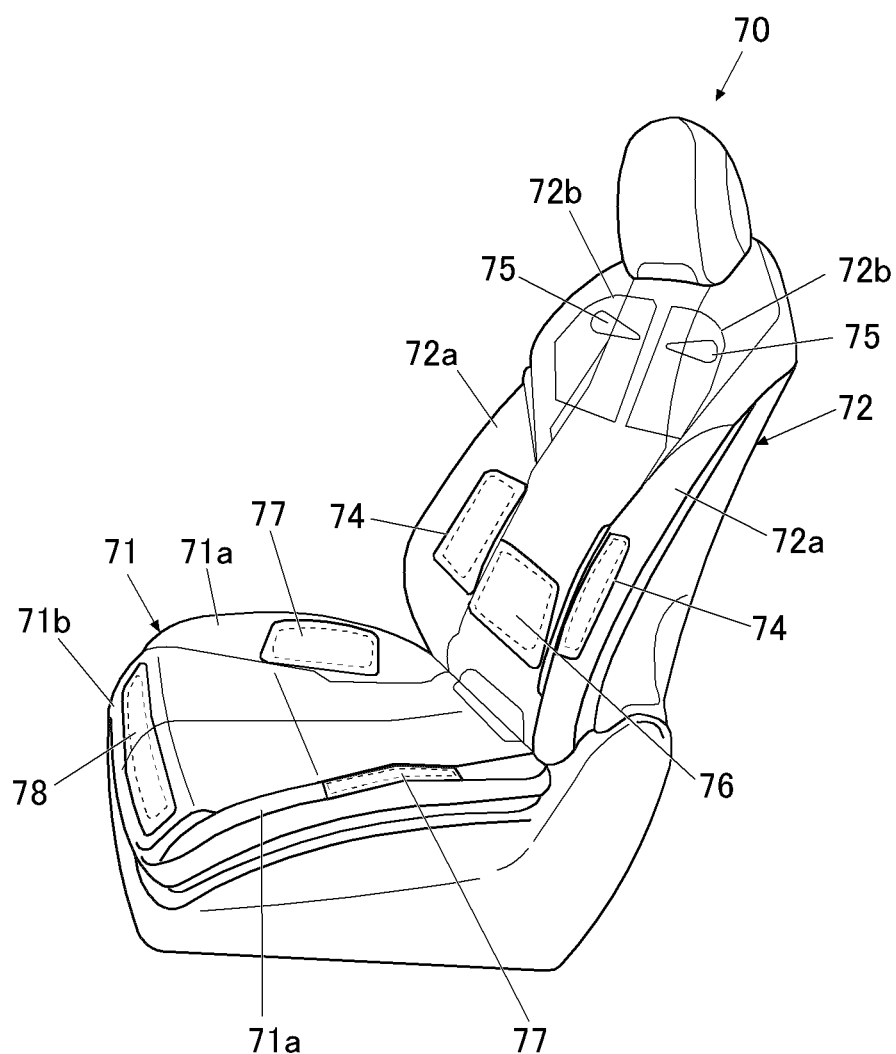
FIG. 40 is a diagram showing a configuration example regarding the adjustment of the body width.

FIG. 40 is a perspective view showing the entire seat 70. According to the present example, the air cells 74 to 78 are provided in various locations of the seat 70.

A shoulder support 72b which supports the shoulder of the person seated in the seat 70 is provided in the seat back 72 of the seat 70 as shown in FIG. 40. The shoulder support 72b includes the air cell 75, and the air cell 75 includes the function to push the shoulder of the seated person inward in the width direction and downward by inflating.

The air cell 76 is provided corresponding to the position of the lumbar support 73d in the seat back 72. The air cell 76 includes the function to press the back side of the lower back of the person seated in the seat 70 forward.

That is, near the lower back, the lower back of the occupant is supported from three directions by left and right air cells 74 and a back side air cell 76. In order to achieve the optimal support for the lower back, the supporting pressure by the left and right air cell 74 is suitably adjusted according to the inflating amount of the air cell 76 on the rear side.

Further, a side support 71 which inflates upward is provided on both edges in the width direction of the seat cushion 71, and these side supports 71a each include the air cell 77. Such air cells 77 include the function to press the buttock and the thigh of the person seated in the seat 70 to the inner side in the width direction by inflating.

On the front edge of the seat cushion 71, an ottoman 71b is provided as a below knee supporter which supports the portion of the foot of the seated person below the knees. Such ottoman 71b includes the air cell 78 positioned in the front edge of the seat cushion 71. The ottoman 71b includes the function to support the portion below the knee in the foot of the seated person from below by inflating the air cell 78.

The air cells 74 to 78 embedded in the seat 70 estimates the body width from the physique information obtained by a physique measuring unit embedded in the seat to measure a physique of the occupant (for example, various locations such as height, weight, sitting height, length of leg). The air cells 74 to 78 are suitably operated under the control of the control apparatus 10 based on the estimated result. The physique information does not have to be obtained by the physique measuring unit, and can be obtained by input of the information on the control apparatus 10 by the occupant.

When the operation of the air cells 74 to 78 is controlled by the control apparatus 10, the pressure is automatically controlled to the optimal pressure, and the width dimensions are automatically controlled to be optimal according to the driving condition and the physique of the occupant.

Configuration Example 3

[Measurement of Weight]

The seat according to the present configuration includes a load sensor W and the weight of the person seated in the seat can be measured.

Figure 41:
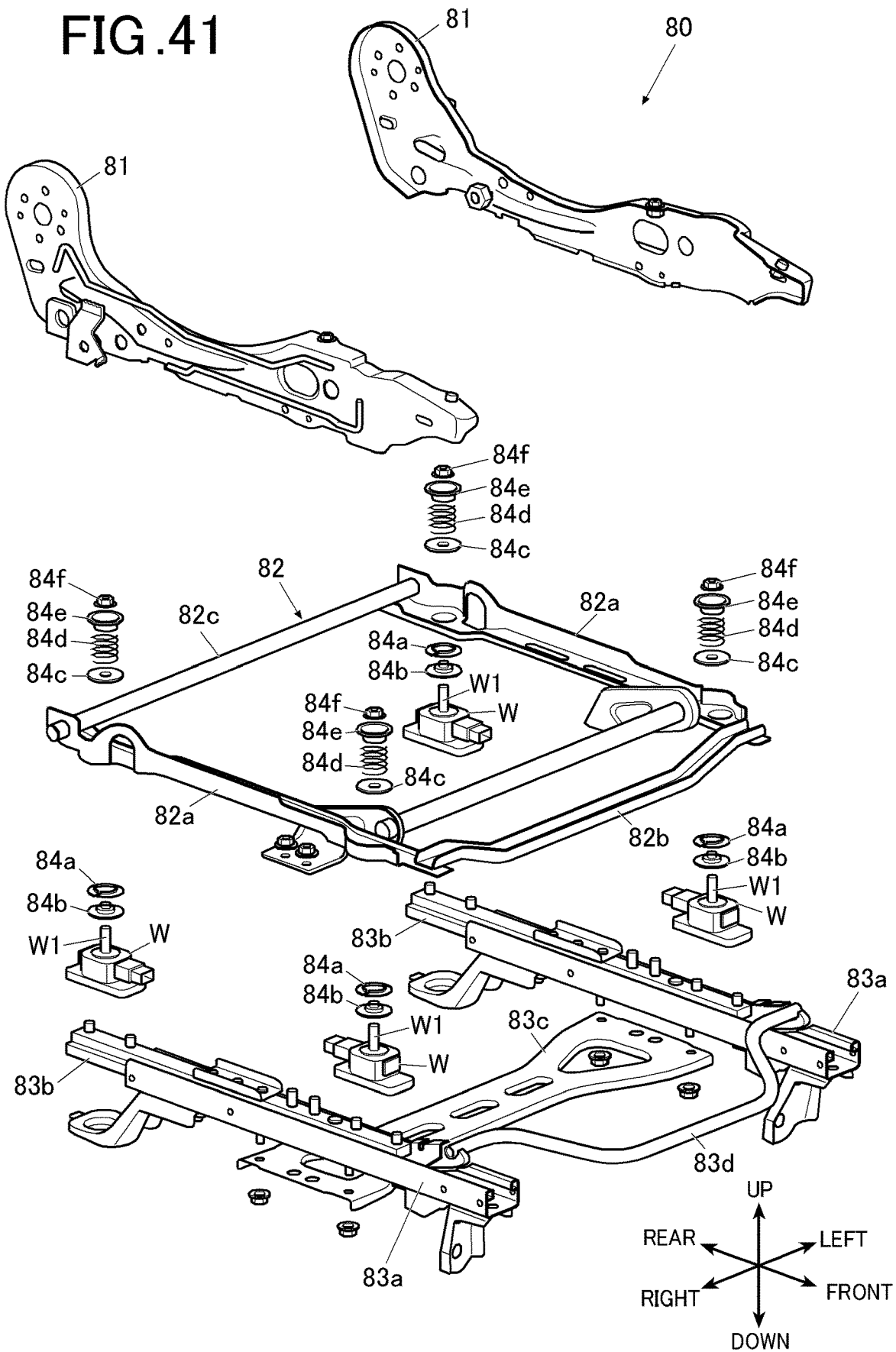
FIG. 41 is a blown-up perspective view showing a cushion frame provided with a load sensor.

The seat includes a cushion frame 80 which is the skeleton of the seat cushion, and the load sensor W is embedded in the cushion frame 80 as shown in FIG. 41.

The cushion frame 80 includes a pair of left and right cushion side frames 81 and 81, a rectangular frame 82 attached to the lower edge of the pair of left and right cushion side frames 81 and a pair of left and right slide rails 83 attached to the lower edge of the rectangular frame 82.

The load sensor W is provided between the rectangular frame 82 and the pair of left and right slide rails 83.

The rectangular frame 82 includes a pair of left and right beams 82a, a front beam 82b, and a back pipe 82c. The above frame materials are linked in a rectangular shape from a planar view. The rectangular frame 82 includes the function to evenly transmit the load of the occupant transmitted from the pair of left and right cushion side frames 81 to the load sensor W.

The front beam 82b is provided between the front edges of the pair of left and right beams 82a, and the front edges of the pair of left and right beams 82a are linked.

The back pipe 82c is provided between the rear edges of the pair of left and right beams 82a and the rear edges of the pair of left and right beams 82a are linked.

The pair of left and right slide rails 83 each includes a lower rail 83a supported by the leg portion provided in the front and rear edges and an upper rail 83b hooked to the lower rail 3 to be able to slide with relation to the lower rail 3 on the lower rail 3 in the front and rear direction.

The pair of left and right slide rails 83 are formed as one by the lower bracket 83c placed across the left and right lower rail 3 fixed on the lower surface of the left and right lower rail 3. A lock mechanism 83d is provided in the pair of left and right slide rails 83 to lock and to release the lock for the upper rail 83b with relation to the lower rail 83a.

A total of four load sensors W are provided in the front edge and the rear edge of the left and right upper rails 83b. These are fixed to the upper surface of the upper rail 83b by fixing members such as a nut and a bolt.

The rectangular frame 82 is placed on the load sensor W through a bush 84a and collar with stage 84b.

The beam 82a in the rectangular frame 82 includes a bottom plate formed in a L shape from a cross-sectional view. A through hole passing a rod W1 projecting upward in the load sensor W is formed in the bottom plate. The rod W1 passed through the through hole is provided with a flat washer 84c, a wrapping spring 84d and a spring holder 84e all formed in a ring shape.

A nut 84f is provided in the rod W1, and the pair of left and right slide rails 83 and the rectangular frame 82 are linked through the load sensor W. The pair of left and right cushion side frames 81 are joined by welding to the rectangular frame 82.

According to the seat including the cushion frame 80 configured as described above, it is possible to measure the weight of the person seated in the seat. That is, the load sensor W converts the information regarding the detected load to the electric signal and outputs the signal to the control apparatus 10. The control apparatus 10 is able obtain the weight of the person seated in the seat based on the obtained information.

The load sensor W is provided below the four corners of the rectangular frame 82 which supports the pair of left and right cushion side frames 81. Therefore, for example, compared to when the load sensor W is not provided in the four corners, the load detection accuracy by the four load sensors W can be enhanced.

Further, the four load sensors W are used and the balance of sitting of the person seated in the seat can be detected. That is, various detection results can be obtained, for example, the load sensor W with the largest load applied among the first to four load sensors W or the difference between the normal driving and the cornering. Such detection result can be reflected on the change in the shape of the seat and the control regarding the link with the vehicle body side by the control apparatus 10.

In addition to the program which obtains the weight information from the information detected by the load sensor W, the storage 12 in the control apparatus 10 stores various programs regarding measuring the weight.

As various programs regarding the weight measurement, the storage 12 stores, for example, a position correction program which corrects the driving position by calculating the BMI from the obtained weight information and the height information of the occupant input in the control apparatus 10.

Other than the above, the storage 12 stores a weight information transmitting program in which the control apparatus 10 can communicate with car navigation or an information terminal owned by the occupant, and the obtained weight information is transmitted. With this, the weight information can be visualized, and the occupant is able to confirm his own weight information.

Alternatively, the storage 12 may store an advice program in which the control apparatus 10 may be able to communicate with an external database for advice, and based on the obtained weight information, suitable advice data can be extracted from the external database. The advice regarding the weight is transmitted to the occupant (advice raising problems regarding the weight).

Configuration Example 4

[Regarding Information Terminal Operation]

Figure 42:
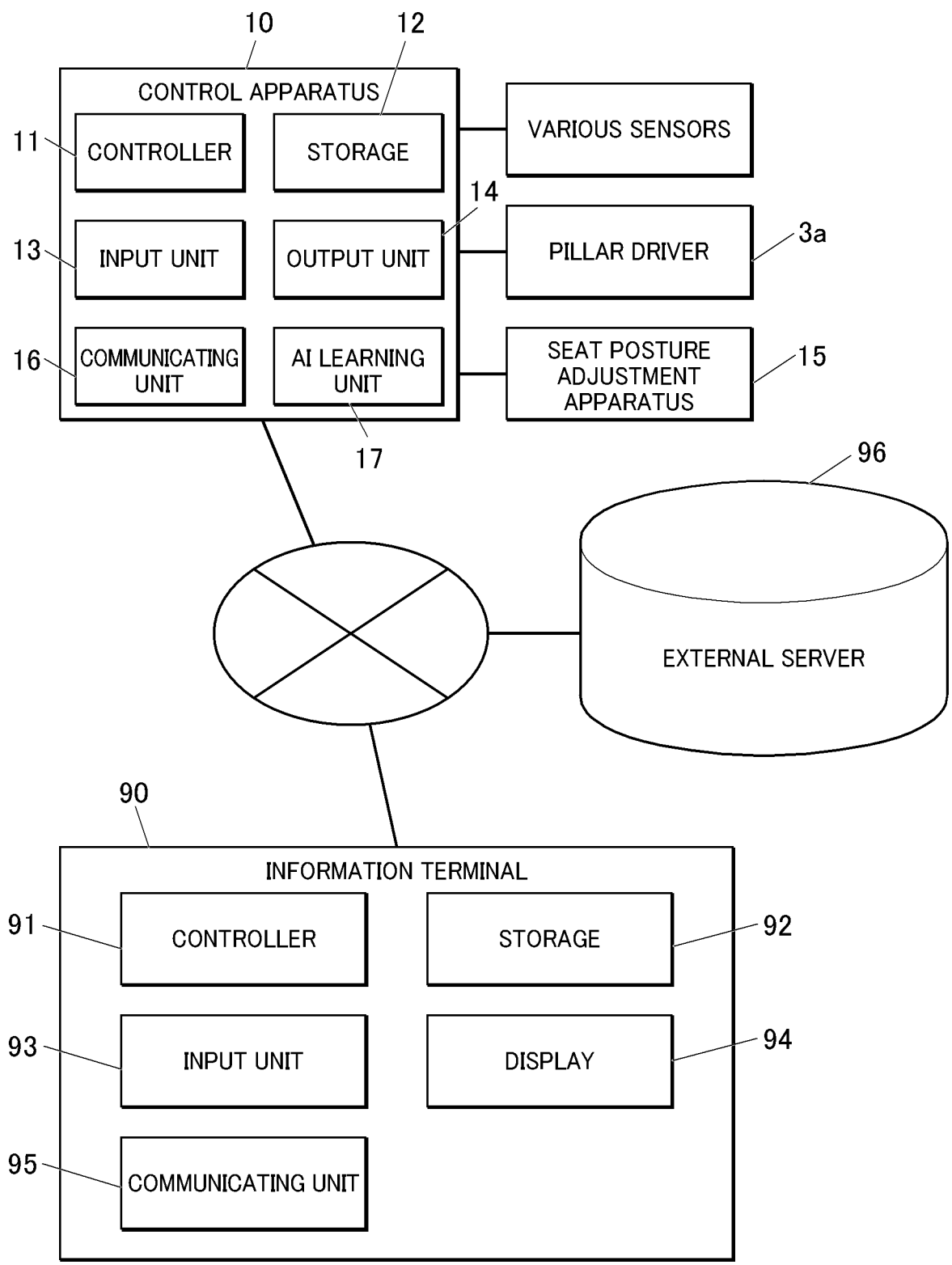
FIG. 42 is a block diagram showing a configuration of a seat posture adjustment system.

As shown in FIG. 42, the control apparatus 10 further includes a communicating unit 16. The control apparatus 10 is connected to be able to communicate with an information terminal 90 in which access to the control apparatus 10 is authorized.

The information terminal 90 is a computer such as a tablet terminal, a mobile terminal (including a smartphone), a personal computer or the like. The information terminal 90 performs bidirectional wireless communication with the control apparatus 10 on the vehicle side to be able to obtain information from the control apparatus or to be able to control the control apparatus 10. Such information terminal 90 includes a controller 91, a storage 92, an input unit 93, a display 94, and a communicating unit 95.

The controller 91 includes a Central Processing Unit (CPU) as the central processing apparatus. The controller 91 executes various calculation processes based on the program and data stored in the storage 92 and controls various units in the information terminal 90.

The storage 92 includes the storage apparatus such as a semiconductor memory or a magnetic disk apparatus and stores various programs or data. The storage 92 also functions as the work memory of the controller 91. The storage 92 includes the information storage medium which can be attached and detached such as the flash memory and the optical disk.

The input unit 93 includes the input apparatus such as the touch panel, keyboard, mouse, and the like, and receives the input of operation by the user (for example, occupant) operating the information terminal 90. The input unit 30 according to the present configuration example is a touch panel type input apparatus.

The display 94 displays a screen based on graphic data generated by the controller 91 and according to the present configuration example, the touch panel is employed as the input unit 93. Therefore, the touch panel is employed as the display 94. In addition to the above, a display apparatus such as a liquid crystal display apparatus can be suitably employed.

The communicating unit 95 includes a wireless communication circuit, and by transmitting and receiving the signal between the communicating unit 16 in the control apparatus 10, the bidirectional communication with the control apparatus 10 becomes possible. The communicating unit 16 in the control apparatus 10 and the communicating unit 95 in the information terminal 90 can communicate through any of the various computer networks or can communicate by ad hoc mode. The communication can be wired or wireless.

The information terminal 90 stores in the storage various input information regarding the seat and the vehicle provided with the seat. The information terminal 90 communicates with the control apparatus 10 through the communicating unit 95 and stores the various input information in the storage 12 of the control apparatus 10 also.

Specifically, when the person sits in the seat and the shape of the seat is changed, the shape change information can be stored in the storage 12 in the control apparatus 10 or the storage 92 in the information terminal 90.

The control apparatus 10 automatically performs the change in the shape of the seat based on the information of the person seated in the seat and the shape change information of the seat.

When the shape of the seat is changed, this is performed based on the input information from the information terminal 90. That is, the information terminal 90 is able to control the control apparatus 10 by wireless bidirectional communication with the control apparatus 10. Therefore, through the control apparatus 10, the information terminal 90 is able to control various sensors and the seat posture adjustment apparatus 15 connected to the control apparatus 10. Here, the devices which can be controlled by the information terminal 90 (for example, the above described slide rails 63 and 83, the lumbar support 64, the reclining mechanism 65, the height mechanism 66, the middle fold mechanism of the seat back, and the position adjustment mechanism of the front and rear edge in the height mechanism 66) are displayed on the display 94 of the information terminal 90. The device to be controlled can be selected on the touch panel of the information terminal 90 (input unit 93 and display 94).

Further, when the above devices are selected and the control apparatus 10 controls the operation, the physique information of the occupant seated in the seat can be input on the touch panel (input unit 93 and display 94) of the information terminal 90. Here, the physique information of the occupant can be input by a numeric value or as shown in FIG. 43, the physique information can be input by operating the computer graphics displayed on the screen of the touch panel.

Figure 43:
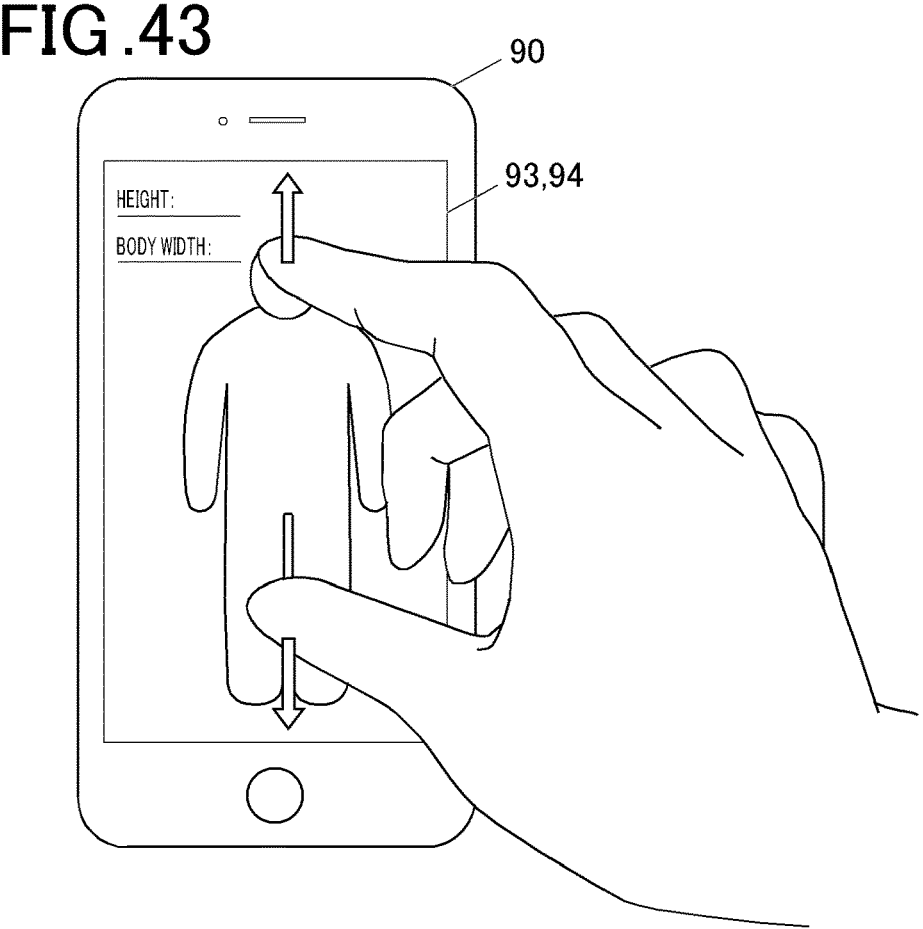
FIG. 43 is a diagram describing an example of an information input method using an information terminal.

According to the example shown in FIG. 43, the person displayed on the screen (computer graphics) is pinched out in the direction of the height to make the height higher and the height information is changed. Although not illustrated, the height information can be changed by pinching in to make the height smaller, and the person displayed on the screen can be pinched out or pinched in in a side direction to change the information of the body width. Other operation (for example, swipe operation or flick operation) can be performed to increase or decrease the weight, and the user displayed on the screen can be switched.

Another example in which the shape of the seat is changed automatically by the control apparatus 10 is a method to change the shape of the seat by registering the occupant information on the information terminal 90.

Described in detail, the occupant information includes information which specifies body information of the occupant such as height, weight, sitting height, leg length, arm length, body width, posture (inward curved back, outward curved back), BMI, body fat percentage, muscle mass, and the like. The above occupant information is stored in the storage 92 in the information terminal 90 in advance. The physique and the features of the person seated in the seat are estimated from the above occupant information, and by using the information obtained by the above estimate, the shape of the seat is changed to be the optimal state for the occupant.

When the body information of the occupant is changed, as described above, the body information can be adjusted on the touch panel of the information terminal 90 (see FIG. 43).

Moreover, the storage 92 stores a program to manage the health of the user (for example, a program similar to the above-described advice program) based on exercise information (frequency of exercise and content of exercise) and meal information (information regarding meals eaten daily) regarding the user input on the touch panel of the information terminal 90 and the information regarding the weight measured by the above described load sensor W, for example). By performing such program, the user is able to understand his state of health on the information terminal 90 and can manage his health at home according to the advice.

As shown in FIG. 42, the control apparatus 10 in the configuration example further includes an Artificial Intelligence (AI) learning unit 17 which learns information for each user regarding the change of the shape of the seat.

The AI learning unit 17 calculates the difference between the shape (position) of the seat set by the control apparatus 10 and the shape (position) of the seat adjusted by the user and stores the result in the storage 12. The shape of the seat optimal for the user can be stored in the storage 12 for each user, and when the user seated in the seat is specified, the shape of the seat can be changed to match the user. The AI learning unit 17 may store in the storage 12 the shape of the seat and at the same time store the position of the steering wheel and the mirror of the vehicle. The shape of the seat can be changed to match the user and at the same time, the position of the steering wheel and the mirror can also be changed.

When the user stores the shape of the adjusted seat, other additional conditions are stored in the storage 12 so that the AI learning unit 17 is able to learn the shape of the seat optimal for each user based on the stored data.

The additional conditions include, conditions regarding the environment such as the weather, external temperature, temperature in the vehicle, etc., conditions regarding time such as year, date, period of time of day, etc., and conditions regarding health such as the temperature of the user. That is, when the user changes the shape of the seat, the AI learning unit 17 is able to learn the reason (condition) why the shape of the seat is changed. Therefore, when there are conditions similar to when the additional conditions are stored when the user sits in the seat, the AI learning unit 17 changes the shape of the seat based on the learned contents.

According to the present configuration example, as shown in FIG. 42, the control apparatus 10 and/or the information terminal 90 is connected to be able to communicate with the external server 96 managed by an administrator of an automobile manufacturer or seller, and the information learned by the AI learning unit 17 can be managed.

Described in detail, the information regarding the shape of the seat stored in the storage 12 by the AI learning unit 17 and the information regarding the additional condition when the shape of the seat is changed are transmitted to the external server 96 through the communicating unit 16. Then, the external server 96 always obtains information of an unspecified large number of users, analyzes the trends and features regarding the change of the shape of the seat and feeds back the analyzed information to each user (control apparatus 10).

Further, the information regarding the seated posture of the occupant obtained by changing the shape of the seat is collected and is used in investigation of usability for the physique and the seated posture. That is, the external server 96 managed by the administrator receives various information from a large number of users. Therefore, the above information is collected and analyzed as big data, and this leads to enhancing satisfaction for many users.

Configuration Example 5

[Regarding Link with Vehicle Body]

The various portions and functions of the vehicle body in the vehicle (automobile: car) can be linked according to the posture and the physique of the person seated in the seat.

Figure 44:
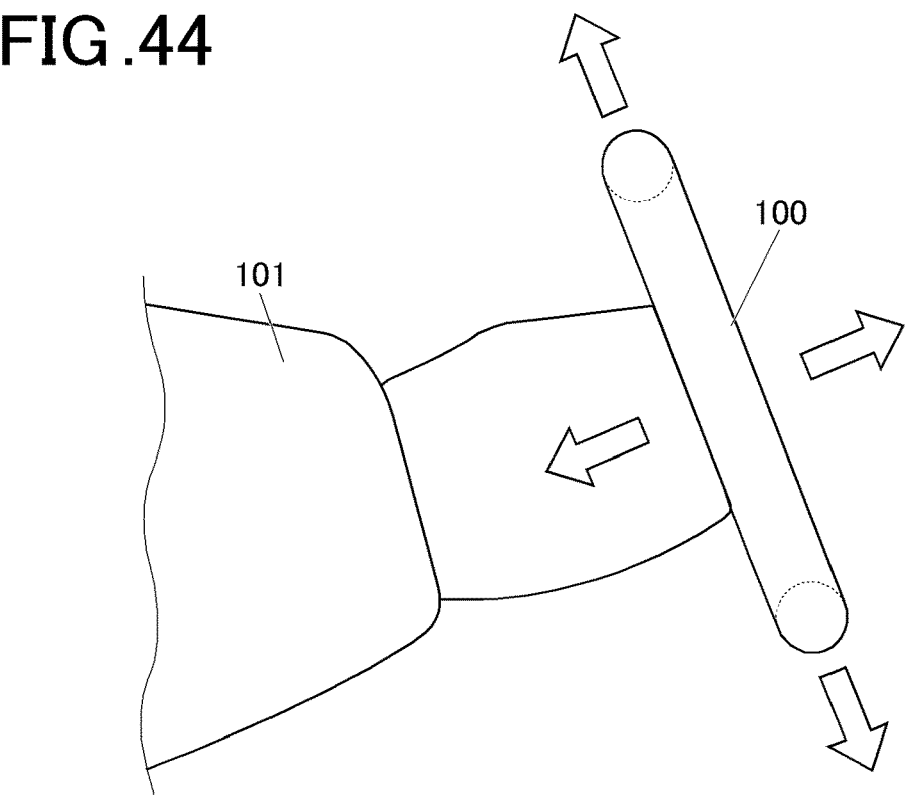
FIG. 44 is a diagram describing position adjustment of a steering wheel.

FIG. 44 is a diagram which describes position adjustment of the steering wheel 100, and the position adjustment of the steering wheel 100 is controlled by the control apparatus 10 based on the information regarding the posture and the physique of the person seated in the seat.

For example, the position of the height of the shoulder may be high for a person P1 with a tall sitting height, and the position of the shoulder may be low for the person P3 with the short sitting height. In most cases, the length of the arm is basically in proportion with the height.

In such case, for example, the degree of the sitting height of the person seated in the seat is detected, and based on the detection result, the angle of the steering wheel 100 in the up and down direction is changed. The length of the arm is estimated from the information regarding the input height, and based on the estimated result, the position of the steering wheel can be adjusted to the front and rear.

The mechanism to perform the position adjustment of the steering wheel 100 is called "tilt and telescopic steering".

A steering column 101 in which an axis (steering shaft) of the steering wheel 100 is stored includes a driver (not shown) which adjusts the position of the axis of the steering wheel 100 in the up and down direction and the front and rear direction. Such driver is connected to the control apparatus 10 and is controlled by the control apparatus 10.

With this, the position adjustment of the steering wheel 100 can be performed automatically based on the information regarding the posture and the physique of the person seated in the seat.

The information regarding the posture and the physique of the person seated in the seat can be input from a car navigation apparatus 102 (see FIG. 45 and FIG. 46) or can be input from the information terminal 90 such as a tablet terminal or smartphone.

Figure 45:
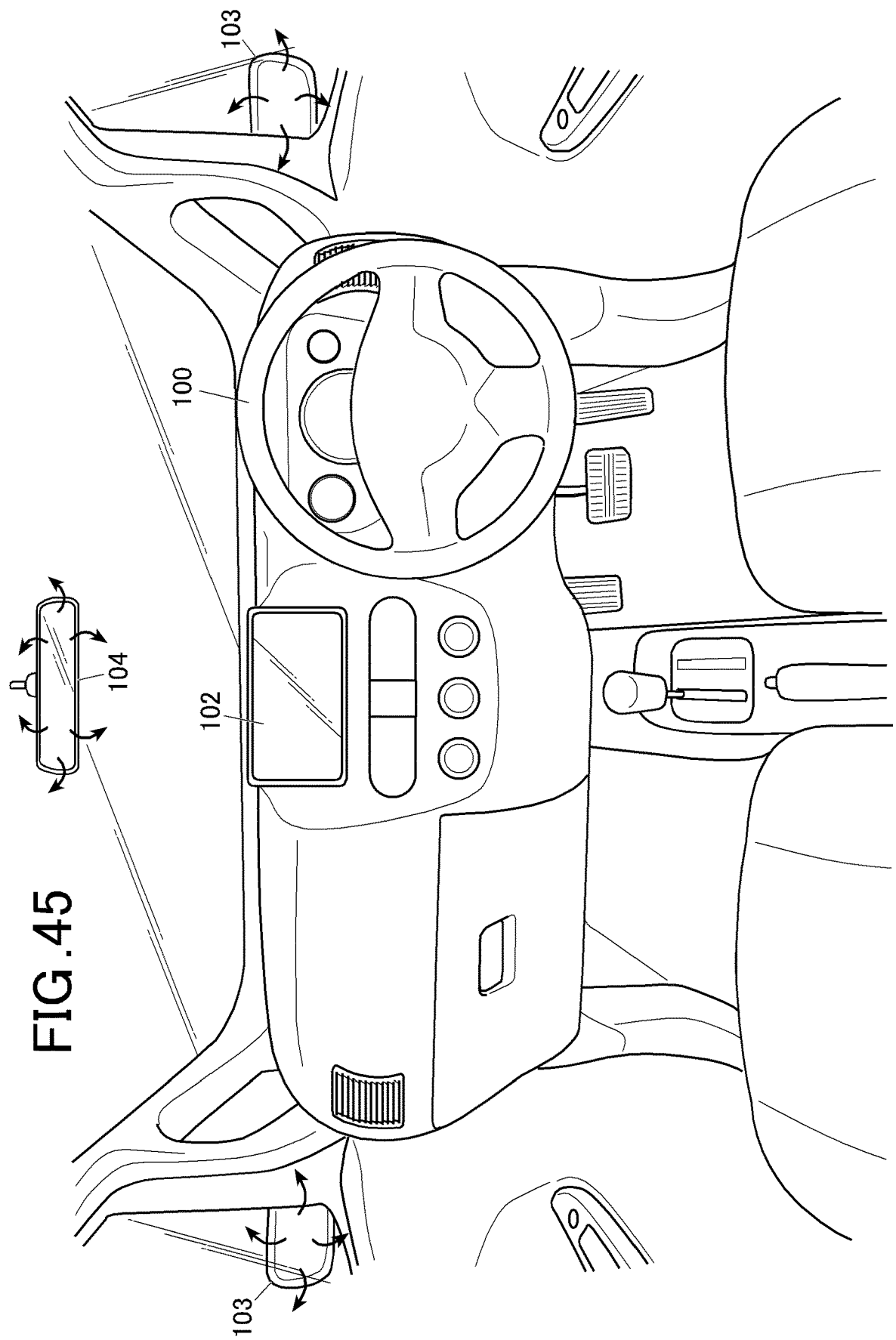
FIG. 45 is a diagram describing position adjustment of a side view mirror and a rear view mirror.

FIG. 45 is a diagram which describes the adjustment of the position of a side view mirror 103 and a rear view mirror 104 and the adjustment of the position of the side view mirror 103 and the rear view mirror 104 is controlled by the control apparatus 10 based on the information regarding the posture and physique of the person seated in the seat.

For example, the person P1 with the tall sitting height has a high view of sight, and the person P3 with the short sitting height has a low view of sight.

In such case, for example, the degree of the sitting height of the person seated in the seat can be detected and the angle of the side view mirror 103 and the rear view mirror 104 can be changed up, down, left, and right based on the detection result.

The adjustment of the angle of the side view mirror 103 and the rear view mirror 104 can be performed by detecting the eye point with the camera.

Figure 46:
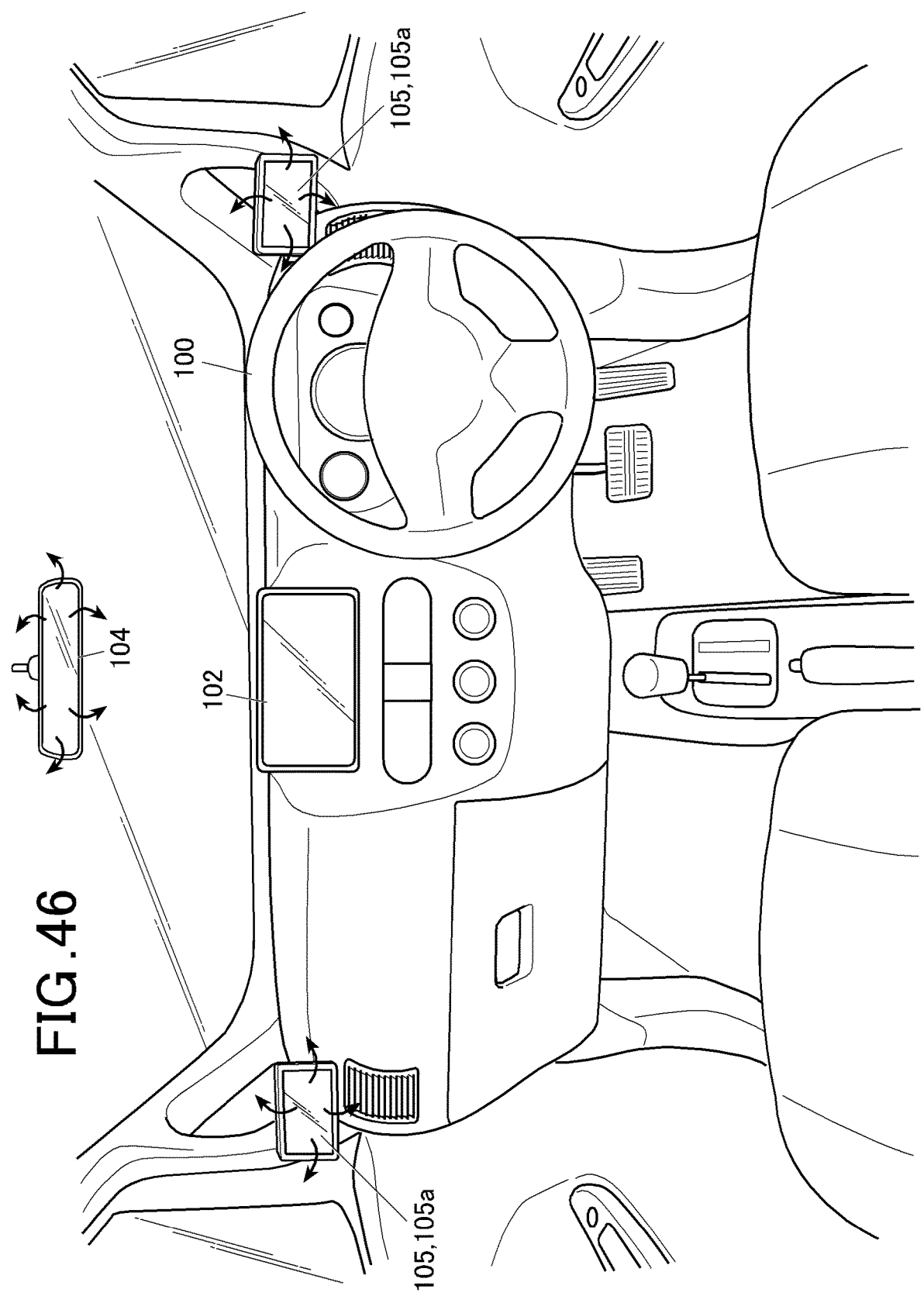
FIG. 46 is a diagram describing a position of a side view electronic mirror and a display adjustment.

FIG. 46 is a diagram describing when an electronic side view mirror 105 is provided instead of the side view mirror 103 and the adjustment of the position and the display of the electronic side view mirror 105.

The electronic side view mirror 105 includes a camera attached to the side of the vehicle body so as to image the rear, and a monitor 105a which is provided in the occupant cabin and which projects the moving image imaged by the camera.

The position and the display adjustment of the electronic side view mirror 105 is controlled by the control apparatus 10 based on the information regarding the posture and the physique of the person seated in the seat.

Described in detail, when the position of the screen displayed on the electronic side view mirror 105 is adjusted, the direction of the camera is adjusted by the control apparatus 10. When the position of the electronic side view mirror 105 itself is adjusted, the control apparatus 10 changes the angle of the monitor 105a to up, down, left, and right.

Each of the side view mirror 103, the rear view mirror 104, and the camera and the monitor 105a in the electronic side view mirror 105 includes a driver to adjust the direction and the position. With this, according to the configuration example shown in FIG. 45 and FIG. 46, based on the information regarding the posture and the physique of the person seated in the seat, the position and the display of the side view mirror 103, the rear view mirror 104, and the electronic side view mirror 105 can be adjusted automatically.

The information regarding the posture and the physique of the person seated in the seat can be performed by input of information from the car navigation apparatus 102 or can be performed by input of information from the information terminal such as a tablet terminal or a smartphone.

Figure 47:
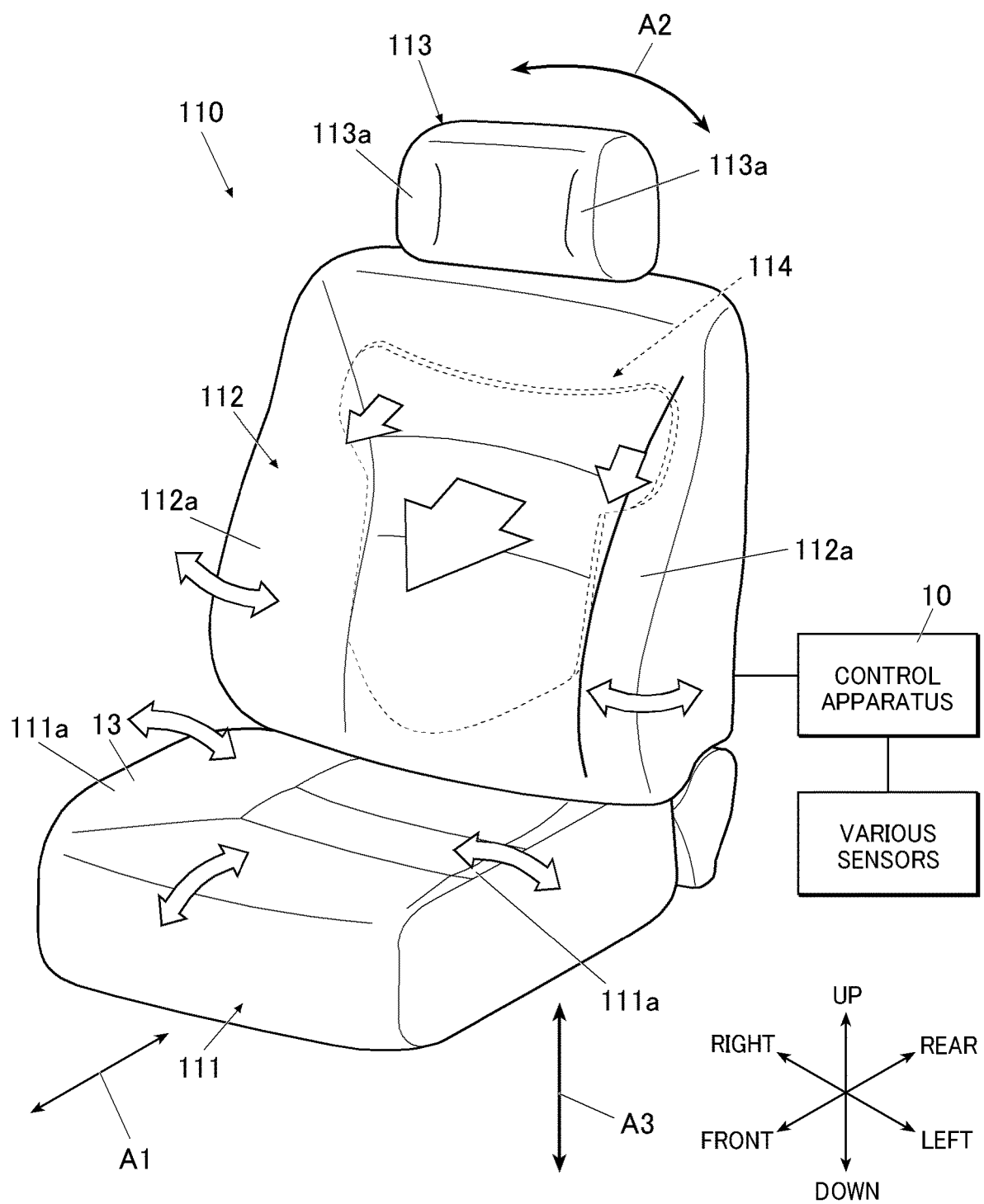
FIG. 47 is a diagram describing when a shape of a seat is changed.

FIG. 47 automatically performs change of the shape of the seat 110 including the side support and the lumbar support according to the control by the control apparatus 10.

The seat 110 includes a seat cushion 111, a seat back 112, and a headrest 113.

The seat back 112 is configured to be able to be deformed in the front and rear direction, and the lumbar support 114 which supports the lower back of the person seated in the seat 110 is provided inside.

The seat 110 is suitably provided with a sliding mechanism (see arrow A1), a reclining mechanism (see arrow A2), and a height mechanism (see arrow A3). The seat back 112 is provided with a middle fold mechanism which tilts the portion in the middle in the up and down direction of the seat back 112 in the front and rear direction. The height mechanism includes a link mechanism to adjust the position of the front edge and the rear edge of the cushion frame included in the skeleton of the seat cushion 111 in the up and down direction.

The side support 111a which inflates upward is provided on both edges of the seat cushion 111 in the width direction. The side support 112a which inflates forward is provided on both edges of the seat cushion 112 in the width direction. The side support 113a which inflates forward is provided on both edges of the head rest 113 in the width direction.

Inside each of the side support 111a, 112a, and 113a, an air cell which inflates by inserting a fluid inside is provided.

By increasing and decreasing the fluid in the air cell, the degree that each of the side support 111a, 112a, and 113a is inflated can be adjusted.

The control apparatus 10 can control the operation of the lumbar support 114, the side supports 111a, 112a, and 113a, and other mechanisms based on the detection result of the various sensors provided in the vehicle body.

Various sensors include, a sensor which detects centrifugal force during cornering, a sensor which detects a steering angle of the steering wheel, a sensor which detects sudden move and sudden stop, a sensor which detects operation of the brakes, a sensor which detects a parked state of the vehicle, a sensor which detects sleepiness of the occupant, and a sensor which detects an angle of the vehicle body.

Various types of sensors can be suitably employed as the above described various sensors, for example, an acceleration sensor, a load cell, or various position sensors.

When the vehicle is cornering while moving, the body of the person seated in the seat moves to the outer side due to centrifugal force. Therefore, when the sensor detects centrifugal force, based on the detection result, the side supports 111a, 112a, and 113a positioned on the outer side in the centrifugal direction among the side supports 111a, 112a, and 113a provided in the seat 110 deform to be in close contact with the side of the body of the occupant. Further, the outer side in the centrifugal direction of the lumbar support 114 deforms forward (closed to the inner side). The side supports 111a, 112a, and 113a positioned on the inner side in the centrifugal direction and the inner side in the centrifugal direction of the lumbar support 114 may deform backward (open to the outer side).

When the vehicle reaches a curve while being driven and the cornering is performed, the steering wheel is rotated at the same time. Therefore, when the sensor which detects centrifugal force operates, the sensor which detects the steering angle of the steering wheel also detects the rotation of the steering wheel. Therefore, the side supports 111a, 112a, and 113a and the lumbar support 114 may deform when the sensor which detects the steering angle of the steering wheel operates.

The steering angle of the steering wheel is different depending on the radius of the curve, and therefore, the degree of deforming of the side supports 111a, 112a, and 113a and the lumbar support 114 can be changed according to the steering angle of the steering wheel.

When the vehicle suddenly moves or suddenly stops, the buttock and the thigh of the person seated on the seat may shift and move on the seat cushion 111 and "buttock shift" may occur.

The sensor which detects the sudden move and the sudden stop operates when the vehicle suddenly moves or suddenly stops and detects the sudden move or the sudden stop. Based on the detection result, the control apparatus 10 performs control to deform the side supports 111a, 112a, and 113a forward to close to the inner side and holds the body of the occupant. Control to move the front edge of the seat cushion 111 upward can be performed at the same time. With this, the buttock shift occurring or the distance of the buttock moving when the buttock shift occurs can be suppressed when the vehicle suddenly moves or suddenly stops.

A vehicle may be provided with an automatic braking system which performs operation to support the brakes in order to avoid collision with an obstacle when an obstacle is detected by a radar or camera. Not limited to the automatic brake system, a sudden brake may be applied when the car is running other than the sudden stop. When such operation of the brakes is performed, the sensor which detects the operation of the brakes operates, and the operation of the brakes is detected. Based on the above detection result, the control apparatus 10 controls the deforming of the side supports 111a, 112a, and 113a and lumbar support 114 to be a posture which enhances safety of the occupant.

Described specifically, the control apparatus 10 deforms the lumbar support 114 to project forward, and sets the posture of the occupant in a state in which the back is bent backwards and the neck is made closer to the seat back 112 or the headrest 113. Further, control to deform the side supports 111a, 112a, and 113a is performed to be closed inward to the front and the body of the occupant is held. With this, the state of the neck of the occupant being close to the seat back 112 or the headrest 113 is maintained. Even if the collision with obstacles cannot be avoided, it is easier to secure the safety of the occupant.

Among the operation of the units in which the shape of the seat 110 is changed as described above, operation which is preferably not performed during driving may be included, In such case, the control apparatus 10 controls the change of the shape of the seat 110 after detecting the parked state of the vehicle with the sensor which detects the parked state of the vehicle.

With this, for example, among the operation of the units in which the shape of the seat 110 is changed, when the operation which is preferably not performed during driving is included, the operation is performed after confirming that the vehicle is in the parked state. Therefore, the safety is enhanced.

The sensor which detects the parked state of the vehicle is used, but the sensor which detects the stopped state of the vehicle can be used instead of or together with the sensor which detects the parked state.

As the sensor which detects sleepiness of the occupant, a camera is used to detect the state of the occupant closing his eyes for a certain period of time or more, or movement of the body or the posture of the person seated, or a sensor which detects the sleepiness from a state of the breath of the occupant, or a sensor which detects the sleepiness from the body temperature of the occupant is used.

When the sensor which detects the sleepiness of the occupant operates, based on the detection result, the control apparatus 10 controls the seat 110 to be deformed in a shape so that the occupant is in a posture which improves the situation of the sleepiness of the occupant. Specifically, the lumbar support 114 is projected forward and the lower back of the occupant is moved forward in order to urge the occupant to stretch. With this the sleepiness of the occupant can be improved.

Figure 48A:
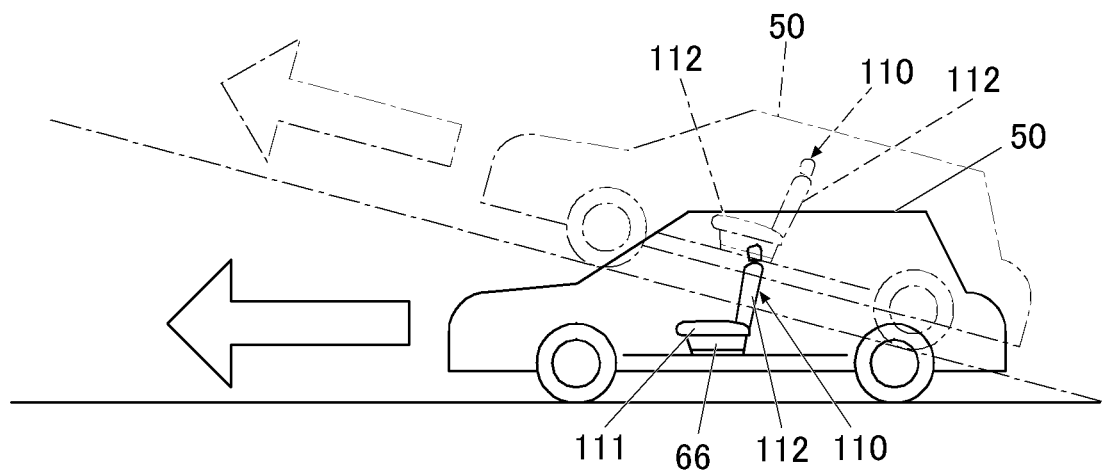
FIG. 48A is a diagram describing when a shape of a seat is changed when climbing a hill.

As shown in FIG. 48A, the vehicle 50 is greatly tilted more than horizontal when the vehicle climbs a hill, and the person seated in the seat 110 is also tilted at the same time. With this, the back may be in close contact with the seat back 112. Then, it becomes difficult for the person seated in the seat 110 to raise up the upper body and the field of view may become bad.

Figure 48B:
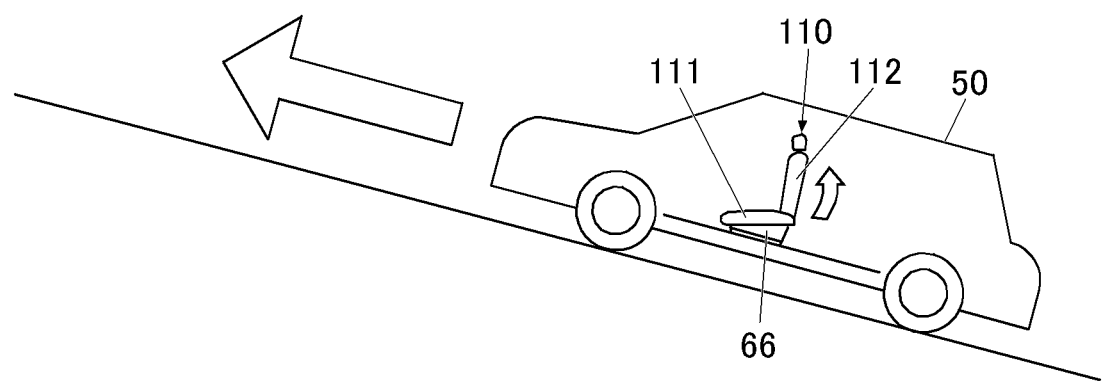
FIG. 48B is a diagram describing when the shape of the seat is changed when climbing a hill.

As shown in FIG. 48B, when the angle of the vehicle body 50 is a certain angle or more, the angle of the vehicle body is detected by the sensor which detects the angle of the vehicle body 50, and the control apparatus 10 performs the control to tilt the seat 110 to be closer to horizontal based on the detection result. Specifically, the height mechanism 66 moves the rear edge of the seat cushion 111 higher than the front edge. With this, the seat 110 can be tilted to be closer to horizontal, and the field of view of the person seated in the seat 110 does not become bad even when climbing a hill.

Figure 49:
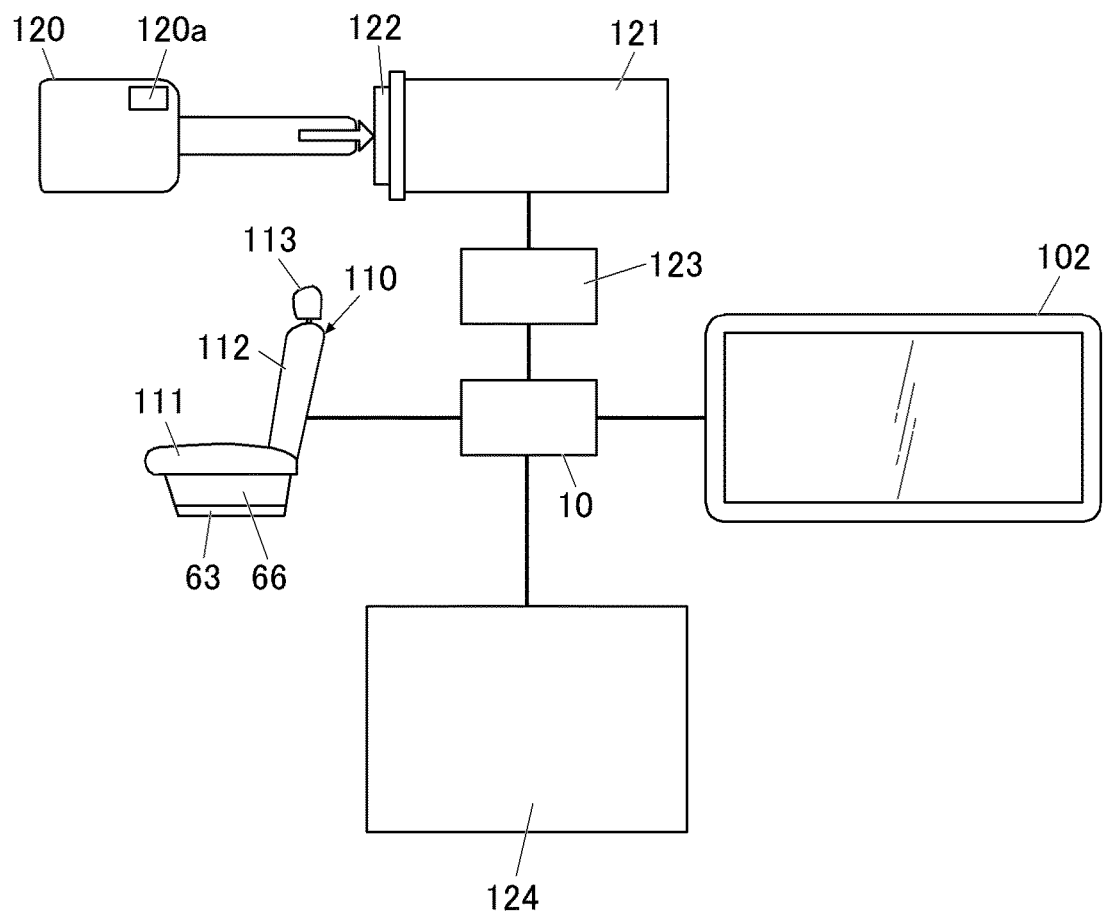
FIG. 49 is a diagram describing a configuration of changing a shape of a seat including an immobilizer.

The vehicle includes an immobilizer for the purpose of preventing theft of the vehicle. As shown in FIG. 49, the immobilizer includes a control apparatus 10, an engine key 120, a key cylinder 121, an antenna 122, and an amplifier 123, and the control apparatus 10 is connected to a vehicle engine 124, a car navigation apparatus 102, and a seat 110.

A transmitter 120a with an identification code called a transponder is embedded in the engine key 120. The identification code is transmitted from the transmitter 120a and is received by the antenna 122. The identification code is amplified by the amplifier 123, and the identification code is transmitted to the control apparatus.

In the control apparatus 10, the identification code and the identification code unique to the vehicle body is compared and the engine 124 starts if there is a match.

When there is no problem in comparing the identification code, the control apparatus 10 operates the seat 110 to the shape registered in advance. That is, the person who sits in the seat can change the seat 110 to the desired shape registered in advance by only getting on the vehicle, sitting in the seat 110, and starting the engine 124.

When there are a plurality of people who registered the change in the shape of the seat 110, a screen to select who is seated in the seat 110 is displayed on the car navigation apparatus 102, and the person who is seated can make a selection to change the shape of the seat 110 to the shape registered in advance.

The method to change the shape of the seat 110 when riding on the vehicle is not limited to the method using the immobilizer, and a method by performing input on the information terminal 90 such as a tablet terminal or a smartphone can be employed.

When the information terminal 90 is used, the control is performed based on pairing by Bluetooth (registered trademark) between the control apparatus 10 and the information terminal 90 and the information linked to the above. That is, when the owner of the information terminal pairs his information terminal 90 with the control apparatus 10, the user information can be sent to the control apparatus 10. With this, even if there are a plurality of people who registered the change of the shape of the seat 110, it is possible to change without trouble the shape of the seat 110 to the shape registered in advance by the certain person.

Figure 50:
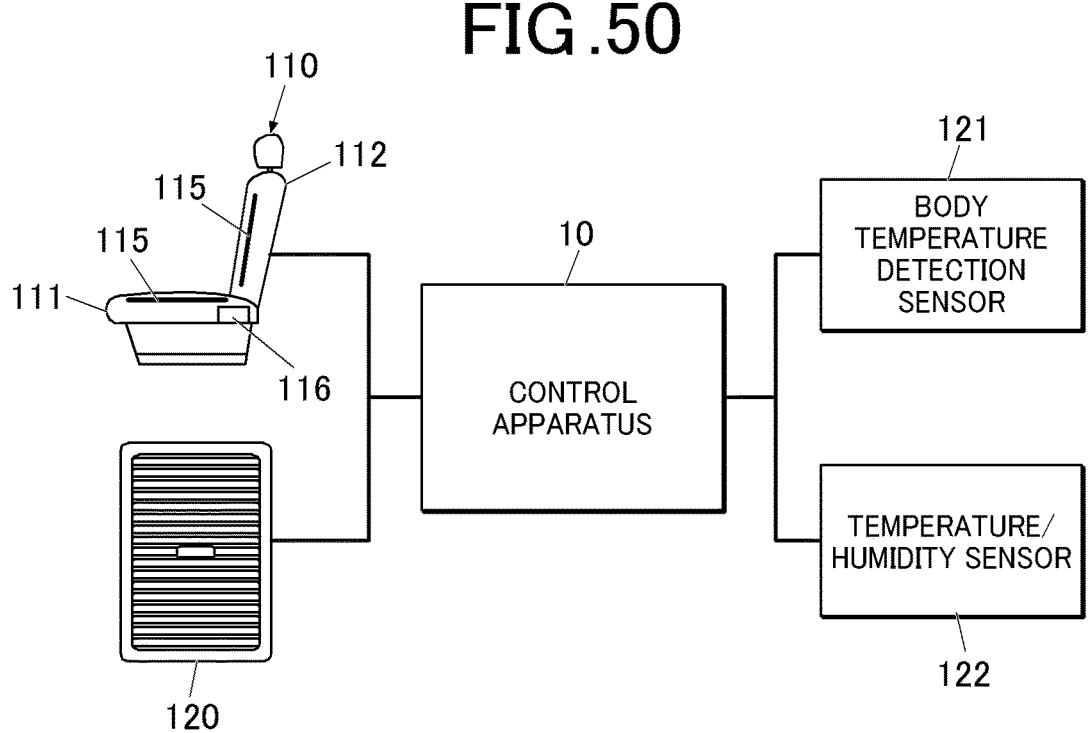
FIG. 50 is a diagram describing an example regarding a temperature adjustment.

As shown in FIG. 50, the control apparatus 10 is connected to a seat 110 in which a seat heater 115 and a blower 116 are included inside, an air conditioner 120 inside the vehicle, a body temperature detection sensor 121, and a temperature/humidity sensor 122. The seat heater 115 raises the temperature of the seat 110 and the blower 116 can decrease the temperature of the seat 110 by sending wind.

The body temperature detection sensor 121 is a sensor for detecting body temperature of the person seated in the seat 110. The body temperature detection sensor 121 is included inside the seat 110 or is provided on a vehicle body near the seat 110.

The temperature/humidity sensor 122 is a sensor which detects the temperature and the humidity at least outside the vehicle, and is provided outside the vehicle. Other than the temperature/humidity sensor 122 provided outside the vehicle, the temperature/humidity sensor 122 can be provided inside the vehicle.

The control apparatus 10 can suitably control the operation of the seat heater 115, the blower 116, and the air conditioner 120 based on the detection result of the body temperature detection sensor 121 and the temperature/humidity sensor 122.

That is, for example, the body temperature detection sensor 121 detects the body temperature of the person seated in the seat 110 and for example, the control apparatus 10 is able to operate the air conditioner 120 based on the detection result. At this time, the control apparatus 10 is able to operate the seat heater 115 or the blower 116 instead of or together with the air conditioner 120.

The temperature/humidity sensor 122 detects the temperature and the humidity outside or inside the vehicle, and based on the detection result, the control apparatus 10 is able to operate either the seat heater 115 or the blower 116. At this time, the control apparatus 10 is able to operate the air conditioner 120 instead of or in addition to the seat heater 115 or the blower 116.

Figure 51:
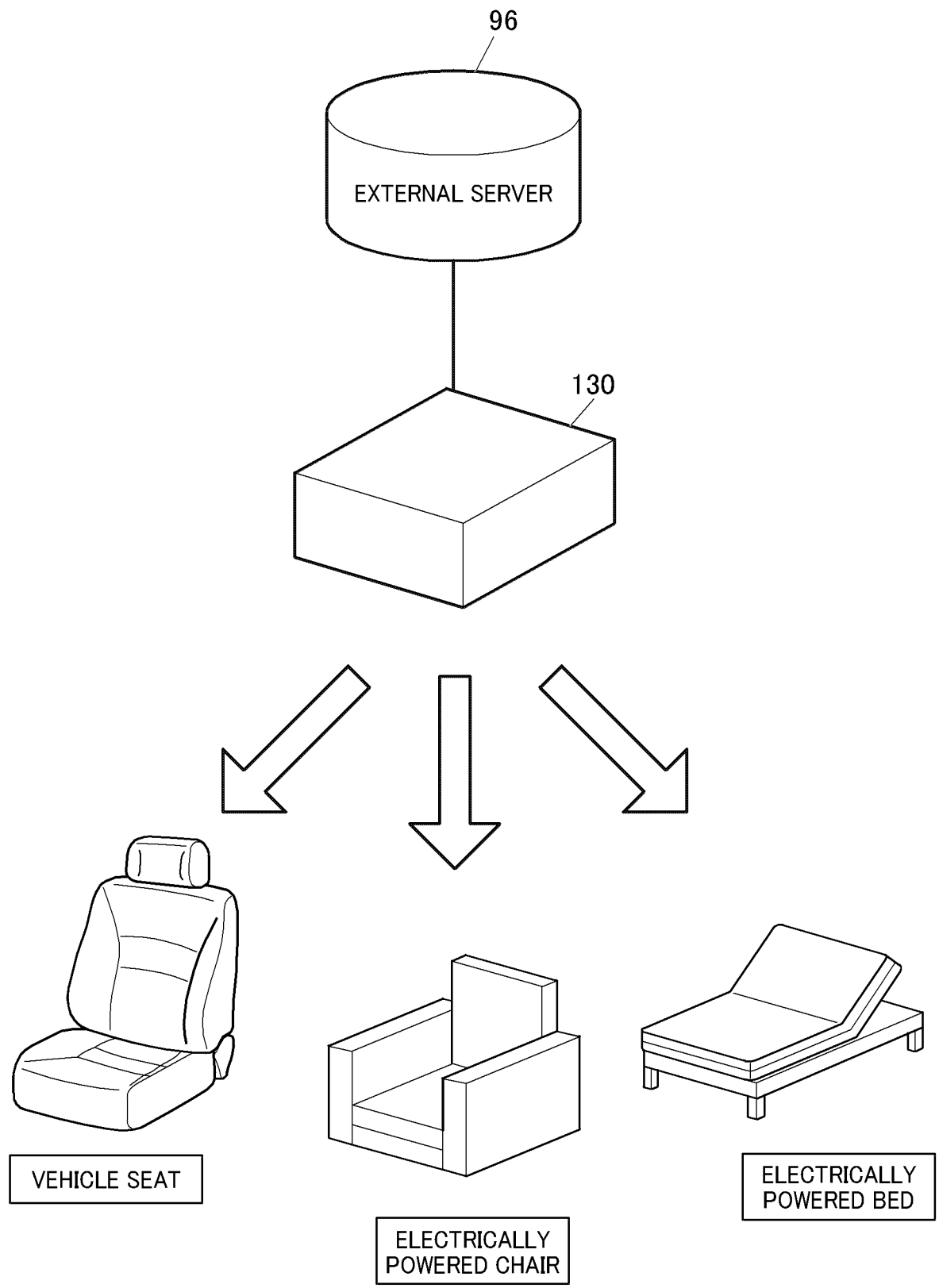
FIG. 51 is a diagram describing an ECU unit.

The control apparatus 10 called an ECU as described above can be configured as a unit separated from the vehicle as shown in FIG. 51. That is, the control apparatus 10 can be configured as an ECU unit 130 and mounted on the vehicle later on.

Such ECU unit 130 can be connected wired or wireless and is able to transmit and receive information with positions of the seat where electric adjustment is possible.

Here, positions of the seat where electric adjustment is possible include devices as described above (for example, the above described pillar driver, slide rail, lumbar support, reclining mechanism, height mechanism, middle fold mechanism of seat back, position adjustment mechanism of front and rear edge in height mechanism, seat heater, blower, etc.), various sensors necessary to change the shape of the seat, and various devices provided on the vehicle body side of the vehicle (side view mirror, rear view mirror, electronic side view mirror, immobilizer, air conditioner, etc.).

The ECU unit 130 can transmit and receive information with the external server 96 and can include an AI learning unit.

The ECU unit 130 configured as described above is applied to an existing simple seat provided with positions which can be adjusted electrically, and the seat can operate as an electric seat in which units can be adjusted automatically according to information regarding the posture and the physique of the individual, preferences, and other information regarding the occupant.

The ECU unit 130 is not only applied to the seat of the vehicle as described above, and can be applied to a sitting unit such as a chair or a sofa provided with various devices as described above (electric devices also called powered device) (electrically powered chair as shown in FIG. 51), electric bed (electrically powered bed shown in FIG. 51), and the like. Specifically, the above can be applied to a medical bed, office chair, bench in a waiting room, chair for a dentist, seat in an airplane, seat in a train, seat in a ship, driver's seat for a public transportation system, sofa for homes, electric wheel chair, and the like.

INDUSTRIAL APPLICABILITY

The ECU device, vehicle seat, system for estimating lower limb length of a seated person, and attachment structure for a sitting height detection sensor according to the present invention enables an accurate estimate of the length of the lower limb of the person seated in the vehicle seat and also provides a specific attachment structure which enables detection of the sitting height by the sitting height detection sensor. The supporting rigidity of the sitting height detection sensor becomes high and therefore, the industrial applicability is enhanced.

REFERENCE SIGNS LIST

201 ECU device
202 thigh angle information obtainer
203 back knee angle information obtainer
204 estimator
210 vehicle seat
211 seat cushion
211A pulled portion
218 seat frame
A seated person
D knee or shin
E heel
s1 to s4 sitting pressure sensor
S11 to S13 pressure sensor
S21, S22 infrared sensor
s31 first infrared sensor
s32 second infrared sensor
x1 to x4 sitting pressure
y moving distance
Y1 first distance
Y2 second distance
y21, y22 distance to calf
z length of lower limb
φ back knee angle
θ thigh angle
P1 person with tall sitting height
P2 person with middle sitting height
P3 person with short sitting height
H1 head
H2 head
H3 head
1 seat
2 seat cushion
2a sitting sensor
2b weight measurement sensor
3 seat back
3a pillar driver
4 headrest
4a cushion pad
4b outer layer
5 headrest pillar
5a column
5b horizontal axis
6 sitting height detection sensor
7a lower side sensor main body
7b upper side sensor main body
8 bracket
8a fixing member
10 control apparatus
11 controller
12 storage
13 input unit
14 output unit
15 seat posture adjustment apparatus
20 sensor main body
21 first sub-sensor
22 second sub-sensor
30 sensor main body
31 first sub-sensor
32 second sub-sensor

The invention claimed is:

1. An ECU device which estimates a length of a lower limb of a seated person who is seated in a vehicle seat, the ECU device comprising:
a thigh angle information obtainer which obtains information regarding a thigh angle of the seated person;

a back knee angle information obtainer which obtains information regarding a back knee angle of the seated person;

an estimator which estimates the length of the lower limb of the seated person based on the information regarding the thigh angle obtained by the thigh angle information obtainer and information regarding the back knee angle obtained by the back knee angle information obtainer.

2. The ECU device according to claim 1, wherein the thigh angle information obtainer obtains sitting pressure measured by a sitting pressure sensor positioned in a seat cushion of the vehicle seat as the information regarding the thigh angle.

3. The ECU device according to claim 2, wherein,
the seat cushion includes a seat frame, a cushion pad, and an outer layer, and
the sitting pressure sensor is positioned in a position avoiding a concave provided in the cushion pad of the seat cushion.

4. The ECU device according to claim 1, wherein the back knee angle information obtainer obtains as the information regarding the back knee angle whether pressure is detected by a pressure sensor positioned in a front edge of a seat cushion of the vehicle seat in which the front edge can move in a front and rear direction of the vehicle seat and a moving distance of the front edge.

5. The ECU device according to claim 1, wherein the back knee angle information obtainer obtains as the information regarding the back knee angle distances to a calf of the seated person measured by a plurality of infrared sensors positioned in a front edge of a seat cushion of the vehicle seat.

6. The ECU device according to claim 1, wherein,
the thigh angle information obtainer obtains as the information regarding the thigh angle a first distance to a knee or a shin measured by irradiating an infrared laser from a first infrared sensor to the knee or the shin of the seated person, and
the back knee angle information obtainer obtains as the information regarding the back knee angle a second distance to a heel measured by irradiating the infrared laser to the heel of the seated person from a second infrared sensor.

7. A vehicle seat in which the ECU device according to claim 1 is attached to the seat frame.

8. A system for estimating a lower limb length of a seated person to estimate a length of a lower limb of a seated person seated in the vehicle seat, the system comprising:

a thigh angle information obtainer which obtains information regarding a thigh angle of the seated person;
a back knee angle information obtainer which obtains information regarding a back knee angle of the seated person; and
an estimator which estimates the length of the lower limb of the seated person based on the information regarding the thigh angle obtained by the thigh angle information obtainer and the information regarding the back knee angle obtained by the back knee angle information obtainer.

9. An attachment structure for a sitting height detection sensor wherein,
in a vehicle seat provided with an ECU device according to claim 1, a headrest which supports a head of a seated person is supported with a seat back by a headrest pillar,
the headrest is able to move up and down with relation to the seat back along the headrest pillar, and
a sitting height detection sensor which detects a sitting height of the seated person seated in the seat is supported by the headrest pillar.

10. The attachment structure for the sitting height detection sensor according to claim 9, wherein,
the headrest pillar includes a pair of columns separated between left and right and a horizontal axis placed across upper edges of the pair of columns, and
the sitting height detection sensor is positioned in the center of the horizontal axis.

11. The attachment structure for the sitting height detection sensor according to claim 9, wherein,
the sitting height detection sensor includes a sensor main body and a bracket in which the sensor main body is fixed to a front surface, and
the bracket is positioned on a front side of the headrest pillar.

12. The attachment structure for the sitting height detection sensor according to claim 9, wherein,
the sitting height detection sensor includes a sensor main body and a bracket in which the sensor main body is fixed to a front surface, and
the bracket is positioned on a rear side of the headrest pillar.

13. The attachment structure for the sitting height detection sensor according to claim 9, wherein the sitting height detection sensor includes a sub-sensor which detects a tilt of a head of the seated person.

* * * * *